(12) United States Patent
Nyanguile et al.

(10) Patent No.: US 10,774,114 B2
(45) Date of Patent: Sep. 15, 2020

(54) RESPIRATORY SYNCYTIAL VIRUS (RSV) REPLICATION INHIBITORS

(71) Applicant: FONDATION THE ARK, Sion (CH)

(72) Inventors: Origéne Nyanguile, Grimisuat (CH); Jean-François Eleouet, Breuillet (FR); Marie Galloux, Paris (FR)

(73) Assignee: FONDATION THE ARK, Sion (CH)

(*) Notice: Subject to any disclaimer, the term of this patent is extended or adjusted under 35 U.S.C. 154(b) by 0 days.

(21) Appl. No.: 15/125,309

(22) PCT Filed: Mar. 10, 2015

(86) PCT No.: PCT/EP2015/054930
§ 371 (c)(1),
(2) Date: Sep. 12, 2016

(87) PCT Pub. No.: WO2015/135925
PCT Pub. Date: Sep. 17, 2015

(65) Prior Publication Data
US 2017/0152292 A1   Jun. 1, 2017

Related U.S. Application Data

(60) Provisional application No. 61/950,488, filed on Mar. 10, 2014, provisional application No. 62/077,410, filed on Nov. 10, 2014.

(51) Int. Cl.
*A61K 38/00* (2006.01)
*C07K 14/005* (2006.01)
*C07K 14/135* (2006.01)

(52) U.S. Cl.
CPC .......... *C07K 14/005* (2013.01); *C07K 14/135* (2013.01); *A61K 38/00* (2013.01); *C07K 2319/10* (2013.01); *C12N 2760/18522* (2013.01); *C12N 2760/18533* (2013.01)

(58) Field of Classification Search
CPC .... A61K 38/00; C07K 14/005; C07K 14/135; C07K 2319/10; C12N 2760/18533; C12N 2760/18522; G06N 5/025; G16H 50/20
See application file for complete search history.

(56) References Cited

U.S. PATENT DOCUMENTS 7,531,342 B2 * 5/2009 Fouchier .............. C07K 14/005
424/211.1

FOREIGN PATENT DOCUMENTS

| WO | WO 2008/121767 | 10/2008 |
|---|---|---|
| WO | WO 2010/011313 | 1/2010 |
| WO | WO 2010/060112 | 5/2010 |
| WO | WO 2010/068684 | 6/2010 |

OTHER PUBLICATIONS

Third Party Observation Communication from European Application No. 20150708824, dated Apr. 25, 2017, pp. 1-4.

Tawar, R.G. et al. "Crystal structure of a nucleocapsid-like nucleoprotein-RNA complex of respiratory syncytial virus" *Science*, Nov. 27, 2009, pp. 1-2, vol. 326, No. 5957, Abstract Only.

Leyrat, C. et al. "The $N^\upsilon$-binding region of the vesicular stomatitis virus phosphoprotein is globally disordered but contains transient $\alpha$-helices" *Protein Science*, 2011, pp. 542-556, vol. 20.

Karlin, D. et al. "Detecting Remote Sequence Homology in Disordered Proteins: Discovery of Conserved Motifs in the N-Termini of Mononegavirales phosphoproteins" *PLOS ONE*, Mar. 2012, pp. 1-16, vol. 7, Issue 3, e31719.

Castel, G. et al. "Peptides That Mimic the Amino-Terminal End of the Rabies Virus Phosphoprotein Have Antiviral Activity" *Journal of Virology*, Oct. 2009, pp. 10808-10820, vol. 83, No. 20.

Leyrat, C. et al. "Structure of the Vesicular Stomatitis Virus $N^\upsilon$-P Complex" *PLoS Pathogens*, Sep. 2011, pp. 1-12, e1002248, vol. 7, No. 9.

Yabukarski, F. et al. "Structure of Nipah virus unassembled nucleoprotein in complex with its viral chaperone" *Nature Structural & Molecular Biology*, Sep. 1, 2014, pp. 754-759, vol. 21, No. 9.

Bird, G. H. et al. "Hydrocarbon double-stapling remedies the proteolytic instability of a lengthy peptide therapeutic" *Proceedings of the National Academy of Sciences*, Aug. 10, 2010, pp. 14093-14098, vol. 107, No. 32.

Castagné, N. et al. "Biochemical characterization of the respiratory syncytial virus P-P and P-N protein complexes and localization of the P protein oligomerization domain" *Journal of General Virology*, 2004, pp. 1643-1653, vol. 85.

Collins, P. L. et al. "Progress in understanding and controlling respiratory syncytial virus: still crazy after all these years" *Virus Research*, Dec. 2011, pp. 1-48, vol. 162, Nos. 1-2.

Fix, J. et al. "The Insertion of Fluorescent Proteins in a Variable Region of Respiratory Syncytial Virus L Polymerase Results in Fluorescent and Functional Enzymes But with Reduced Activities" *The Open Virology Journal*, 2011, pp. 103-108, vol. 5.

Futaki, S. et al. "Arginine-rich Peptides: An Abundant Source of Membrane-Permeable Peptides Having Potential as Carriers for Intracellular Protein Delivery" *The Journal of Biological Chemistry*, Feb. 23, 2001, pp. 5836-5840, vol. 276, No. 8.

Galloux, M. et al. "Characterization of a Viral Phosphoprotein Binding Site on the Surface of the Respiratory Syncytial Nucleoprotein" *Journal of Virology*, Aug. 2012, pp. 8375-8387, vol. 86, No. 16.

Galloux, M. et al. "Is the RSV $N^\upsilon$-P complex a good target for antiviral strategies?" *9th International Respiratory Syncytial Virus Symposium*, Presented Nov. 10, 2014, Poster No. 25, p. 1.

Eleouet, J. et al. "Is the RSV NO-p Complex A Good Target for Antiviral Strategies?" *9th Respiratory Syncytial Virus Symposium*, Presented Nov. 10, 2014, Poster 25, Abstract No. 36, p. 43.

Galloux, M. et al. "Identification and Characterization of the Binding Site of the Respiratory Syncytial Virus Phosphoprotein to RNA-Free Nucleoprotein" *Journal of Virology*, Apr. 2015, pp. 3484-3496, vol. 89, No. 7.

(Continued)

*Primary Examiner* — Thomas S Heard
(74) *Attorney, Agent, or Firm* — Saliwanchik, Lloyd & Eisenschenk

(57) ABSTRACT

The invention provides polypeptides interacting with the binding of the RSV phosphoprotein P with the RSV nucleoprotein N and methods of using such polypeptides in the treatment and/or prevention of RSV infection.

17 Claims, 17 Drawing Sheets
Specification includes a Sequence Listing.

(56) References Cited

OTHER PUBLICATIONS

Hardy, R. W. et al. "The Product of the Respiratory Syncytial Virus M2 Gene ORF1 Enhances Readthrough of Intergenic Junctions during Viral Transcription" *Journal of Virology*, Jan. 1998, pp. 520-526, vol. 72, No. 1.
Kawamoto, S. A. et al. "Design of Triazole-stapled BCL9 α-Helical Peptides to Target the β-Catenin/B-cell CLL/lymphoma 9 (BCL9) Protein-Protein Interaction" *Journal of Medicinal Chemistry*, Feb. 9, 2012, pp. 1-21, vol. 55, No. 3.
Kim, Y.-W. et al. "Synthesis of all-hydrocarbon stapled α-helical peptides by ring-closing olefin metathesis" *Nature Protocols*, May 12, 2011, pp. 761-771, vol. 6, No. 6.
Kirchdoerfer, R. N. et al. "Assembly of the Ebola Virus Nucleoprotein from a Chaperoned VP35 Complex" *Cell Reports*, Jul. 7, 2015, pp. 140-149, vol. 12.
Kole, H. K. et al. "A Peptide-based Protein-tyrosine Phosphatase Inhibitor Specifically Enhances Insulin Receptor Function in Intact Cells" *The Journal of Biological Chemistry*, Jun. 14, 1996, pp. 14302-14307, vol. 271, No. 24.
Lassoued, S. et al. "NMR reveals α-helical propensity in RSV P protein outside the oligomerization domain" *Negative Strand Virus Meeting (NSV)*, Jun. 16-21, 2013, poster, p. 1.
Mason, S. W. et al. "Interaction between Human Respiratory Syncytial Virus (RSV) M2-1 and P Proteins Is Required for Reconstitution of M2-1-Dependent RSV Minigenome Activity" *Journal of Virology*, Oct. 2003, pp. 10670-10676, vol. 77, No. 19.
Park, M. et al. "A Readily Applicable Strategy to Convert Peptides to Peptoid-based Therapeutics" *PLoS ONE*, Mar. 21, 2013, e58874, pp. 1-7, vol. 8, No. 3.
Qian, Z. M. et al. "Targeted Drug Delivery via the Transferrin Receptor-Mediated Endocytosis Pathway" *Pharmacological Reviews*, 2002, pp. 561-587, vol. 54, No. 4.
Rameix-Welti, M.-A. et al. "Visualizing the replication of respiratory syncytial virus in cells and in living mice" *Nature Communications*, Oct. 3, 2014, pp. 1-10, vol. 5.
Schafmeister, C. E. et al. "An All-Hydrocarbon Cross-Linking System for Enhancing the Helicity and Metabolic Stability of Peptides" *Journal of American Chemical Society*, 2000, pp. 5891-5892, supporting information pp. 1-7, vol. 122.

Sia, S. K. et al. "Short constrained peptides that inhibit HIV-1 entry" *Proceedings of the National Academy of Sciences*, Nov. 12, 2002, pp. 14664-14669, vol. 99, No. 23.
Stewart, M. L. et al. "The MCL-1 BH3 Helix is an Exclusive MCL-1 inhibitor and Apoptosis Sensitizer" *Nature Chemical Biology*, Aug. 2010, pp. 1-17, vol. 6, No. 8.
Structures of VSV Nipah Ebola as in Reply to the Written Opinion of ISA (dated Nov. 1, 2016), p. 1.
Thompson, W. W. et al. "Mortality Associated With Influenza and Respiratory Syncytial Virus in the United States" *The Journal of the American Medical Association*, Jan. 8, 2003, pp. 179-186, vol. 289, No. 2.
Tran, T.-L. et al. "The Respiratory Syncytial Virus M2-1 Protein Forms Tetramers and Interacts with RNA and P in a Competitive Manner" *Journal of Virology*, Jul. 2009, pp. 6363-6374, vol. 83, No. 13.
Verdine, G. L. et al. "Stapled Peptides for Intracellular Drug Targets" *Methods in Enzymology*, In: Protein Engineering for Therapeutics, Part B, Jan. 1, 2012, pp. 3-33, vol. 503.
Walensky, L. D. et al. "Activation of Apoptosis in Vivo by a Hydrocarbon-Stapled BH3 Helix" *Science*, Sep. 3, 2004, pp. 1-10, vol. 305, No. 5689.
Wunderlich, K. et al. "Identification of High-Affinity PB1-Derived Peptides with Enhanced Affinity to the PA Protein of Influenza A Virus Polymerase" *Antimicrobial Agents and Chemotherapy*, Feb. 2011, pp. 696-702, vol. 55, No. 2.
Written Opinion in International Application No. PCT/EP2015/054930, dated Jun. 22, 2015, pp. 1-6.
Blackwell, H. E. et al. "Ring-Closing Metathesis of Olefinic Peptides: Design, Synthesis and Structural Characterization of Macrocyclic Helical Peptides" *The Journal of Organic Chemistry*, 2001, pp. 5291-5302, vol. 66, No. 16.
Ioannides, C. G. et al. "Inhibition of IL-2 Receptor Induction and IL-2 Production in the Human Leukemic Cell Line Jurkat by a Novel Peptide Inhibitor of Protein Kinase C" *Cellular Immunology*, 1990, pp. 242-252, vol. 131.
Sela, M. et al. "Different roles of D-amino acids in immune phenomena" *FASEB Journal*, 1997, pp. 449-456, vol. 11, No. 6.

* cited by examiner

Figure 2

```
          1         10         20         30        40
          |         |          |          |         |
          MEKFAPEFHG EDANNRATKFLESIKGK FTSPKDPKKKDSI
              Mir motif
```

| Mutant | Sequence | Reduced polymerase activty (≥ 50%) | In vitro copurification of N$^{mono}$ by GST-P[1-40] | K$_D$ (μM) calculated by SPR |
|---|---|---|---|---|
| E2A  | -A--------- ---------- ---------------- ------------- | + | + | 1.89 +/- 0.33 |
| K3A  | --A-------- ---------- ---------------- ------------- | - | + | 3.49 +/- 0.74 |
| F4A  | ---A------- ---------- ---------------- ------------- | + | - | 13.8 +/- 1.3 |
| P6A  | -----A----- ---------- ---------------- ------------- | - | + | 4.89 +/- 0.35 |
| E7A  | ------A---- ---------- ---------------- ------------- | + | +/- | 11.05 +/- 0.9 |
| F8A  | -------A--- ---------- ---------------- ------------- | + | - | 41 +/- 3.6 |
| H9A  | --------A-- ---------- ---------------- ------------- | - | + | 4 +/- 0.54 |
| G10A | ---------A- ---------- ---------------- ------------- | + | - | 5.1 +/- 1.7 |
| E11A | ---------- A--------- ---------------- ------------- | - | + | nd |
| D12A | ---------- -A-------- ---------------- ------------- | - | + | nd |
| N14A | ---------- ---A------ ---------------- ------------- | - | + | nd |
| N15A | ---------- ----A----- ---------------- ------------- | - | + | nd |
| R16A | ---------- -----A---- ---------------- ------------- | - | + | nd |
| T18A | ---------- -------A-- ---------------- ------------- | - | + | nd |
| K19A | ---------- --------A- ---------------- ------------- | - | + | nd |
| F20A | ---------- ---------A ---------------- ------------- | + | - | > 100 |
| L21A | ---------- ---------- A--------------- ------------- | + | +/- | 17.6 +/- 1.3 |
| E22A | ---------- ---------- -A-------------- ------------- | + | + | 7.49 +/- 1.14 |
| S23A | ---------- ---------- --A------------- ------------- | - | + | 4.5 +/- 0.62 |
| I24A | ---------- ---------- ---A------------ ------------- | + | - | 16.4 +/- 1.3 |
| K25A | ---------- ---------- ----A----------- ------------- | + | +/- | 7.77 +/- 1 |
| G26A | ---------- ---------- -----A---------- ------------- | + | + | 2.57 +/- 0.74 |
| K27A | ---------- ---------- ------A--------- ------------- | - | + | nd |
| F28A | ---------- ---------- -------A-------- ------------- | - | + | nd |

Figure 6A

| | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|
| HEVS 73 | E | D | A | N | N | K | A | T | K | F | L | E | S | I | K | G | K | F | A | S |
| HEVS 75 | | | | | S5 | | | | S5 | | | | | | | | | | | |
| HEVS 76 | ■ | | | | R5 | | | | S5 | | | | | | | | | | | |
| HEVS 77 | | | | | R8 | | | | | | | | S5 | | | | | | | |
| HEVS 74 | | | | | | | | | S5 | | | | S5 | | | | | | | |
| HEVS 108 | | | | | | | | | R8 | | | | | | | S5 | | | | |
| HEVS 109 | | | | | | | | | | | | | R5 | | | S5 | | | | |
| HEVS 78 | | | | | | | | | | | | | S5 | | | | S5 | | | |
| HEVS 79 | | | | | | | | | | | | | R8 | | | | | | | S5 |
| HEVS 110 | | | | | | | | | | | | | | | | S5 | | | | S5 |
| HEVS 111 | | | | | | | | | | | | | | | | | R5 | | | S5 |
| HEVS 112 | | | | | | | | | | | | | | | | R5 | | S5 | | |
| HEVS 113 | | | | | | | | | | | R8 | | | | | | | S5 | | |
| HEVS 114 | | | | | | | | | | | S5 | | | | | S5 | | | | |
| HEVS 115 | | | | | | | | | R5 | | S5 | | | | | | | | | |
| HEVS 116 | | | | | | | S5 | | S5 | | | | | | | | | | | |
| HEVS 117 | | | | R8 | | | | | S5 | | | | | | | | | | | |
| HEVS 118 | | | | R5 | | | S5 | | | | | | | | | | | | | |
| HEVS 128 | | | | | | | | S5 | | | | | S5 | | | | | | | |
| HEVS 129 | | | | | | | | | | R5 | | | S5 | | | | | | | |

Figure 6B

| | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|
| HEVS 73 | E | D | A | N | N | K | A | T | K | F | L | E | S | I | K | G | K | F | A | S |
| HEVS 120 | | | | | R8 | | | | | | | | SR5 | | | | | | | S8 |
| HEVS 121 | | | | | S8 | | | | | | | | SR5 | | | | S5 | | | |
| HEVS 122 | | | | | S5 | | | | S5 | | | | S5 | | | | S5 | | | |
| HEVS 123 | | | | | S5 | | | | S5 | | | | R8 | | | | | | | S5 |

Figure 6C

| | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|
| WT | E | F | H | G | E | D | A | N | N | K | A | T | K | F | L | E | S | I | K | G | K | F | A | S |
| HEVS 124 | | | | | | | | | | R8 | | | | S5 | | | | | | | | | | |
| HEVS 125 | | S5 | | | | S5 | | | | R8 | | | | S5 | | | | | | | | | | |
| HEVS 126 | | | R5 | | | S5 | | | | R8 | | | | S5 | | | | | | | | | | |

Figures 10 B & C
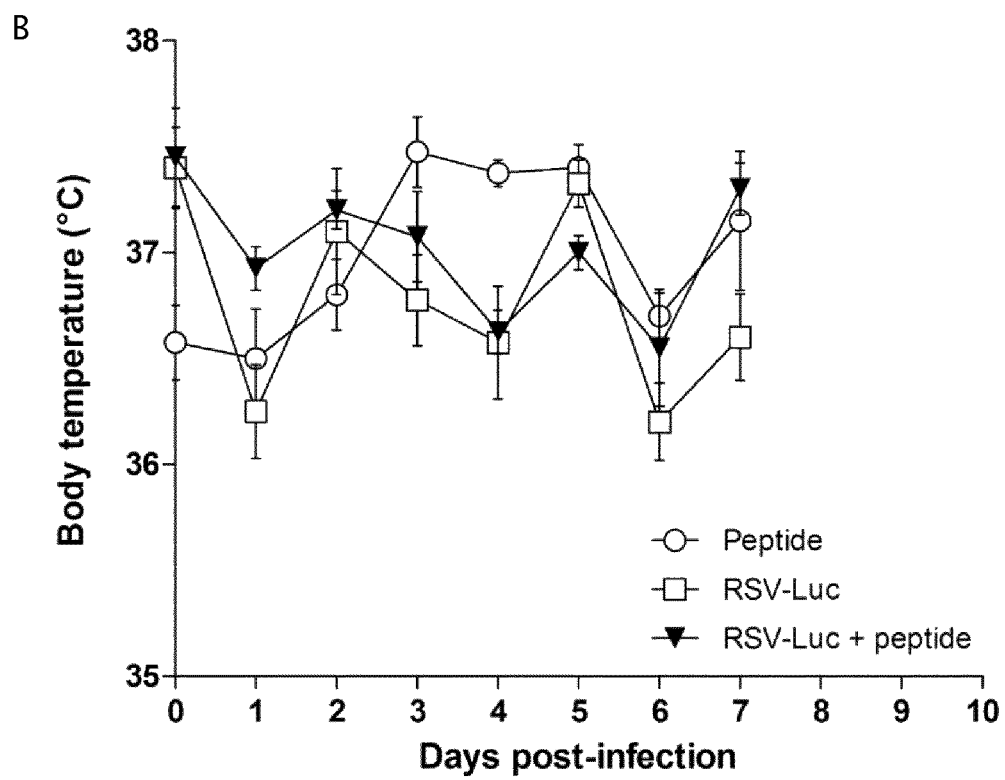
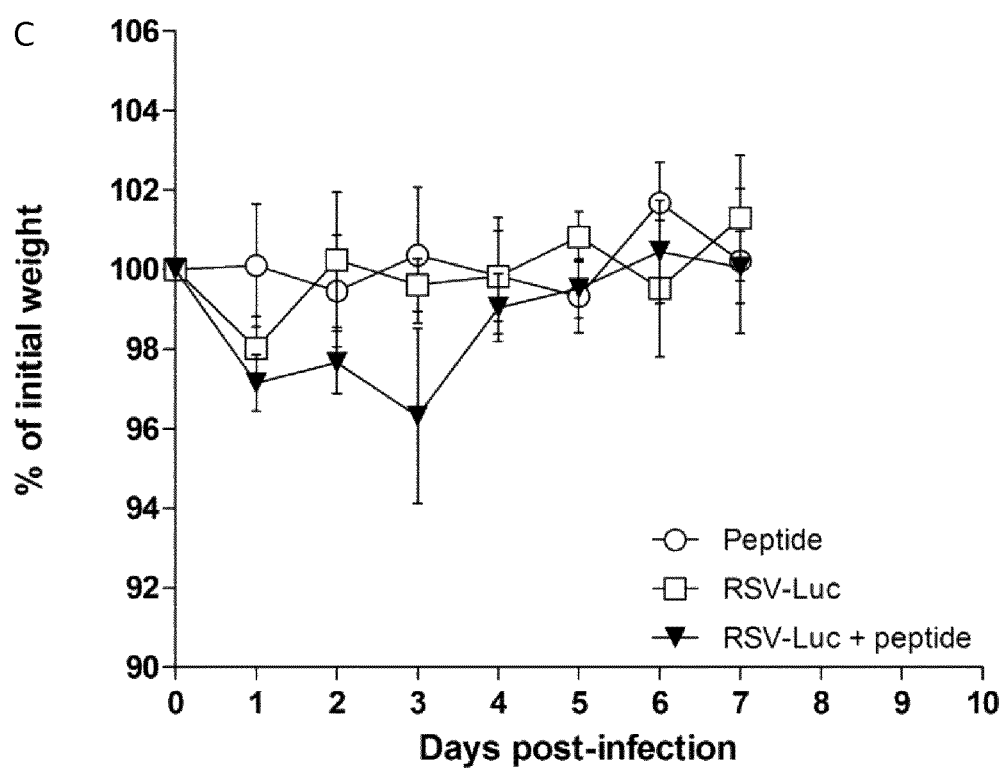

RESPIRATORY SYNCYTIAL VIRUS (RSV) REPLICATION INHIBITORS

CROSS-REFERENCE TO RELATED APPLICATIONS

This application is the U.S. national stage application of International Patent Application No. PCT/EP2015/054930, filed Mar. 10, 2015 which claims the benefit of U.S. Provisional Patent Application Nos. 61/950,488, filed Mar. 10, 2014 and 62/077,410, filed Nov. 10, 2014.

The Sequence Listing for this application is labeled "Seq-List.txt" which was created on Sep. 8, 2016 and is 25 KB. The entire content of the sequence listing is incorporated herein by reference in its entirety.

FIELD OF THE INVENTION

The invention provides polypeptides interacting with the binding of the RSV phosphoprotein P with the RSV nucleoprotein N and methods of using such polypeptides in the treatment and/or prevention of RSV infection.

BACKGROUND OF THE INVENTION

Lower respiratory infection is one of the leading causes of human death worldwide, and is the most important cause of mortality in infants. Among the pathogens responsible for these infections, human respiratory syncytial virus (RSV) accounts for approximately 20% of all lower respiratory infections in infants. The global incidence of infant mortality due to RSV is the highest in developing countries, and though it is much lower in developed countries, it is a high burden on the health care systems because of the large number of children that must be hospitalized. RSV can also cause fatal respiratory tract infections in fragile or immune-compromised individuals. Recently, RSV has been recognized as a significant cause of severe respiratory infections in the elderly. In a study performed in the US, the mortality rates were found to be higher in the elderly than in the children (Thompson et al., 2003). No vaccine is presently available against RSV, even if many trials have been done. Due to the immunopathological component of the symptoms, immunization with this virus is challenging, especially in the very young population. Treatment options are limited to the prophylactic treatment of at-risk infants with the mAb palivizumab (Synagis®) and to controversial therapeutic intervention with the nucleoside analog ribavirin (Rebetol®) (Collins and Melero, 2011).

The RSV replication machinery has been the focus of some drug discovery research in the field of siRNA and small molecules. As for all paramyxoviruses, RSV uses a helical nucleocapsid containing the nucleoprotein N bound to genomic RNA, the polymerase cofactor P, the viral polymerase L and M2-1 matrix protein to modulate transcription and replication. Whereas N, P and L are sufficient to mediate viral replication, the transcriptional activity requires the M2-1 protein functioning as a processivity polymerase co-factor. The protein P plays a central role in both processes. First, P functions as a chaperone by binding to freshly synthesized nucleoprotein thereby maintaining N in a RNA unbound form, named $N^O$. This $N^O$-P complex is required for efficient and specific encapsidation of the viral genome and antigenome by N. Second, P mediates specific recognition of the viral nucleocapsid by the L polymerase, to initiate viral transcription and replication (Mason et al., 2003; Tran et al., 2009). P is a phosphoprotein of 241 aa, which has been previously characterized (Castagné et al., 2004). Except for the central domain which mediates oligomerization, the P protein is poorly structured in its N-terminal (residues 1-103) and C-terminal (200-241) regions. Antiviral approaches aimed at disrupting viral protein-protein interactions are emerging as a viable strategy (Castel et al., 2009; Wunderlich et al., 2011). However, all these strategies rely on native peptides that are known to have important drawbacks.

Therefore, new and improved strategies for the treatment and/or prevention of RSV infection are still required.

SUMMARY OF THE INVENTION

The invention provides a polypeptide that interacts or interferes with the binding of the RSV nucleoprotein N with the RSV phosphoprotein P by disrupting, impairing and/or displacing the $N^O$-P interaction, wherein said polypeptide consists of an internally cross-linked polypeptide.

Further objects of the present invention are to provide a pharmaceutical composition comprising a pharmaceutically acceptable salt of at least one polypeptide of the invention as well as their use in the treatment and/or prevention of a RSV infection.

Also provided is a method of treating and/or preventing a RSV infection comprising administering an effective amount of at least one polypeptide of the invention.

Further provided is an inhaler comprising an effective amount of at least one polypeptide of the invention, or of pharmaceutically acceptable salt of a polypeptide of the invention, or of pharmaceutical composition of the invention, and a pharmaceutically acceptable propellant.

BRIEF DESCRIPTION OF THE FIGURES

FIG. 2: Results overview of the alanine scanning mutagenesis of P[1-40]. Amino-acid sequence of P[1-40]. Residues of the predicted mir motif (predicted domain of interaction with $N^O$) are highlighted in a box. The location of the predicted α-helix is indicated by a grey rectangle below the sequence. The Ala-mutants are listed in the left-hand column. Effect of mutations with respect to wild-type P on the activity of the polymerase, the interaction between recombinant GST-P[1-40] mutants and $N^{mono}$, and the affinity of recombinant $N^{mono}$ for GST-P[1-40] mutants calculated by SPR. The residues identified as critical for both the polymerase activity in cells and the interaction between $N^{mono}$ and GST-P mutants in biochemical assays are highlighted in grey in the sequence.

FIGS. 6A-6C: Stapled peptides used in this study. A. Single stapled peptides of P(11-30) designed on the basis of the α-helical wheel representation depicted in FIG. 4A. S5 refers to S-pentenyl-alanine, R5 refers to R-pentenyl-alanine, and R8 refers to R-octenyl-alanine. The light gray area codes for the residues that have been selected for modification with unnatural amino-acids on the hydrophilic side of the helix. HEVS 128 and HEVS 129 are negative controls where stapling have been performed on the hydrophobic face of the peptides; these peptides should not be able to interfere with the $N^0$-P interaction. B. Doubled and stitched peptides designed from HEVS 77, 78 and 79. C. N-terminal extension of HEVS 77 into single and double stapled peptides.

FIGS. 10A-10C: In vivo luminescence of rHRSV-Luc-infected mice. A. Comparative time course of bioluminescence between HEVS 124 and mock-treated mice. Each data point represents mean±s.e.m. (n=4). The statistical significance of differences was calculated using the Student's t-test. B-C. Time course of body temperature (up) and body-weight (down) of mice mock-infected or infected with $6.10^4$ PFU of rHRSV-Luc.

DESCRIPTION

Figure 1A:
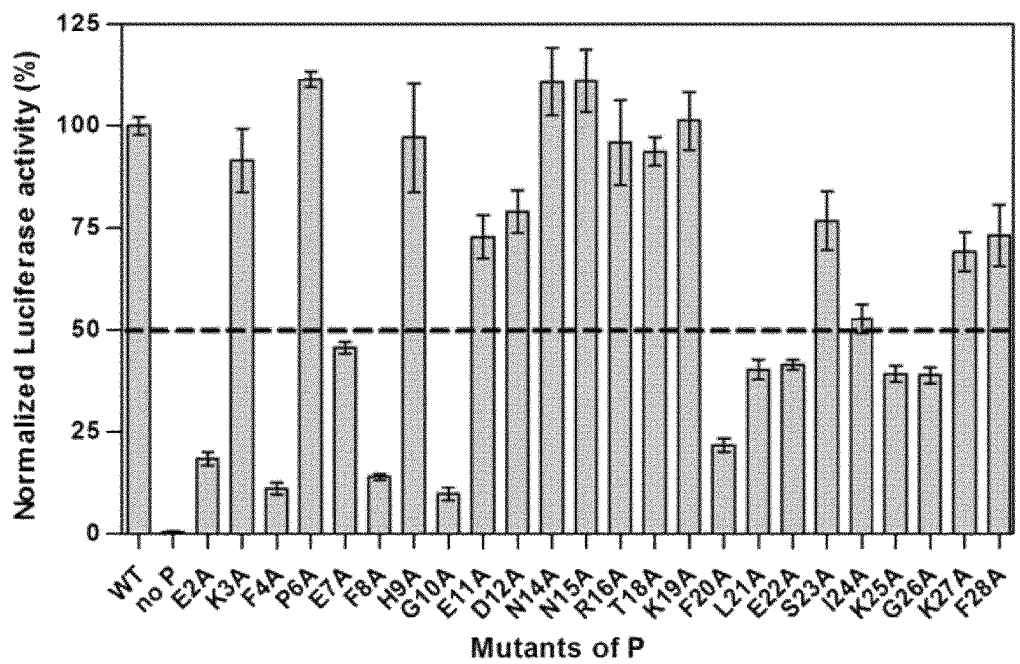
FIGS. 1A-1B: Identification of N-terminal residues of P critical for the interaction with the monomeric N. A. Effect of alanine scanning mutagenesis of P[1-28] on the polymerase complex activity in the minigenome assay. BSRT7/5 cells were transfected at 37° C. with plasmids encoding the WT N, M2-1 and L proteins, the pM/Luc replicon, and WT or mutant P proteins, together with pCMV-βGal for transfection standardization. Viral RNA synthesis was quantified by measuring the luciferase activity after cell lysis 24 h after transfection. Each luciferase minigenome activity value was normalized based on β-galactosidase expression and is the average of three independent experiments performed in triplicate. Error bars represent standard deviations, which were calculated based on three independent experiments performed in triplicate. B. GST-pull down assay. GST-P[1-40] fusion proteins (wild type or mutants E2A to F28A) were co-expressed with recombinant the monomeric N ($N^{mono}$) protein, and the resulting complexes were pull-downed on agarose beads using the GST tag. The interaction of $N^{mono}$ with P[1-40] mutants was analyzed by SDS-PAGE.

The present invention relates to a polypeptide that interacts or interferes with the binding of the RSV monomeric nucleoprotein N)($N^0$ with the RSV phosphoprotein P by disrupting, impairing and/or displacing the $N^0$-P interaction, wherein said polypeptide consists of an internally cross-linked polypeptide.

Alternatively, the polypeptide of the invention may be modified at the hydrophilic face of the predicted helix P(11-30), for example, from the list comprising Asn15, Lys16, Thr18, Lys19, Glu22, Ser23, Gly26, Lys27, Ala29, and Ser30, or at the hydrophilic face of putative helix P(2-19), for example, from the list comprising Glu2, Ala5, Pro6, His9, Asp12, Ala13, Lys16.

In some instances, the polypeptide of the invention comprises non-contiguous amino acids on the hydrophobic, interacting face of i) the helix P(11-30) consisting of the following amino acids: Ala13, Asn 14, Ala17, Phe20, Leu21, Ile24, Lys 25, and Phe28, and ii) the helix P(2-19) consisting of the following amino acids: Lys3, Phe4, Glu7, Phe8, Gly10, Glu11, Asn14, Asn15, Ala17, Thr18, Lys19.

Preferably, or alternatively, the polypeptide of the invention has a reinforced or stabilized alpha helical secondary structure. Most preferably the polypeptide of the invention consists of an internally cross-linked polypeptide.

Even more preferably, the internally cross-linked polypeptide comprises the amino acid sequence (SEQ ID No. 1)
$A_1$ $A_2$ $A_3$ $A_4$ $A_5$ $A_6$ $A_7$ $A_8$ $A_9$ $A_{10}$ $A_{11}$ $A_{12}$ $A_{13}$ $A_{14}$ $A_{15}$ $A_{16}$ $A_{17}$ $A_{18}$ $A_{19}$ $A_{20}$ $A_{21}$ $A_{22}$ $A_{23}$ $A_{24}$ $A_{25}$ $A_{26}$ $A_{27}$ $A_{28}$ $A_{29}$ $A_{30}$ $A_{31}$ $A_{32}$ $A_{33}$ $A_{34}$ $A_{35}$ $A_{36}$ $A_{37}$ $A_{38}$ $A_{39}$ $A_{40}$ wherein $A_1$ is Met, $A_2$ is Glu, or any polar negatively charged amino acid, and their amides, $A_3$ is Lys, or any polar positively charged amino acid, $A_4$ is Phe, or any large aromatic amino acid, $A_5$ is Ala, or a conservative amino acid substitution Gly, Val, Leu, Ile or any nonpolar amino acid, $A_6$ is Pro, or any nonpolar amino acid, $A_7$ is Glu, or any polar negatively charged amino acid, and their amides, $A_8$ is Phe, or any large aromatic amino acid, $A_9$ is His, or any polar positively charged amino acid, $A_{10}$ is Gly, or any small aliphatic, nonpolar or slightly polar amino acid, $A_{11}$ is Glu, or any polar negatively charged amino acid, and their amides, $A_{12}$ is Asp, or any polar, negatively charged amino acid and their amides, $A_{13}$ is Ala, or a conservative amino acid substitution Gly, Val, Leu, Ile or any nonpolar amino acid, $A_{14}$ is Asn, or any polar, negatively charged amino acid and their amides, $A_{15}$ is Asn, or any polar negatively charged amino acid and their amides, $A_{16}$ is Lys, or any polar positively charged amino acid, $A_{17}$ is Ala, or a conservative amino acid substitution Gly, Val, Leu, Ile or any nonpolar amino acid,
$A_{18}$ is Thr, or any small aliphatic, nonpolar or slightly polar amino acid,
$A_{19}$ is Lys, or any polar positively charged amino acid,
$A_{20}$ is Phe, or any large aromatic amino acid,
$A_{21}$ is Leu, or a conservative amino acid substitution Gly, Val, Ile or any nonpolar amino acid,
$A_{22}$ is Glu, or any polar negatively charged amino acid, and their amides,
$A_{23}$ is Ser, or any small aliphatic, nonpolar or slightly polar amino acid,
$A_{24}$ is Ile, or a conservative amino acid substitution Gly, Val, Leu or any nonpolar amino acid,
$A_{25}$ is Lys, or any polar positively charged amino acid,
$A_{26}$ is Gly or any small aliphatic, nonpolar or slightly polar amino acid,
$A_{27}$ is Lys, or any polar positively charged amino acid,
$A_{28}$ is Phe, or a conservative amino-acid substitution Tyr, Trp, His or any nonpolar amino acid,
$A_{29}$ is Ala, or a conservative amino acid substitution Gly, Val, Leu, Ile or any nonpolar amino acid,
$A_{30}$ is Ser, or any small aliphatic, nonpolar or slightly polar amino acid,
$A_{31}$ is Ser, or Pro, or any small aliphatic, nonpolar or slightly polar amino acid,
$A_{32}$ is Lys, or any polar positively charged amino acid,
$A_{33}$ is Asp, or any polar, negatively charged amino acid and their amides,
$A_{34}$ is Pro, or Ser, or any small aliphatic, nonpolar or slightly polar residues,
$A_{35}$ is Lys, or any polar positively charged amino acid,
$A_{36}$ is Lys, or any polar positively charged amino acid,
$A_{37}$ is Lys, or any polar positively charged amino acid,
$A_{38}$ is Asp, or any polar, negatively charged amino acid and their amides,
$A_{39}$ is Ser, or any small aliphatic, nonpolar or slightly polar amino acid,
$A_{40}$ is Ile, or a conservative amino acid substitution Gly, Arg, Val, Leu or any nonpolar amino acid,
a biologically active fragment of said amino sequence, a variant of said sequence, and wherein the side chains of two amino acids separated by two, three or six amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches.

As used herein, I) small aliphatic, nonpolar or slightly polar amino acids are selected from the group comprising Ala, Ser, Thr, Pro, and Gly;
II) Polar, positively charged amino acids are selected from the group comprising His, Arg, and Lys;
III) Polar, negatively charged amino acids are selected form the group comprising Asp, Glu, and their amides: Asn, Gln;
IV) Large, aromatic amino acids are selected from the group comprising Phe, Tyr, Trp,
V) Large, aliphatic, nonpolar amino acids are selected from the group comprising Met, Leu, Ile, Val, and Cys;
VI) beta-branched side chains amino acids are selected from the group comprising Thr, Val, Ile and Leu;
VII) non polar side chains amino acids are selected from the group comprising Ala, Val, Leu, Ile, Pro, Phe, Met, Trp.

As used herein, "peptide" or "polypeptide" comprises a polymer of amino acid residues linked together by peptide (amide) bonds. The term(s), as used herein, refers to proteins, polypeptides, and peptides of any size, structure, or function. Typically, a peptide or polypeptide will be at least three amino acids long. A peptide or polypeptide may refer to an individual protein or a collection of proteins. In some instances, peptides can include only natural amino acids, although non-natural amino acids (i.e., compounds that do not occur in nature but that can be incorporated into a polypeptide chain) and/or amino acid analogs that are known in the art may alternatively be employed. The peptide of the present invention (e.g., amino acids, peptides and proteins) may exist in particular geometric or stereoisomeric forms. The present invention contemplates all such compounds, including cis- and trans-isomers, R- and S-enantiomers, diastereomers, the racemic mixtures thereof, and other mixtures thereof, as falling within the scope of the invention.

A peptide or polypeptide of the invention may be naturally occurring, recombinant, or synthetic, or any combination thereof.

The peptides of this invention can be made by chemical synthesis methods, which are well known to the ordinarily skilled artisan. Hence, peptides can be synthesized using the automated Merrifield techniques of solid phase synthesis with the a-N $H_2$ protected by either t-Boc or Fmoc chemistry using side chain protected amino acids. Alternatively, peptides can be synthesized in solution.

One means of making the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc or the t-Boc group, which is stable in acid or in base, but removable by base or by acid, respectively. Any side chain functional groups are protected with base or acid stable, acid or base labile groups, respectively.

Longer peptides could be made by conjoining individual synthetic peptides using native chemical ligation.

The peptides can be made in a high-throughput, combinatorial fashion, e.g., using a high-throughput multiple channel combinatorial synthesizer available from Advanced Chemtech.

It is to be understood that some non-natural or non-conventional amino acids may also be suitable replacements for the naturally occurring amino acids. One or more of the amino acids in a peptide or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification such as bioisosteres (e.g. phosphorylation of Tyr), etc. Examples of modified, non-conventional or non-natural amino acids can be selected among the non-limited group of Table 1 of WO2004/0099238 (which disclosure is incorporated herein):

TABLE 1

| Non-conventional amino acid | Code | Non-conventional amino acid | Code |
|---|---|---|---|
| L-α-aminobutyric acid | Abu | L-α-methylhistidine | Mhis |
| α-amino-α-methylbutyrate | Mgabu | L-α-methylisoleucine | Mile |

TABLE 1-continued

| Non-conventional amino acid | Code | Non-conventional amino acid | Code |
|---|---|---|---|
| aminocyclopropane-carboxylate | Cpro | L-α-methylleucine | Mleu |
|  |  | L-α-methylmethionine | Mmet |
| aminoisobutyric acid | Aib | L-α-methylnorvaline | Mnva |
| aminonorbornyl-carboxylate | Norb | L-α-methylphenylalanine | Mphe |
|  |  | L-α-methylserine | Mser |
| cyclohexylalanine | Chexa | L-α-methyltryptophan | Mtrp |
| cyclopentylalanine | Cpen | L-α-methylvaline | Mval |
| D-alanine | DAla | N-(N-(2,2-diphenylethyl) carbamylmethylglycine | Nnbhm |
| D-arginine | DArg |  |  |
| D-asparagine | DAsn | 1-carboxy-1-(2,2-diphenyl-ethylamino)cyclopropane | Nmbc |
| D-aspartic acid | DAsp |  |  |
| D-cysteine | DCys | L-N-methylalanine | Nmala |
| D-glutamine | DGln | L-N-methylarginine | Nmarg |
| D-glutamic acid | DGlu | L-N-methylaspartic acid | Nmasp |
| D-histidine | DHis | L-N-methylcysteine | Nmcys |
| D-isoleucine | DIle | L-N-methylglutamine | Nmgln |
| D-leucine | DLeu | L-N-methylglutamic acid | Nmglu |
| D-lysine | DLys | L-N-methylhistidine | Nmhis |
| D-methionine | DMet | L-N-methylisolleucine | Nmile |
| D-ornithine | DOrn | L-N-methylleucine | Nmleu |
| D-phenylalanine | DPhe | L-N-methyllysine | Nmlys |
| D-proline | DPro | L-N-methylmethionine | Nmmet |
| D-serine | DSer | L-N-methylnorleucine | Nmnle |
| D-threonine | DThr | L-N-methylnorvaline | Nmnva |
| D-tryptophan | DTrp | L-N-methylornithine | Nmorn |
| D-tyrosine | DTyr | L-N-methylphenylalanine | Nmphe |
| D-valine | DVal | L-N-methylproline | Nmpro |
| D-α-methylalanine | DMala | L-N-methylserine | Nmser |
| D-α-methylarginine | DMarg | L-N-methylthreonine | Nmthr |
| D-α-methylasparagine | DMasn | L-N-methyltryptophan | Nmtrp |
| D-α-methylaspartate | DMasp | L-N-methyltyrosine | Nmtyr |
| D-α-methylcysteine | DMcys | L-N-methylvaline | Nmval |
| D-α-methylglutamine | DMgln | L-N-methylethylglycine | Nmetg |
| D-α-methylhistidine | DMhis | L-N-methyl-t-butylglycine | Nmtbug |
| D-α-methylisoleucine | DMile | L-norleucine | Nle |
| D-α-methylleucine | DMleu | L-norvaline | Nva |
| D-α-methyllysine | DMlys | α-methyl-aminoisobutyrate | Maib |
| D-α-methylmethionine | DMmet | α-methyl-γ-aminobutyrate | Mgabu |
| D-α-methylornithine | DMorn | α-methylcyclohexylalanine | Mchexa |
| D-α-methylphenylalanine | DMphe | α-methylcyclopentylalanine | Mcpen |
| D-α-methylproline | DMpro | α-methyl-α-napthylalanine | Manap |
| D-α-methylserine | DMser | α-methylpenicillamine | Mpen |
| D-α-methylthreonine | DMthr | N-(4-aminobutyl)glycine | Nglu |
| D-α-methyltryptophan | DMtrp | N-(2-aminoethyl)glycine | Naeg |
| D-α-methyltyrosine | DMty | N-(3-aminopropyl)glycine | Norn |
| D-α-methylvaline | DMval | N-amino-α-methylbutyrate | Nmaabu |
| D-N-methylalanine | DNmala | α-napthylalanine | Anap |
| D-N-methylarginine | DNmarg | N-benzylglycine | Nphe |
| D-N-methylasparagine | DNmasn | N-(2-carbamylethyl)glycine | Ngln |
| D-N-methylaspartate | DNmasp | N-(carbamylmethyl)glycine | Nasn |
| D-N-methylcysteine | DNmcys | N-(2-carboxyethyl)glycine | Nglu |
| D-N-methylglutamine | DNmgln | N-(carboxymethyl)glycine | Nasp |
| (-carboxyglutamate | Gla | N-cyclobutylglycine | Ncbut |
| 4-hydroxyproline | Hyp | N-cyclodecylglycine | Ncdec |
| 5-hydroxylsine | Hlys | N-cylcododecylglycine | Ncdod |
| 2-aminobenzoyl (anthraniloyl) | Abz | N-cyclooctylglycine | Ncoct |
|  |  | N-cyclopropylglycine | Ncpro |
| Cyclohexylalanine | Cha | N-cycloundecylglycine | Ncund |
| Phenylglycine | Phg | N-(2,2-diphenylethyl)glycine | Nbhm |
| 4-phenyl-phenylalanine | Bib | N-(3,3-diphenylpropyl)glycine | Nbhe |
| L-pyroglutamic acid | pGlu | N-(1-hydroxyethyl)glycine | Nthr |
| L-Citrulline | Cit | N-(hydroxyethyl)glycine | Nser |
| L-1,2,3,4-tetrahydroiso-quinoline-3-carboxylic acid | Tic | N-(imidazolylethyl))glycine | Nhis |
|  |  | N-(3-indolylyethyl)glycine | Nhtrp |
| L-Pipecolic acid (homo proline) | Pip | N-methyl-γ-aminobutyrate | Nmgabu |
|  |  | D-N-methylmethionine | Dnmmet |
| L-homoleucine | Hle | N-methylcyclopentylalanine | Nmcpen |
| L-Lysine (dimethyl) | DMK | D-N-meththylphenylalanine | Dnmphe |
| L-Naphthylalanine | Nal | D-N-methylproline | Dnmpro |
| L-dimethyldopa or L-dimethoxyphenylalanine | DMD | D-N-methylthreonine | Dnmthr |
|  |  | N-(1-methylethyl)glycine | Nval |
| L-thiazolidine-4-carboxylic acid | THZ | N-methyla-napthylalanine | Nmanap |
|  |  | N-methylpenicillamine | Nmpen |
| L-homotyrosine | hTyr | N-(p-hydroxyphenyl)glycine | Nhtyr |
| L-3-pyridylalanine | PYA | N-(thiomethyl)glycine | Ncys |
| L-2-furylalanine | FLA | penicillamine | Pen |
| L-histidine(benzyloxymethyl) | HBO | L-α-methylalanine | Mala |

TABLE 1-continued

| Non-conventional amino acid | Code | Non-conventional amino acid | Code |
|---|---|---|---|
| L-histidine(3-methyl) | HME | L-α-methylasparagine | Masn |
| D-N-methylglutamate | Dnmglu | L-α-methyl-t-butylglycine | Mtbug |
| D-N-methylhistidine | Dnmhis | L-methylethylglycine | Metg |
| D-N-methylisoleucine | Dnmile | L-α-methylglutamate | Mglu |
| D-N-methylleucine | Dnmleu | L-α-methylhomophenylalanine | Mhphe |
| D-N-methyllysine | Dnmlys | N-(2-methylthioethyl)glycine | Nmet |
| N-methylcyclohexylalanine | Nmchexa | L-α-methyllysine | Mlys |
| D-N-methylornithine | Dnmorn | L-α-methylnorleucine | Mnle |
| N-methylglycine | Nala | L-α-methylornithine | Morn |
| N-methylaminoisobutyrate | Nmaib | L-α-methylproline | Mpro |
| N-(1-methylpropyl)glycine | Nile | L-α-methylthreonine | Mthr |
| N-(2-methylpropyl)glycine | Nleu | L-α-methyltyrosine | Mtyr |
| D-N-methyltryptophan | Dnmtrp | L-N-methylhomophenylalani | Nmhphe |
| D-N-methyltyrosine | Dnmtyr | N-(N-(3,3-diphenylpropyl) | Nnbhe |
| D-N-methylvaline | Dnmval | carbamylmethylglycine | |
| L-t-butylglycine | Tbug | O-methyl-L-serine | Omser |
| L-ethylglycine | Etg | O-methyl-L-homoserine | Omhser |
| L-homophenylalanine | Hphe | O-methyl-L-tyrosine | MeY |
| L-α-methylarginine | Marg | γ-aminobutyric acid | Gabu |
| L-α-methylaspartate | Masp | O-methyl-L-homotyrosine | Omhtyr |
| L-α-methylcysteine | Mcys | L-Ǝ-homolysine | BHK |
| L-α-methylglutamine | Mgln | L-ornithine | Orn |
| N-cycloheptylglycine | Nchep | N-cyclohexylglycine | Nchex |
| N-(3-guanidinopropyl)glycine | Narg | D-N-methylserine | DNmser |

Alternatively, or in addition, peptide bonds can be replaced, e.g., to increase physiological stability of the peptide of the invention, by: a reduced amide bond (NH—CH$_2$); a thiomethylene bond (S—CH$_2$ or CH$_2$—S); an oxomethylene bond (0-CH$_2$ or CH$_2$-0); an ethylene bond (CH$_2$—CH$_2$); a thioamide bond (C(S)—NH); a trans-olefin bond (CH═CH); a fluoro substituted trans-olefin bond (CF═CH); a ketomethylene bond (C(O)—CHR) or CHR—C(O) wherein R is H or CH$_3$; a fluoro-ketomethylene bond (C(O)—CFR or CFR—C(O) wherein R is H or F or CH$_3$; a methyl amide bond C(O)—N—CH$_3$—; and a beta-amino acid.

The present invention also considers a "biologically active fragment" or a portion of the polypeptide, which refers to a sequence containing less amino acids in length than the sequence of the polypeptide. This sequence can be used as long as it exhibits essentially the same properties or biological activity as the native sequence from which it derives, i.e. interacting with the binding of the RSV nucleoprotein N with the RSV phosphoprotein P. Generally, the biologically active fragment of the polypeptide of the invention inherently possesses or can be induced to have one or more alpha helical secondary structure(s).

Preferably this biologically active fragment sequence contains less than 99%, preferably less than 85%, in particular less than 80% and more particularly less than 70% of amino acids in length than the respective sequence of the peptide of the invention. Preferably also these biologically active fragment sequences contain at least 8, at least 15, at least 20, at least 25, at least 30, at least 35 contiguous amino acids in length in common with the sequence of the peptide of the invention.

In some instances, the biologically active fragment of the internally cross-linked polypeptide has the following amino acid sequence: $A_{11} A_{12} A_{13} A_{14} A_{15} A_{16} A_{17} A_{18} A_{19} A_{20} A_{21} A_{22} A_{23} A_{24} A_{25} A_{26} A_{27} A_{26} A_{29} A_{30}$ (SEQ ID NO: 2) wherein $A_{11}$ is Glu, or any polar negatively charged amino acid, and their amides, $A_{12}$ is Asp, or any polar, negatively charged amino acid and their amides, $A_{13}$ is Ala, or a conservative amino acid substitution Gly, Val, Leu, Ile or any nonpolar amino acid, $A_{14}$ is Asn, or any polar, negatively charged amino acid and their amides, $A_{15}$ is Asn, or any polar, negatively charged amino acid and their amides, $A_{16}$ is Lys, or any polar positively charged amino acid, $A_{17}$ is Ala, or a conservative amino acid substitution Gly, Val, Leu, Ile or any nonpolar amino acid, $A_{18}$ is Thr, or any small aliphatic, nonpolar or slightly polar amino acid, $A_{19}$ is Lys, or any polar positively charged amino acid, $A_{20}$ is Phe, or any large aromatic amino acid, $A_{21}$ is Leu, or a conservative amino acid substitution Gly, Arg, Val, Ile or any nonpolar amino acid, $A_{22}$ is Glu, or any polar negatively charged amino acid, and their amides, $A_{23}$ is Ser, or any small aliphatic, nonpolar or slightly polar amino acid, $A_{24}$ is Ile, or a conservative amino acid substitution Gly, Arg, Val, Leu or any nonpolar amino acid, $A_{25}$ is Lys, or any polar positively charged amino acid, $A_{26}$ is Gly or any small aliphatic, nonpolar or slightly polar amino acid, $A_{27}$ is Lys, or any polar positively charged amino acid, $A_{28}$ is Phe, or a conservative amino-acid substitution Tyr, Trp, His or any nonpolar amino acid, $A_{29}$ is Ala, or a conservative amino acid substitution Gly, Val, Leu, Ile or any nonpolar amino acid, $A_{30}$ is Ser, or any small aliphatic, nonpolar or slightly polar amino acid, or a variant of said sequence, and wherein the side chains of two amino acids separated by two, three or six amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches.

In some other instances, the biologically active fragment of the internally cross-linked polypeptide has the following amino acid sequence: $A_7 A_8 A_9 A_{10} A_{11} A_{12} A_{13} A_{14} A_{15} A_{16} A_{17} A_{18} A_{19} A_{20} A_{21} A_{22} A_{23} A_{24} A_{25} A_{26} A_{27} A_{28} A_{29} A_{30}$ (SEQ ID NO: 3) wherein $A_7$ is Glu, or any polar negatively charged amino acid, and their amides,
$A_8$ is Phe, or any large aromatic amino acid,
$A_9$ is His, or any polar positively charged amino acid,
$A_{10}$ is Gly, or any small aliphatic, nonpolar or slightly polar amino acid,
$A_{11}$ is Glu, or any polar negatively charged amino acid, and their amides,
$A_{12}$ is Asp, or any polar, negatively charged amino acid and their amides,
$A_{13}$ is Ala, or a conservative amino acid substitution Gly, Val, Leu, Ile or any nonpolar amino acid,
$A_{14}$ is Asn, or any polar, negatively charged amino acid and their amides,
$A_{15}$ is Asn, or any polar, negatively charged amino acid and their amides,
$A_{16}$ is Lys, or any polar positively charged amino acid,
$A_{17}$ is Ala, or a conservative amino acid substitution Gly, Val, Leu, Ile or any nonpolar amino acid,
$A_{18}$ is Thr, or any small aliphatic, nonpolar or slightly polar amino acid,
$A_{19}$ is Lys, or any polar positively charged amino acid,
$A_{20}$ is Phe, or any large aromatic amino acid,
$A_{21}$ is Leu, or a conservative amino acid substitution Gly, Arg, Val, Ile or any nonpolar amino acid,
$A_{22}$ is Glu, or any polar negatively charged amino acid, and their amides,
$A_{23}$ is Ser, or any small aliphatic, nonpolar or slightly polar amino acid,
$A_{24}$ is Ile, or a conservative amino acid substitution Gly, Arg, Val, Leu or any nonpolar amino acid,
$A_{25}$ is Lys, or any polar positively charged amino acid,
$A_{26}$ is Gly or any small aliphatic, nonpolar or slightly polar amino acid,
$A_{27}$ is Lys, or any polar positively charged amino acid,
$A_{28}$ is Phe, or a conservative amino-acid substitution Tyr, Trp, His or any nonpolar amino acid,
$A_{29}$ is Ala, or a conservative amino acid substitution Gly, Val, Leu, Ile or any nonpolar amino acid,
$A_{30}$ is Ser, or any small aliphatic, nonpolar or slightly polar amino acid,
or a variant of said sequence, and wherein the side chains of two amino acids separated by two, three or six amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches.

Preferably, the biologically active fragment of the internally cross-linked polypeptide consists in, or comprises, an amino acid sequence selected from the group comprising SEQ ID NO: 5 (HEVS 74), SEQ ID NO: 6 (HEVS 75), SEQ ID NO: 7 (HEVS 76), SEQ ID NO: 8 (HEVS 77), SEQ ID NO: 9 (HEVS 78), SEQ ID NO: 10 (HEVS 79), SEQ ID NO: 11 (HEVS 108), SEQ ID NO: 12 (HEVS 109), SEQ ID NO: 13 (HEVS 110), SEQ ID NO: 14 (HEVS 111), SEQ ID NO: 15 (HEVS 112), SEQ ID NO: 16 (HEVS 113), SEQ ID NO: 17 (HEVS 114), SEQ ID NO: 18 (HEVS 115), SEQ ID NO: 19 (HEVS 116), SEQ ID NO: 20 (HEVS 117), SEQ ID NO: 21 (HEVS 118), SEQ ID NO: 22 (HEVS 120), SEQ ID NO: 23 (HEVS 121), SEQ ID NO: 24 (HEVS 122), SEQ ID NO: 25 (HEVS 123), SEQ ID NO: 26 (HEVS 124), SEQ ID NO: 27 (HEVS 125), and SEQ ID NO: 28 (HEVS 126).

The present invention further refers to a conservative variant of the polypeptide of the invention. This conservative variant refers to polypeptides having amino acid sequences that differ to some extent from the native sequence polypeptide that is amino acid sequences that vary from the native 3D sequence whereby one or more amino acids (e.g., 1, 2, 3, 4, 5, 6, 7, 8, 9, 10, 11, 12, 13, 14, 15, 16, 17, 18) are substituted by another one. The variants can occur naturally (e.g. polymorphism) or can be synthesized. Variants possess substitutions, deletions, and/or insertions at certain positions within the amino acid sequence of the native amino acid sequence. Amino acid substitutions are herein defined as exchanges within one of the following five groups:

I. Small aliphatic, nonpolar or slightly polar residues: Ala, Ser, Thr, Pro, Gly
II. Polar, positively charged residues: His, Arg, Lys
III. Polar, negatively charged residues Asp, Glu, and their amides: Asn, Gln
IV. Large, aromatic residues: Phe, Tyr, Trp
V. Large, aliphatic, nonpolar residues: Met, Leu, Ile, Val, Cys.
VI. beta-branched side chains: Thr, Val, Ile, Leu
VII. non polar side chains Ala, Val, Leu, Ile, Pro, Phe, Met, Trp Preferably the amino acid substitutions are conservative, i.e. occur within one of the above-identified group and consist of replacement with one or another amino acid residue having a similar side chain. Such conservative amino acid substitutions exist between different species as shown in Table 2 below:

TABLE 2

| RSV Human | MEKFAPEFHGEDANNRATKF LESIKGKFTSPKDPKKKDSI | SEQ ID No. 35 |
|---|---|---|
| RSVB Bovine | MEKFAPEFHGEDANTKATKF LESLKGKFTSSKDSRKKDSI | SEQ ID No. 36 |

Conservative amino acid substitutions among the species are represented as underlined type residues.

Methods of identifying amino acid conservative substitutions which do not eliminate the binding of the RSV nucleoprotein N with the RSV phosphoprotein P are well-known in the art.

Usually, the conservative variant of the polypeptide of the invention is at least 80% (e.g., 80%, 85%, 90%, 95%, 98%, 99%, or 99.50%) identical with the sequence of said peptide of the invention.

Generally, the polypeptide of the invention interacts with the binding of the RSV monomeric nucleoprotein N with the RSV phosphoprotein P. Usually said interaction inhibits the RSV viral replication by disrupting, impairing and/or displacing the $N^0$-P interaction.

Alternatively or in addition, the polypeptide as disclosed in the present invention is conjugated to an agent, which increases the accumulation of the peptide in a cell.

Such an agent can be a compound which induces receptor mediated endocytosis such as for example the membrane transferrin receptor mediated endocytosis of transferrin conjugated to therapeutic drugs (Qian Z. M. et al., "Targeted drug delivery via the transferrin receptor-mediated endocytosis pathway" Pharmacological Reviews, 54, 561, 2002) or a cell membrane permeable carrier which can be selected e.g. among the group of fatty acids such as decanoic acid, myristic acid and stearic acid, which have already been used for intracellular delivery of peptide inhibitors of protein kinase C (Ioannides C. G. et al, "Inhibition of IL-2 receptor induction and IL-2 production in the human leukemic cell line Jurkat by a novel peptide inhibitor of protein kinase C" Cell Immunol., 131, 242, 1990) and protein-tyrosine phosphatase (Kole H. K. et al., "A peptide-based protein-tyrosine phosphatase inhibitor specifically enhances insulin receptor function in intact cells" J. Biol. Chem. 271, 14302, 1996) or among peptides. Preferably, cell membrane permeable carriers are used, more preferably a cell membrane permeable carrier peptide is used.

In case the cell membrane permeable carrier is a peptide then it will preferably be a positively charged amino acid rich peptide.

Preferably such positively charged amino acid rich peptide is an arginine rich peptide. It has been shown by Futaki et al. (Futaki S. et al, "An abundant source of membrane-permeable peptides having potential as carriers for intracellular protein delivery" J. Biol. Chem., 276, 5836, 2001), that the number of arginine residues in a cell membrane permeable carrier peptide has a significant influence on the method of internalization and that there seems to be an optimal number of arginine residues for the internalization, preferably they contain more than 6 arginines, more preferably they contain 9 arginines (R9).

The peptide of the invention may be conjugated to the cell membrane permeable carrier by a spacer, such as, for example two glycine residues to allow flexibility. In this case the cell membrane permeable carrier is also preferably a peptide.

Usually, the positively charged amino acid rich peptide is selected among the non-limiting group comprising the HIV-TAT 48-57 peptide [GRKKRRQRRR, SEQ ID NO: 29], the FHV-coat 35-49 peptide [RRRRNRTRRNRRRVR, SEQ ID NO: 30], the HTLV-II Rex 4-16 peptide [TRRQRTRRAR-RNR, SEQ ID NO: 31], the NYAD-1 peptide [IT-FXDLLXYYGP, X=(S)-alpha-(2'-pentenyl)alanine), SEQ ID NO: 32], the BMV gag 7-25 peptide [KMTRAQR-RAAARRNRWTAR, SEQ ID NO: 33] and the R9 peptide [RRRRRRRRR, SEQ ID NO: 34].

Since an inherent problem with native peptides (in L-form) is degradation by natural proteases, the peptide of the invention, as well as the cell membrane peptide carrier, may comprise one or more amino acid in the L-form or in D-form, and/or in a retro-inverso isomer form. Retro-inverso peptides are prepared for peptides of known sequence as described for example by Sela and Zisman (1997). By "retro-inverso isomer" is meant an isomer of a linear peptide in which the direction of the sequence is reversed and the chirality of each amino acid residue is inverted; thus, there can be no end-group complementarity.

Alternatively, the peptide of the invention may be further conjugated to a molecule, such as a chemical entity, that leads to improved pharmacokinetics, increased half-life, of said peptide. Said chemical entity may be covalently linked to the N-terminal end, or the C-terminal end, of the amino acid sequence of said polypeptide and may be selected from the group comprising an acetyl, a fatty acid, a cholesterol, a poly-ethylene glycol (PEG), a XTEN sequence, a nuclear localization signal, nuclear export signal, an antibody, a polysaccharide and a targeting molecule. Preferably, such chemical entity is a poly-ethylene glycol (PEG).

As disclosed above, the polypeptide of the invention may include at least two modified (natural or non-natural) amino acids that together form an internal (intramolecular) cross-link (or staple), wherein the at least two modified amino acids are separated by 2 (i.e., i, i+3, shown in FIG. 5 as □), 3 (i.e., i, i+4, shown in FIG. 5 as o), or, 6 (i.e., i, i+7, shown in FIG. 5 as Δ) amino acids.

In the case of a cross-link between i and i+3 the cross-link can be a C6, C7, or C8 alkyl or alkene (e.g., a C6 alkene having a single double bond). In the case of a cross-link between i and i+4 the cross-link can be a C8 alkyl or alkene. In the case of a cross-link between i and i+7 the cross-link can be a C11, C12 or C13 alkyl or alkene (e.g., a 11 alkene having a single double bond). When the cross-link is an alkene there can be one or more double bonds.

"Peptide stapling", as used herein, is a term coined from a synthetic methodology wherein two olefin-containing side-chains (e.g., cross-linkable side chains) present in a polypeptide chain are covalently joined (e.g., "stapled together") using a ring-closing metathesis (RCM) reaction to form a cross-linked ring (Blackwell et al., 2001). As used herein, the term "peptide stapling," includes the joining of two (e.g., at least one pair of) double bond-containing side-chains, triple bond-containing side-chains, or double bond-containing and triple bond-containing side chain, which may be present in a polypeptide chain, using any number of reaction conditions and/or catalysts to facilitate such a reaction, to provide a singly "stapled" polypeptide. The term "multiply stapled" polypeptides refers to those polypeptides containing more than one individual staple, and may contain two, three, or more independent staples of various spacing and compositions. Additionally, the term "peptide stitching," as used herein, refers to multiple and tandem "stapling" events in a single polypeptide chain to provide a "stitched" (e.g., tandem or multiply stapled) polypeptide, in which two staples, for example, are linked to a common residue. Peptide stitching is disclosed in WO 2008/121767 and in WO 2010/068684, which are both hereby incorporated by reference. In some instances, staples, as used herein, can retain the unsaturated bond or can be reduced (e.g., as mentioned below in the stitching paragraph description).

While many peptide staples have all hydrocarbon cross-links, other type of crosslinks or staples can be used. For example, triazole-containing (e.g, 1, 4 triazole or 1, 5 triazole) crosslinks can be used (Kawamoto et al., 2012; WO 2010/060112 which are both hereby incorporated by reference).

To improve the cellular permeability of the peptide, the hydrocarbon cross-links can be modified by the introduction of one or more lipophilic cations such as a quaternary amine (—CH=CH—$CH_2$—$NH^+$—$CH_2$—), or into an Alloc stapled peptide (—NHCOO$CH_2$CH=CH$CH_2$—). Additionally, a Glu to Gln mutation can be introduced, and the position of an arginine can be swapped with a hydrophobic residue.

Stapling of a peptide using all-hydrocarbon cross-link has been shown to help maintain its native conformation and/or secondary structure, particularly under physiologically relevant conditions (Schafmeister et al., 2000; Walensky et al., 2004).

Stapling the polypeptide herein by an all-hydrocarbon crosslink predisposed to have an alpha-helical secondary structure can constrain the polypeptide to its native alpha-helical conformation. The constrained secondary structure may, for example, increase the peptide's resistance to proteolytic cleavage, may increase the peptide's thermal stability, may increase the peptide's hydrophobicity, may allow for better penetration of the peptide into the target cell's membrane (e.g., through an energy-dependent transport mechanism such as pinocytosis), and/or may lead to an improvement in the peptide's biological activity relative to the corresponding uncross-linked (e.g., "unstitched" or "unstapled") peptide.

Peptides herein include at least two internally cross-linked or stapled amino acids, wherein the at least two amino acids are separated by 2 (i.e., i, i+3, shown in FIG. 5 as □), 3 (i.e., i, i+4, shown in FIG. 5 as o), or 6 (i.e., i, i+7, shown in FIG. 5 as Δ) amino acids. While at least two amino acids are required to support an internal cross-link (e.g., a staple), additional pairs of internally cross-linked amino acids can be included in a peptide, e.g., to support additional internal cross-links (e.g., staples). For example peptides can include 1, 2, 3, 4, 5, or more staples. Examples of peptide staples are illustrated in FIG. 6. Cross-linked peptides (e.g., stapled and/or stitched peptides) are generally referred to herein as HEVS peptides.

Alternatively or in addition, peptides can include three internally cross-linked or stitched amino acids, e.g., yielding two staples arising from a common origin. A peptide stitch includes at least three internally cross-linked amino acids, wherein the middle of the three amino acids forms an internal cross-link (between alpha carbons) with each of the two flanking modified amino acids. The alpha carbon of the core amino acid has side chains that are internal cross-links to the alpha carbons of other amino acids in the peptide, which can be saturated or not saturated. Amino acids cross-linked to the core amino acid can be separated from the core amino acid in either direction by 2, 3, or 6 amino acids, e.g., i, i-3; i, i-4; i, i-7 (shown in FIG. 5 as ■, •, and ▼, respectively), i, i+3; i, i+4; i, i+7 (shown in FIG. 5 as □, o, and Δ, respectively), where "i" is the core amino acid). The number of amino acids on either side of the core (e.g., between the core amino acid and an amino acid cross-linked to the core) can be the same or different. Examples of such three amino acid containing peptide stitches are illustrated in FIG. 6B. In some instances, a stitch can include 3, 4, 5, or more internally cross-linked amino acids. In some instances, peptides can include 1, 2, 3, 4, 5, or more stitches.

In some examples, peptides herein can include a combination of at least one (e.g., 1, 2, 3, 4, or 5) staple and at least one (e.g., 1, 2, 3, 4, or 5) stitch.

Cross-linked peptides (e.g., stapled and/or stitched peptides) are generally referred to herein as HEVS peptides. Peptides can include cross-linked amino acids at one or more of the positions illustrated in FIG. 6B.

Figure 5:
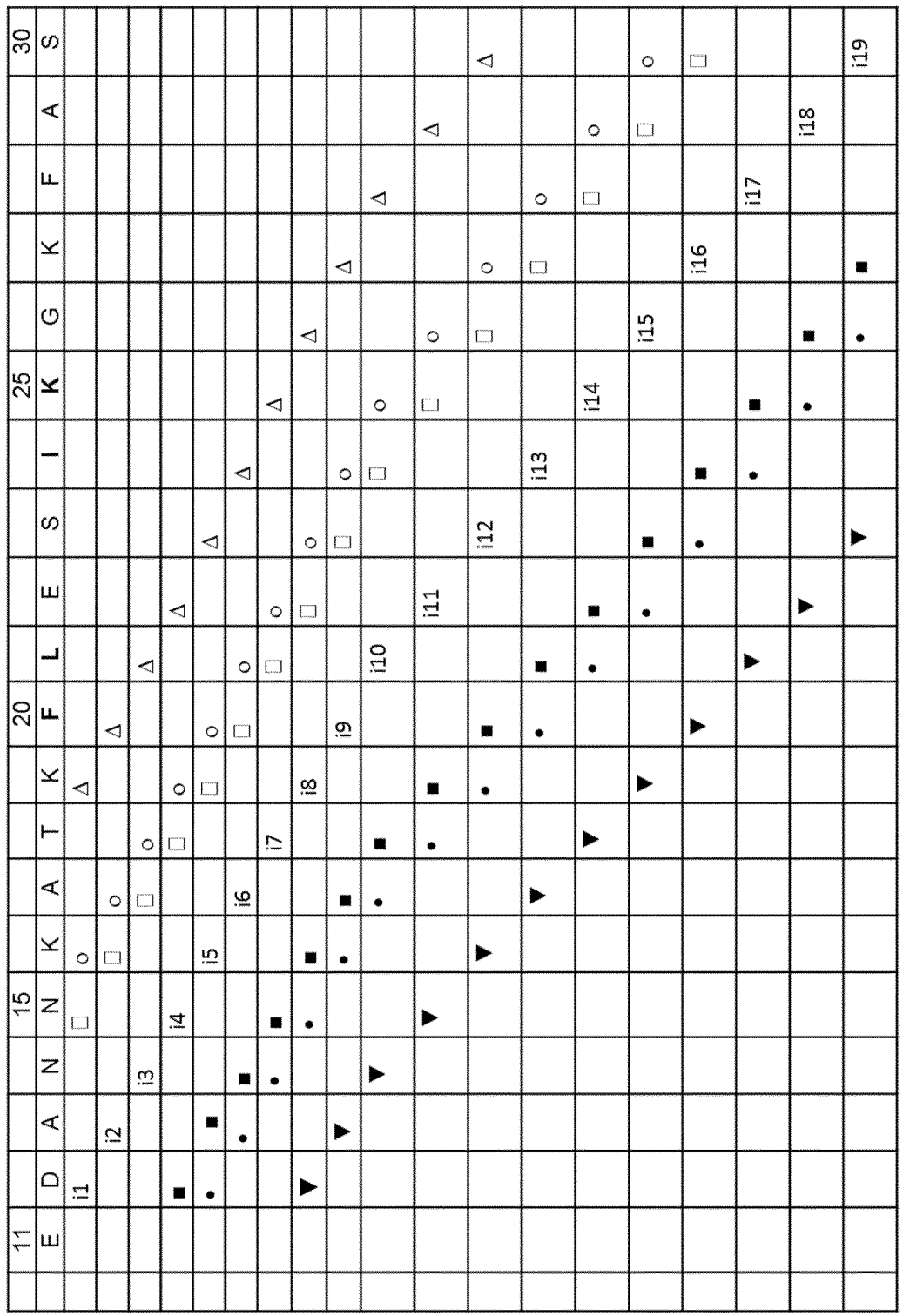
FIG. 5: Schematic representation of all possible staples in P(11-30) that can be engineered both at the hydrophilic and at the hydrophobic faces of the peptide. The residues in bold refer to the residues crucial for $N^0$-P binding. From each i position, the square corresponds to i+3, the circle to i+4 and the triangle to i+7.

In FIG. 5, positions of cross-links are indicated by symbols and the letter "i". For example, i10 (Leu21) can be linked via a i+3 staple to Ile24 or Thr18 (also called i-3) or a i+4 staple to Lys25 or Ala17 (also called i-4) or a i+7 staple to Phe28 or Asn14 (also called i-7). Of course, i10 (Leu21) could be stitched to, for example Ile24 (i+3) and Asn14 (i-7). In FIG. 5, the first row shows the amino-acid numbering of P(11-30) and the second row shows an exemplary embodiment of P(11-30), corresponding to HEVS 73 (EDANN-KATKFLESIKGKFAS, SEQ ID NO: 4).

Internal cross-links (e.g., staples and/or stitches) can be positioned on amino acids within a peptide to conserve the structural relationship of amino acids in the binding or interacting face of the peptide (e.g., to preserve the binding interface of a peptide).

Alternatively, staples can be placed on the interacting face as long as binding affinity or activity is not altered. In some embodiments, the staple or staples can be placed such that they partially or completely engage the target and enhance binding activity, as exemplified for the stapled MCL-1 BH3 helix (Stewart et al., 2010). For example, one or more of P(11-30) can be stapled or stitched to at least one other amino acid to conserve the structural relationship of amino acids in the hydrophobic interaction face shown in FIG. 4A (amino acids in the non-interacting/hydrophilic face are highlighted in FIG. 4A). Such internal cross-links can include: one or more staples; one or more stitches; and/or a combination of one or more staples with one or more stitches. In some instances, two or more amino acids located within the hydrophilic face highlighted in FIG. 4A can be cross-linked (e.g., stapled or stitched).

Referring in more details to the examples, the residues for modification with non-natural amino-acids on the hydrophilic side of the helix of the peptide of the invention (depicted in light gray area codes in FIG. 6) are selected from the non-limiting group comprising Asn15, Lys16, Lys19, Ser23, Gly26, Lys27 and Ser30. In some instances, the non-natural amino-acids are selected from the group comprising R,S-bis-pentenyl-glycine, S-pentenyl-alanine, R-pentenyl-alanine, S-octenyl-alanine and R-octenyl-alanine.

Exemplary cross-linked peptides include HEVS 74, HEVS 75, HEVS 76, HEVS 77, HEVS 78, HEVS 79, HEVS 108, HEVS 109, HEVS 110, HEVS 111, HEVS 112, HEVS 113, HEVS 114, HEVS 115, HEVS 116, HEVS 117, HEVS 118, HEVS 120, HEVS 121, HEVS 122, HEVS 123, HEVS 124, HEVS 125, and HEVS 126.

TABLE 3

| Name | SEQ ID No | Amino-acid sequence |
|---|---|---|
| HEVS 74 | 5 | EDANNKATS$_5$FLES$_5$IKGKFAS |
| HEVS 75 | 6 | EDANS$_5$KATS$_5$FLESIKGKFAS |
| HEVS 76 | 7 | DANNR$_5$ATS$_5$FLESIKGKFAS |
| HEVS 77 | 8 | EDANNR$_8$ATKFLES$_5$IKGKFAS |
| HEVS 78 | 9 | EDANNKATKFLES$_5$IKGS$_5$FAS |
| HEVS 79 | 10 | EDANNKATKFLER$_8$IKGKFAS$_5$ |
| HEVS 108 | 11 | EDANNKATR$_8$FLESIKS$_5$KFAS |
| HEVS 109 | 12 | EDANNKATKFLER$_5$IKS$_5$KFAS |
| HEVS 110 | 13 | EDANNKATKFLESIKS$_5$KFAS$_5$ |
| HEVS 111 | 14 | EDANNKATKFLESIKGR$_5$FAS$_5$ |
| HEVS 112 | 15 | EDANNKATKFLESIKR$_5$KFS$_5$S |
| HEVS 113 | 16 | EDANNKATKFLR$_8$SIKGKFS$_5$S |
| HEVS 114 | 17 | EDANNKATKFLS$_5$IKS5KFAS |
| HEVS 115 | 18 | EDANNKATR$_5$FLS$_5$SIKGKFAS |
| HEVS 116 | 19 | EDANNKAS$_5$KFLS$_5$SIKGKFAS |
| HEVS 117 | 20 | EDANR$_8$KATKFLS$_5$SIKGKFAS |
| HEVS 118 | 21 | EDANR$_5$KAS$_5$KFLESIKGKFAS |
| HEVS 120 | 22 | EDANNR$_8$ATKFLES$_5$/R$_5$IKGKFAS$_8$ |
| HEVS 121 | 23 | DANNS$_8$ATKFLES$_5$/R$_5$IKGS$_5$FAS |
| HEVS 122 | 24 | DANS$_5$KATS$_5$FLES$_5$IKGS$_5$FAS |

TABLE 3-continued

| Name | SEQ ID No | Amino-acid sequence |
|---|---|---|
| HEVS 123 | 25 | EDANS5KATS5FLER8IKGKFAS5 |
| HEVS 124 | 26 | EFHGEDANNR8ATKFLES5IKGKFAS |
| HEVS 125 | 27 | ES5HGES5ANNR8ATKFLES5IKGKFAS |
| HEVS 126 | 28 | EFR5GES5ANNR8ATKFLES5IKGKFAS |

S5/R5 refers to R,S-bis-pentenyl-glycine.
S5 refers to S-pentenyl-alanine, R5 refers to R-pentenyl-alanine, S8 refers to S-octenyl-alanine and R8 refers to R-octenyl-alanine.

In case recombinant techniques are employed to prepare a peptide in accordance with the present invention, nucleic acid sequences encoding the polypeptides are preferably used. Accordingly, the present invention also relates to a purified and isolated nucleic acid or nucleic acid sequence encoding one or more polypeptides of the invention.

With regard to the method to practice recombinant techniques, see for example, Maniatis et al. 1982, Molecular Cloning, A laboratory Manual, Cold Spring Harbor Laboratory and commercially available methods.

Accordingly the present invention also relates to a purified and isolated nucleic acid sequence encoding a peptide as described herein.

"A purified and isolated nucleic acid or nucleic acid sequence" refers to the state in which the nucleic acid sequence encoding the peptide of the invention, or nucleic acid encoding such peptide will be, in accordance with the present invention.

A purified and isolated nucleic acid or nucleic acid sequence encompassed by the present invention might be DNA, RNA, or DNA/RNA hybrid.

DNA which can be used herein is any polydeoxynucleotide sequence, including, e.g. double-stranded DNA, single-stranded DNA, double-stranded DNA wherein one or both strands are composed of two or more fragments, double-stranded DNA wherein one or both strands have an uninterrupted phosphodiester backbone, DNA containing one or more single-stranded portion(s) and one or more double-stranded portion(s), double-stranded DNA wherein the DNA strands are fully complementary, double-stranded DNA wherein the DNA strands are only partially complementary, circular DNA, covalently-closed DNA, linear DNA, covalently cross-linked DNA, cDNA, chemically-synthesized DNA, semi-synthetic DNA, biosynthetic DNA, naturally-isolated DNA, enzyme-digested DNA, sheared DNA, labeled DNA, such as radiolabeled DNA and fluorochrome-labeled DNA, DNA containing one or more non-naturally occurring species of nucleic acid.

DNA sequences that encode a peptide of the invention can be synthesized by standard chemical techniques, for example, the phosphotriester method or via automated synthesis methods and PCR methods.

The purified and isolated DNA sequence encoding a peptide according to the invention may also be produced by enzymatic techniques. Thus, restriction enzymes, which cleave nucleic acid molecules at predefined recognition sequences can be used to isolate nucleic acid sequences from larger nucleic acid molecules containing the nucleic acid sequence, such as DNA (or RNA) that codes for a peptide of the invention.

Encompassed by the present invention is also a nucleic acid in the form of a polyribonucleotide (RNA), including, e.g., single-stranded RNA, double-stranded RNA, double-stranded RNA wherein one or both strands are composed of two or more fragments, double-stranded RNA wherein one or both strands have an uninterrupted phosphodiester backbone, RNA containing one or more single-stranded portion(s) and one or more double-stranded portion(s), double-stranded RNA wherein the RNA strands are fully complementary, double-stranded RNA wherein the RNA strands are only partially complementary, covalently cross-linked RNA, enzyme-digested RNA, sheared RNA, mRNA, chemically-synthesized RNA, semi-synthetic RNA, biosynthetic RNA, naturally-isolated RNA, labeled RNA, such as radiolabeled RNA and fluorochrome-labeled RNA, RNA containing one or more non-naturally-occurring species of nucleic acid.

The present invention also includes variants of the nucleic acid sequence encoding a peptide according to the invention. These variants are nucleotide sequences that vary from the reference sequence by conservative nucleotide substitutions, whereby one or more nucleotides are substituted by another with same characteristics.

The invention also encompasses allelic variants of the sequence encoding a peptide according to the invention; that is, naturally-occurring alternative forms of the isolated and purified nucleic acid that also encode peptides that are identical, homologous or related to that encoded by the purified and isolated nucleic sequences. Alternatively, non-naturally occurring variants may be produced by mutagenesis techniques or by direct synthesis.

The aforementioned purified and isolated nucleic acid sequence encoding a peptide of the invention may further comprise a nucleotide sequence encoding a cell membrane permeable carrier peptide.

Yet another concern of the present invention is to provide an expression vector comprising at least one copy of the isolated and purified nucleic acid sequence encoding a peptide of the invention. Preferably the isolated and purified nucleic acid sequence encoding a peptide of the invention is DNA.

As used herein, "vector", "plasmid" and "expression vector" are used interchangeably, as the plasmid is the most commonly used vector form.

The vector may further comprise a nucleotide sequence encoding a cell membrane permeable carrier peptide in accordance with the invention. The choice of an expression vector depends directly, as it is well known in the art, on the desired functional properties, e.g., peptide expression and the host cell to be transformed or transfected.

Additionally, the expression vector may further comprise a promoter operably linked to the purified and isolated DNA sequence. This means that the linked isolated and purified DNA sequence encoding the peptide of the present invention is under control of a suitable regulatory sequence, such as a promoter, which allows expression, i.e. transcription and translation of the inserted isolated and purified DNA sequence.

As used herein, the term "promoter" designates any additional regulatory sequences known in the art e.g. a promoter and/or an enhancer, polyadenylation sites and splice junctions usually employed for the expression of the polypeptide or may include additionally one or more separate targeting sequences and may optionally encode a selectable marker. Promoters which can be used provided that such promoters are compatible with the host cell are e.g promoters obtained from the genomes of viruses such as polyoma virus, adenovirus (such as Adenovirus 2), papilloma virus (such as bovine papilloma virus), avian sarcoma virus, cytomegalovirus (such as murine or human cytomegalovirus immediate early promoter), a retrovirus, hepatitis-B virus, and Simian Virus 40 (such as SV 40 early and late promoters) or promoters obtained from heterologous mammalian promoters, such as the actin promoter or an immunoglobulin promoter or heat shock promoters.

Enhancers which can be used are e.g. enhancer sequences known from mammalian genes (globin, elastase, albumin, a-fetoprotein, and insulin) or enhancer from a eukaryotic cell virus, e.g. the SV40 enhancer, the cytomegalovirus early promoter enhancer, the polyoma, and adenovirus enhancers.

A wide variety of host/expression vector combinations may be employed in expressing the DNA sequences encoding the peptide(s) of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col El, pGEX, pCRI, pBR322, pmCherry, pET, pcDNA3, pMB9 and their derivatives, plasmids such as RP4; phage DNAs, e.g., the numerous derivatives of phage X, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Another concern of the present invention is to provide a eukaryotic or prokaryotic host cell containing the peptide according to the invention, the isolated and purified nucleic acid sequence of the invention and/or the expression vector described herein.

Transformation or transfection of appropriate eukaryotic or prokaryotic host cells with an expression vector comprising a purified and isolated DNA sequence according to the invention is accomplished by well-known methods that typically depend on the type of vector used. With regard to these methods, see for example, Maniatis et al. 1982, Molecular Cloning, A laboratory Manual, Cold Spring Harbor Laboratory and commercially available methods. The term "cell transfected" or "cell transformed" or "transfected/transformed cell" means the cell into which the extracellular DNA has been introduced and thus harbors the extracellular DNA. The DNA might be introduced into the cell so that the nucleic acid is replicable either as a chromosomal integrant or as an extra chromosomal element.

One or more of the polypeptides disclosed herein can be formulated for use as or in pharmaceutical compositions. Preferably, in addition to at least one peptide as described herein, the pharmaceutical compositions may contain one or more pharmaceutically acceptable carriers, diluents and adjuvants.

In some instances, pharmaceuticals can further include one or more additional therapeutic agents in amounts effective for achieving a modulation of disease or disease symptoms.

Pharmaceutically acceptable excipients, or vehicles, or carriers, diluents and adjuvants which facilitate processing of the active compounds into preparation which can be used pharmaceutically are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN®, PLURONICS® or polyethylene glycol (PEG).

The form of administration of the pharmaceutical composition may be systemic or topical. For example, administration of such a composition may be various parenteral routes such as subcutaneous, intravenous, intradermal, intramuscular, intraperitoneal, intranasal, transdermal, buccal routes or via an implanted device, and may also be delivered by peristaltic means.

The pharmaceutical composition comprising a peptide, as described herein, as an active agent may also be incorporated or impregnated into a bio-absorbable matrix, with the matrix being administered in the form of a suspension of matrix, a gel or a solid support. In addition the matrix may be comprised of a biopolymer.

Sustained-release preparations may be prepared. Suitable examples of sustained-release preparations include semi permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and [gamma] ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The pharmaceutical composition of the invention can also be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

Alternatively or in addition, the pharmaceutical composition of the invention can be administered by nasal aerosol or inhalation. Such composition is prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The formulations to be used for in vivo administration must be sterile. This is readily accomplished for example by filtration through sterile filtration membranes.

Preferably, the pharmaceutical composition of the invention is for use in the treatment and/or prevention of RSV infection.

In some instances, the present disclosure also provides pharmaceutically acceptable salts of the polypeptide of this invention. These include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate, trifluoromethylsulfonate, and undecanoate. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization.

The disclosure also includes methods of treating and/or preventing an RSV infection. The methods comprising administering an effective amount of i) at least one polypeptide of the invention, or ii) a pharmaceutically acceptable salt of a polypeptide of the invention or iii) a pharmaceutical composition of the invention, to a subject in need thereof.

The term "treat" or "treating," as used herein, refers to partially or completely alleviating, inhibiting, improving, and/or relieving the disease or condition from which the subject is suffering. In some instances, treatment can result in the continued absence of detectable RSV infection in a subject, or a reduction in the level of RSV infection in a subject. In general, methods include selecting a subject (in need thereof) and administering to the subject an effective amount of one or more of the peptides herein, e.g., in or as a pharmaceutical composition, and optionally repeating administration as required for the prophylaxis or treatment of RSV infection.

Selecting a subject can include selecting a subject at risk for RSV infection and/or exposed to RSV infection and/or those infected with RSV. The terms "subject" and "subject in need thereof," as used herein, refer to any animal. In certain embodiments, the subject is a mammal. In certain embodiments, the term "subject", as used herein, refers to a human (e.g., a man, a woman, or a child). Subjects at risk, or in need thereof, for RSV infection include those that may come into contact with RSV and/or have contacted a subject with RSV. Contact with RSV can occur, for example, during an RSV outbreak (e.g., in a finite geographical location), in a healthcare facility (e.g., a community clinic, a vaccination center, a doctors' office), in an outpatient facility, in a hospital (e.g., in an inpatient facility, in an intensive care unit), in an assisted living facility. Subjects can also include those scheduled to attend a healthcare facility or geographical area where infection by RSV may occur. Subjects can be referred by a medical practitioner or can be self-referred. In some instances, a level of RSV can be detected in a subject. Such levels of RSV can be used during treatment to detect a change in the level of RSV.

The term "administer," "administering," or "administration," as used herein, refers to implanting, absorbing, ingesting, injecting, or inhaling the inventive polypeptide or compound. In some instances, one or more of the peptides disclosed herein can be administered to a subject topically (e.g., nasally) and/or orally. For example, the methods herein include administration of an effective amount of compound or compound composition to achieve the desired or stated effect. Typically, the pharmaceutical compositions, the polypeptides as well or the pharmaceutical acceptable salt of the polypeptides, of this invention will be administered from about 1 to about 6 times per day or alternatively, as a continuous infusion. Such administration can be used as a chronic or acute therapy. In some embodiments, an effective dose of one or more of the peptides herein can include, but is not limited to, for example, about, 0.00001, 0.0001, 0.001, 0.01, 0.1, 1 or 10-10000; 0.00001, 0.0001, 0.001, 0.01, 0.1, 1 or 10-5000; 0.00001, 0.0001, 0.001, 0.01, 0.1, 1 or 10-2500; 0.00001, 0.0001, 0.001, 0.01, 0.1, 1 or 10-1000; 0.00001, 0.0001, 0.001, 0.01, 0.1, 1 or 10-900; 0.00001, 0.0001, 0.001, 0.01, 0.1, 1 or 10-800; 0.00001, 0.0001, 0.001, 0.01, 0.1, 1 or 10-700; 0.00001, 0.0001, 0.001, 0.01, 0.1, 1 or 10-600; 0.00001, 0.0001, 0.001, 0.01, 0.1, 1 or 10-500; 0.00001, 0.0001, 0.001, 0.01, 0.1, 1 or 10-400; 0.00001, 0.0001, 0.001, 0.01, 0.1, 1 or 10-300; 0.00001, 0.0001, 0.001, 0.01, 0.1, 1 or 10-200; 0.00001, 0.0001, 0.001, 0.01, 0.1, 1 or 10-100; 0.00001, 0.0001, 0.001, 0.01, 0.1, 1 or 10-90; 0.00001, 0.0001, 0.001, 0.01, 0.1, 1 or 10-80; 0.00001, 0.0001, 0.001, 0.01, 0.1, 1 or 10-70; 0.00001, 0.0001, 0.001, 0.01, 0.1, 1 or 10-60; 0.00001, 0.0001, 0.001, 0.01, 0.1, 1 or 10-50; 0.00001, 0.0001, 0.001, 0.01, 0.1, 1 or 10-40; 0.00001, 0.0001, 0.001, 0.01, 0.1, 1 or 10-30; 0.00001, 0.0001, 0.001, 0.01, 0.1, 1 or 10-20; 0.00001, 0.0001, 0.001, 0.01, 0.1, 1 or 10-30; 0.00001, 0.0001, 0.001, 0.01, 0.1, 1-15, 0.00001, 0.0001, 0.001, 0.01, 0.1, 1 or 10-30; 0.00001, 0.0001, 0.001, 0.01, 0.1, 1-10, 0.00001, 0.0001, 0.001, 0.01, 0.1, 1 or 10-30; or 0.00001, 0.0001, 0.001, 0.01, 0.1, 1-5 mg/kg/day.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Following administration, the subject can be evaluated to detect, assess, or determine the level of RSV infection in the subject. In some instances, treatment can continue until a change (e.g., reduction) in the level of RSV infection in the subject is detected.

Upon improvement of a patient's condition (e.g., a change or a decrease in the level of RSV infection in the subject), a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

The term "pharmaceutically effective amount" as used herein means that amount of a peptide as described above or a pharmaceutical composition or medicament comprising the peptide which is effective for producing some desired therapeutic effect in at least a sub-population of cells in the patient at a reasonable benefit/risk ratio applicable to any medical treatment.

The present invention also contemplates a method of inhibiting the RSV replication by disrupting, impairing and/or displacing the $N^0$-P interaction, the method comprising contacting i) at least one polypeptide of any one of claims 1 to 15, or ii) a pharmaceutically acceptable salt of a polypeptide of any one of claims 1 to 15, or iii) a pharmaceutical composition of any one of claims 1 to 2 with a cell.

Also provided is the use of a polypeptide of the invention in the manufacture of a medicament for treating and/or preventing an RSV infection.

The present invention also provides a polypeptide of the invention for use in the treatment and/or prevention of an RSV infection.

The invention further comprises a kit for the prophylaxis and/or treatment of RSV infection in a subject, said kit comprising at least one peptide of the invention, conjugated or not to an agent which increases the accumulation of said peptide in said cell, optionally with reagents and/or instructions for use.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

The foregoing description will be more fully understood with reference to the following Examples. Such examples, are, however, exemplary of methods of practicing the present invention and are not intended to limit the scope of the invention.

EXAMPLES

EX 1: Material and Methods

Materials.

Fmoc-amino acids and coupling reagents were purchased from Aapptec, Novabiochem and Bachem. The non-natural olefinic containing amino-acids were purchased at Okeanos Tech. Co., LTD. Solvents were purchased from Acros, Biosolve and Sigma-Aldrich.

Peptide Synthesis.

Peptides were synthesized by solid phase peptide chemistry on a Rink Amide AM resin LL (100-200 mesh, Novabiochem) at a 50 μmol scale. Each coupling was performed for 1 h at room temperature, using 200 μmol of Fmoc amino acid pre-activated with 190 μmol of HCTU and 400 μmol of diisopropyldiethylamine (DIEA) in N-Methyl-2-pyrrolidone (NMP). For the coupling following the non-natural olefinic amino acids, HCTU was replaced by 195 μmol of HATU, and the coupling was performed for two hours at room temperature. Following final Fmoc deprotection and N-terminal acetylation, the metathesis was performed under constant nitrogen degassing, in a 2 ml solution containing 10 mM 1$^{st}$ generation Grubbs' catalyst in dichloroethane (DCE). The metathesis was performed for 2 hours at room temperature. Peptides were deprotected and cleaved from the resin with a cleavage cocktail consisting of TFA:TIS:H$_2$O (95/2.5/2.5) for 2 hrs. For cysteine containing peptides, we used TFA:TIS:H$_2$O:EDT (94/2.5/2.5/1) instead. Crude peptides were analyzed by UPLC/MS (Waters Acquity Ultra Performance LC/Micromass Quattro micro API) on a ACQUITY UPLC BEH C18 column (1.7 μl, 1.0×50 mm), and purified by HPLC preparative (Waters 2777 sample manager, Waters 2545 binary gradient module, Waters 2487 Dual λ Absorbance Detector) using a Kinetex XB-C18 100A column (100×21.2 mm; diam. particle size, 5 μm). Samples were lyophilized and quantified with the Qubit® 2.0 Fluorometer (Life Technologies).

CD Spectroscopy.

CD experiments were performed on a Jasco-810 or on a Chirascan spectropolarimeter in a thermostated cell holder at 20° C. The samples were prepared in 10 mM phosphate buffer, pH 7.5, at a peptide concentration of 25 μM for HEVS 73-79 or 50 pM for the other peptides. The far-UV spectra were recorded at 25° C. by step scan from 190 nm to 250 nm with a scan rate of 100 nm per min using a bandwidth of 1 nm and an integration time of 1 s. Each spectrum was the average of 5 scans. The spectra were substracted from buffer baseline and smoothed using the FFT filter (Jasco Software, Tokyo, Japan). The data were converted to per residue molar ellipticity units [Θ] (deg.cm$^2$.dmol$^{-1}$.residue$^{-1}$). The percentage of helicity was calculated as follows:

$$\% \text{ Helicity} = \frac{100 * CD_{222}}{C * N * \left\{-40000 * \left[1 - \left(\frac{2.5}{N}\right)\right]\right\}}$$

whereby CD$_{222}$=molar ellipticity [e] at 222 nm in [mdeg], N=number of amino acids in the peptide and C=peptide molar concentration [mol/1].

Cloning and Site Directed Mutagenesis.

The pGEX-P[1-40] plasmid was obtained by introducing a stop codon in the sequence of pGEX-P encoding for the full length P by site-directed mutagenesis, using the Quickchange site-directed mutagenesis kit (Stratagene). The Ala mutants were then introduced in pGEX-P[1-40] by site-directed mutagenesis. The plasmid pET-N$_{K170AR185A}$ was used to produce the monomeric N protein (termed N$^{mono}$) with a C-terminal poly-His tag. Plasmids for eukaryotic expression of the HRSV proteins N, P, M2-1, and L designated pN, pP, pM2-1 and pL, have been described previously (Fix et al., 2011; Tran et al., 2009). The pM/Luc subgenomic replicon which encodes the firefly luciferase (Luc) gene under the control of the M/SH gene start sequence was derived from the pM/SH subgenomic replicon (Hardy and Wertz, 1998) and has been described previously (Tran et al., 2009). Point mutations were introduced in pP by site directed mutagenesis as described above. The plasmid pP[1-29] was obtained by substituting the codon encoding for the residue 30 of P by a stop codon, by site-directed mutagenesis. The plasmid pmCherry-P[1-29] was obtained by cloning previously PCR amplified mCherry gene into BamHI restriction sites in frame with the P sequence in the plasmid pP, and stop codons were inserted in the sequence of P. Sequence analysis was carried out to check the integrity of all the constructions.

Expression and Co-Purification of Recombinant Proteins.

E coli BL21 bacteria (DE3) (Novagen, Madison, Wis.) co-transformed with pGEX-P[1-40] and pET-N$_{K170AR185A}$ plasmids were grown at 37° C. for 8 hours in 100 ml of Luria Bertani (LB) medium containing 100 μg/ml ampicillin and 50 μg/ml kanamycin. The same volume of LB was then added and protein expression was induced by adding 80 μg/ml isopropyl-β-D-thio-galactoside (IPTG) to the medium. The bacteria were incubated for 15 hours at 28° C. and then harvested by centrifugation. For GST-fusion protein purification, bacterial pellets were re-suspended in lysis buffer (50 mM Tris-HCl pH 7.8, 60 mM NaCl, 1 mM EDTA, 2 mM DTT, 0.2% Triton X-100, 1 mg/ml lysozyme) supplemented with complete protease inhibitor cocktail (Roche, Mannheim, Germany) and incubated for 1 hour on ice, sonicated, and centrifuged at 4° C. for 30 min at 10,000 g. Glutathione-Sepharose 4B beads (GE Healthcare, Uppsala, Sweden) were added to clarified supernatants and incubated at 4° C. for 15 hours. Beads were then washed two times in lysis buffer and three times in PBS 1x, then stored at 4° C. in an equal volume of PBS. Samples were boiled in Laemmli buffer and analyzed by SDS-PAGE and Coomassie blue staining.

Surface Plasmon Resonance (SPR) Assays.

Real-time SPR assays were carried out using a Proteon XPR36 (BioRad) instrument equilibrated at 25° C. in 20 mM TrisHCl pH 8.5, 150 mM NaCl, 5% glycerol, 0.01% Tween20. A goat anti-GST antibody (Biacore GST Capture Kit) was covalently coupled to a GLC sensorchip, using the Amine Coupling Kit (GE Healthcare), reaching an immobilization density of around 4500 resonance units (RU; 1 RU≈1 pg·mm-2). The antibody-functionalized surface was used to capture tightly GST-fused P[1-40] mutants (or GST as a control) to a density of 100-160 RU, or GST (800 RU) as a control. $N^{mono}$ (19 µM, 6.33 µM, 2.1 µM, 703 nM, and 234 nM) was then injected in duplicate over the GST-P[1-40] (wild type or mutants) and GST surfaces for one minute at a flow rate of 50 µl·min-1. The surfaces were then regenerated by washing with a 10 mM glycine-HCl (pH 1.5) for 2 minutes and 0.05% SDS for 1 minute. The real-time interaction profiles were double referenced using the Proteon manager software (BioRad), that is both the signals from the reference surface (with GST captured on the anti-GST antibody) and from buffer blank experiments were subtracted. The SPR steady-state responses were plotted against the $N^{mono}$ concentration and fitted using the Proteon Manager 3.1 software (BioRad).

$N^0$-P Fluorescence Polarization Assay.

10 µl of recombinant $N^{mono}$ (1 µM) was incubated with 10 µL of fluorescently labeled FAM-P(1-40) (10 nM) and 10 µl of the stapled peptide at the desired concentration in 384-well plates. The binding mixture was incubated for 20 min at room temperature and transferred onto a SpectraMax Paradigm reader for lecture of fluorescence polarization. The curves were analyzed using the Igor software, and the Ki values were calculated using the Hill equation.

Cell Culture and Transfections.

HEp-2 (ATCC number CCL-23) and BHK-21 (clone BSRT7/5) cells were maintained in Eagle's miminum essential medium (EMEM) and Dulbecco's modified Eagle's medium (DMEM), respectively, supplemented with 10% FCS, 2 mM L-glutamine, and penicillin-streptomycin solution. The cells were grown in an incubator at 37° C. in 5% $CO_2$. Cytotoxicity assays were done with the CellTiter-Glo Luminescent cell viability assay (Promega). Cells were transfected using Lipofectamine 2000 (Invitrogen, Cergy-Pontoise, France) as described by the manufacturer.

Minigenome Replication Assay.

BSRT-7 cells at 90% confluence in twenty-four-well dishes were transfected with Lipofectamine 2000 (Invitrogen) with a plasmid mixture containing 0.5 µg of pM/Luc, 0.5 µg of pN, 0.25 µg of pP, 0.25 µg of pL, and 0.125 µg of pM2-1 (Tran et al., 2009), as well as 0.125 µg of pRSV-β-Gal (Promega) to normalize transfection efficiencies. Transfections were done in duplicate, and each independent transfection was performed three times. Cells were harvested 24 h post-transfection, then lyzed in luciferase lysis buffer (30 mM Tris pH 7.9, 10 mM $MgCl_2$, 1 mM DTT, 1% Triton X-100, and 15% glycerol). Luciferase activities were determined for each cell lysate with an Anthos Lucy 3 luminometer (Bio Advance, Bussy Saint Martin, France) and normalized based on β-galactosidase (β-Gal) expression. For the experiments including the overexpression of peptides derived from the N-terminal domain of P, up to 0.25 µg of plasmids pP[1-29] or pmCherry-P[1-29], was co-transfected with the plasmids required to produce the replicating minigenome.

rHRSV-mCherry Inhibition Assay.

HEp-2 cells were seeded at $5 \times 10^4$ cells per well in 96 well plates the day before and infected for 2 hours with 500 PFU of RSV-mCherry. The medium was then changed against MEM without phenol red medium containing dilutions of peptides. Each point of peptide dilution was made in duplicate. Plates were incubated 48 h at 37° C. and mCherry fluorescence measurement was performed using a spectrofluorometer (Tecan infinite M200PRO) with excitation and emission wavelengths of 580 and 620 nm, respectively (expressed in relative fluorescence units RFU). Non-infected HEp-2 cells were used as standards for fluorescence background levels.

In Vivo Mice Luciferase Assay.

Female BALB/c mice were purchased from the Centre d'ElevageR. Janvier (Le Genest Saint-Isle, France) and were used around 8 weeks of age. Mice strains were bred in a pathogen-free animal facility. Mice were fed normal mouse chow and water ad libitum and were raised and housed under standard conditions with air filtration. For infection experiments, mice were housed in cages inside stainless steel isolation cabinets that were ventilated under negative pressure with high-efficiency particulate air-filtered air. Mice were anesthetized by a mixture of ketamine and xylazine (1 and 0.2 mg per mouse, respectively) and infected IN with 50 µl of PBS containing $6 \times 10^4$ PFU of rHRSV-Luc. Body temperature and body weight were monitored at days 3-10. For in vivo imaging, mice were anesthetized. Alternatively, mice were killed at different time points, and lungs were then collected. For each time point, experiments were done in quadruplicate. For antiviral drug administration to animals, HEVS 124 was dissolved in sterile PBS pH 7.4 at 0.6 mg/ml. All animals were treated with 50 µl of dissolved HEVS 124 delivered by intranasal inhalation. Oral treatments were administered 1 h prior to RSV inoculation and then once on day 2 and on day 4. This experiment was repeated once.

EX 2: Results

Identification of P Mutants Impairing the Activity of the Polymerase.

We have shown that the first 30 N-terminal residues of P are sufficient to interact with the monomeric N (Galloux et al, J. Virol, 2015). We performed the Ala-scanning mutagenesis of residues Glu2 to F28 of P by site directed mutagenesis of the plasmid encoding P to investigate if the P mutants can impair the activity of the replication complex. The effect of each mutant was assessed in an HRSV minigenome replication assay (Tran et al., 2009). Briefly, the bicistronic subgenomic replicon pM/Luc was cotransfected with plasmids encoding N, P, L and M2-1, in cells expressing T7 RNA polymerase. In this system the production of the luciferase protein is dependent and thus proportional to the replication and transcription processes. As shown on FIG. 1A, the 11 mutants E2A, F4A, E7A F8A, G10A, F20A, L21A, E22A, I24A, K25A and G26A displayed a reduction of luciferase activity of about 50% relative to wild type P protein. The E2A, F4A, F8A, G10A and F20A mutations had the strongest effect, with a reduction of nearly 80% of the polymerase activity. As assessed by Western blot, all the P mutants of the critical domain (Glu2-F28) were expressed in similar amounts in eukaryotic cells compared to wild type P protein (data not shown).

Identification of Key Residues in P (1-40) Required for Binding to the Monomeric N Protein.

Figure 1B:
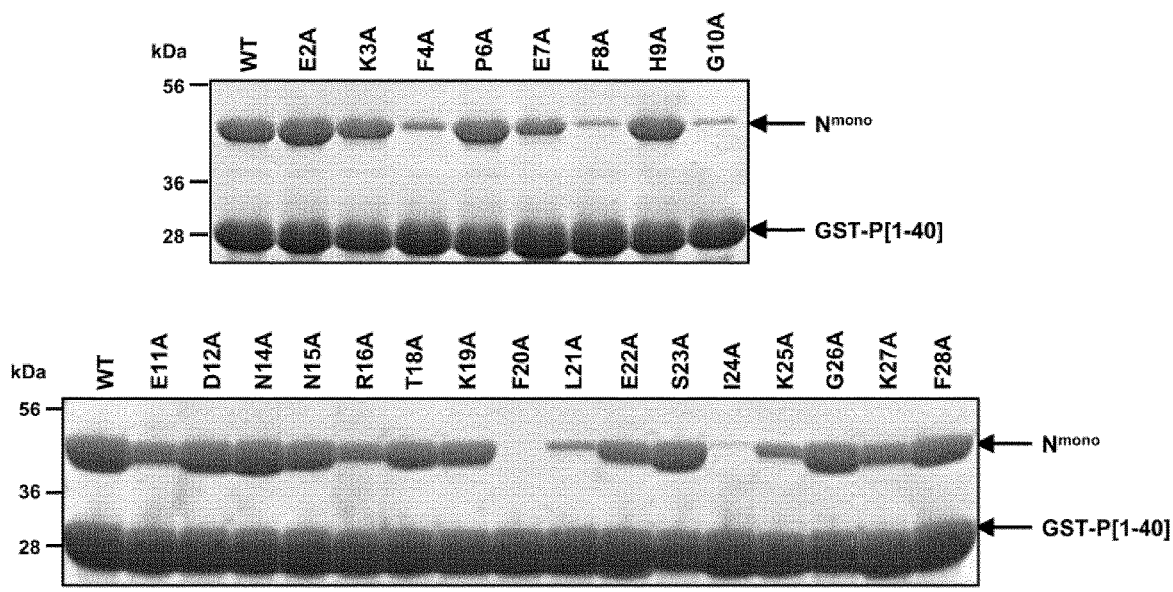

To confirm that the defect of RNA synthesis observed for some P mutants was due to the disruption of the P-N$^0$ interaction, the N$_{K170AR185A}$-His protein)(N$^{mono}$) was co-expressed with the GST-P[1-40] mutant proteins in $E.$ $coli$, and the resulting P-N complexes were purified by affinity chromatography using the GST tag. Purified complexes were analyzed by SDS-PAGE. As shown in FIG. 1B, mutations F4A, F8A, G10A, F20A, L21A and I24A totally or nearly abrogated the interaction of GST-P[1-40] with N$^{mono}$. The substitutions E7A and K25A attenuated partially the interaction compared to the wild type P[1-40]. The other mutations, and more specifically E2A, E22A, and G26A which were shown to induce a decrease of polymerase activity, did not significantly modify the interaction between P[1-40] and N$^{mono}$. In order to confirm these results and to quantify the impact of P mutations E2A-G10A and F20A-G26A on the interaction with N$^{mono}$, we then characterized the specific interaction between GST-P[1-40] (wild type or mutants) and N$^{mono}$ by surface plasmon resonance (SPR). GST-P[1-40] proteins were captured on an anti-GST antibody surface and serial dilutions of N$^{mono}$ were injected. We first characterized the specific interaction between wild type GST-P[1-40] and N$^{mono}$. The interaction was transient, with a very fast dissociation rate and a Kd of 4-5 µM (FIG. 2). Similar affinities were obtained for mutants K3A, P6A, H9A and S23A. Mutations F8A and F20A had the strongest effect on the interaction with N$^{mono}$, with calculated K$_D$ of 41 µM and >100 µM, respectively. The affinity for N$^{mono}$ was also affected by mutations of residues F4, E7, L21, and I24 (10 µM<K$_D$<20 µM), and to a lesser extent by mutations of residues G10, E22 and K25 (5 µM<K$_D$<10 µM). Finally, the affinity of GST-P[1-40] for N$^{mono}$ was increased nearly two-fold by mutations E2A and G26A, with K$_D$s of 1.9 µM and 2.6 µM, respectively.

Altogether, these results reveal that Phe4, Glu7, Phe8, Gly10, Phe20, Leu21, Ile24 and Lys25 are residues that are directly involved in the interaction with the soluble monomeric RNA-free N protein.

Overexpression of N-Terminal Peptides of P Inhibits Viral Replication.

Figure 3:
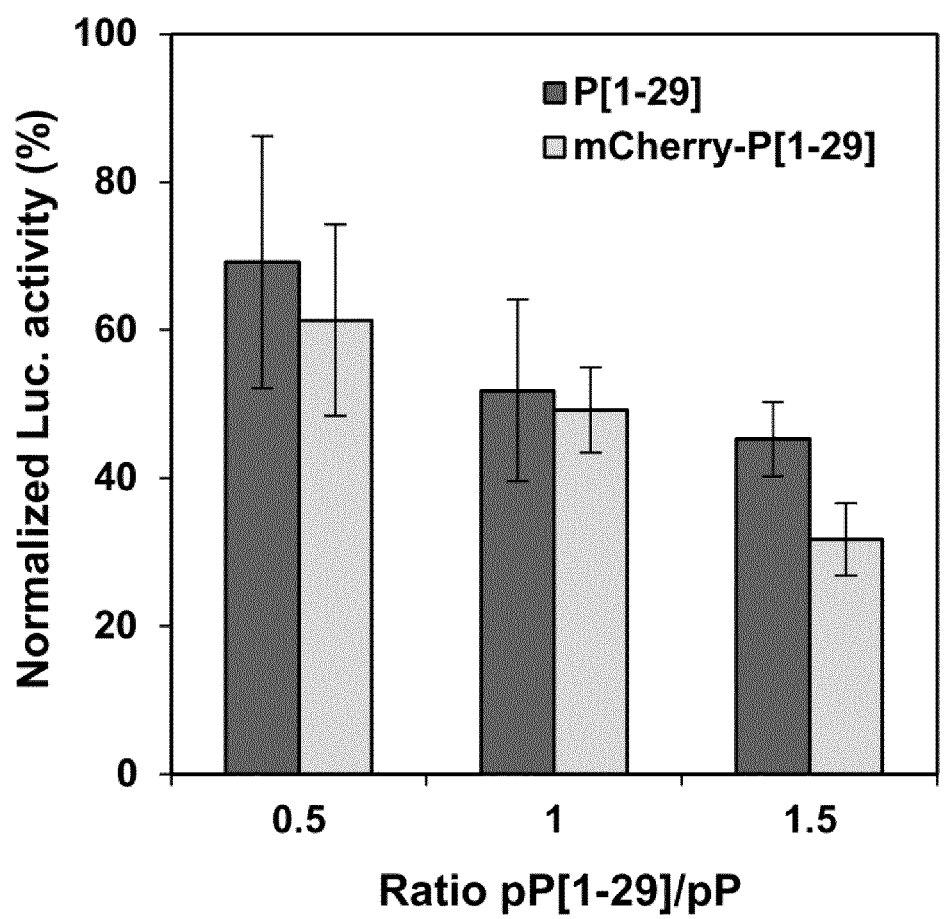
FIG. 3: Inhibition of RSV replication by P[1-29]. BSRT7/5 cells were transfected with pP, pN, pM2-1, pL plasmids and pM/Luc, together with pCMV-βGal for transfection standardization, and various ratios of pP[1-29]/pP or pmCherry-P[1-29]/pP. Viral RNA synthesis was quantified by measuring the Luc activity after cell lysis 24 h after transfection. Each Luc activity value was normalized based on β-galactosidase expression, and is the average of three independent experiments performed in duplicate. Error bars represent standard deviations calculated based on three independent experiments made in duplicate.

To evaluate if a short peptide corresponding to the N-terminal domain of P can interfere with RSV replication, a plasmid encoding P[1-29] was co-transfected in BSRT7/5 cells in the context of the minireplicon. The polymerase activity assayed by measuring Luc activity was reduced in a dose dependent manner by P[1-29] expressing plasmid (FIG. 3). Similar results were obtained when using a plasmid encoding mCherry-P[1-29], which presented the advantage to validate the expression of P[1-29] by immunofluorescence. The production of Luc in this system depends on the encapsidation by N$^0$ of both the neo-synthesized negative sense minigenome which is required for replication, and of the positive sense minigenome that is required for its transcription by the LIP complex. It is thus expected that overexpression of the short peptide P[1-29] is sufficient to inhibit both the replication and the transcription of the RSV genome by RdRp in mammalian cells.

Stapled Peptide Walk of the RSV P N-Terminal Domain.

Figure 4A:
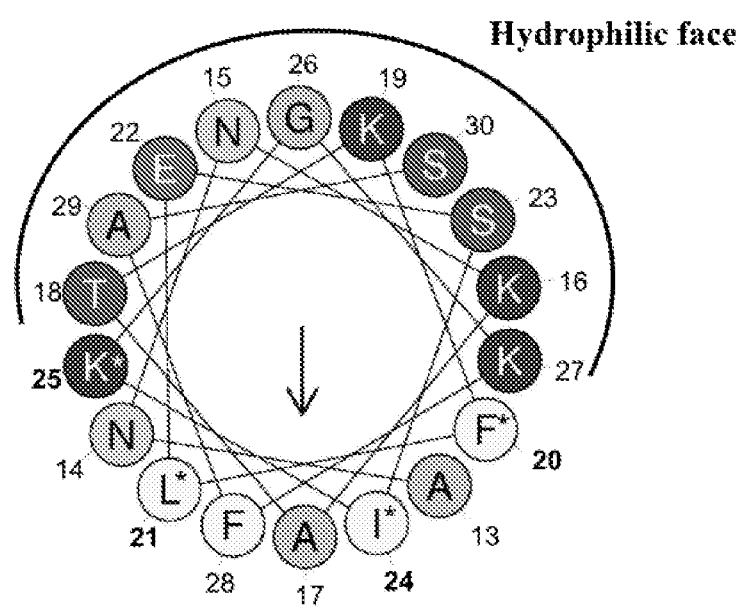
FIGS. 4A-4B: α-helical wheel representations of: A. P(13-30), the peptide region reported to have intrinsic α-helical properties (Lassoued et al., 2013). Stapling was performed on the hydrophilic side of this representation. The asterisks denote the residues that were identified to be critical in the alanine scanning mutagenesis experiments. B. Putative α-helical P(2-19) based on the x-ray structure of the Nipah virus $N^0$-P complex (Yabukarski F. et al., Structure of Nipah virus unassembled nucleoprotein in complex with its viral chaperone, 2014, 21(9):754-9). The hydrophilic side is designed on the basis of the alanine scanning mutagenesis results (key residues denoted by asterisks), and is used to incorporate non-natural amino acids for stapling.
Figure 4B:
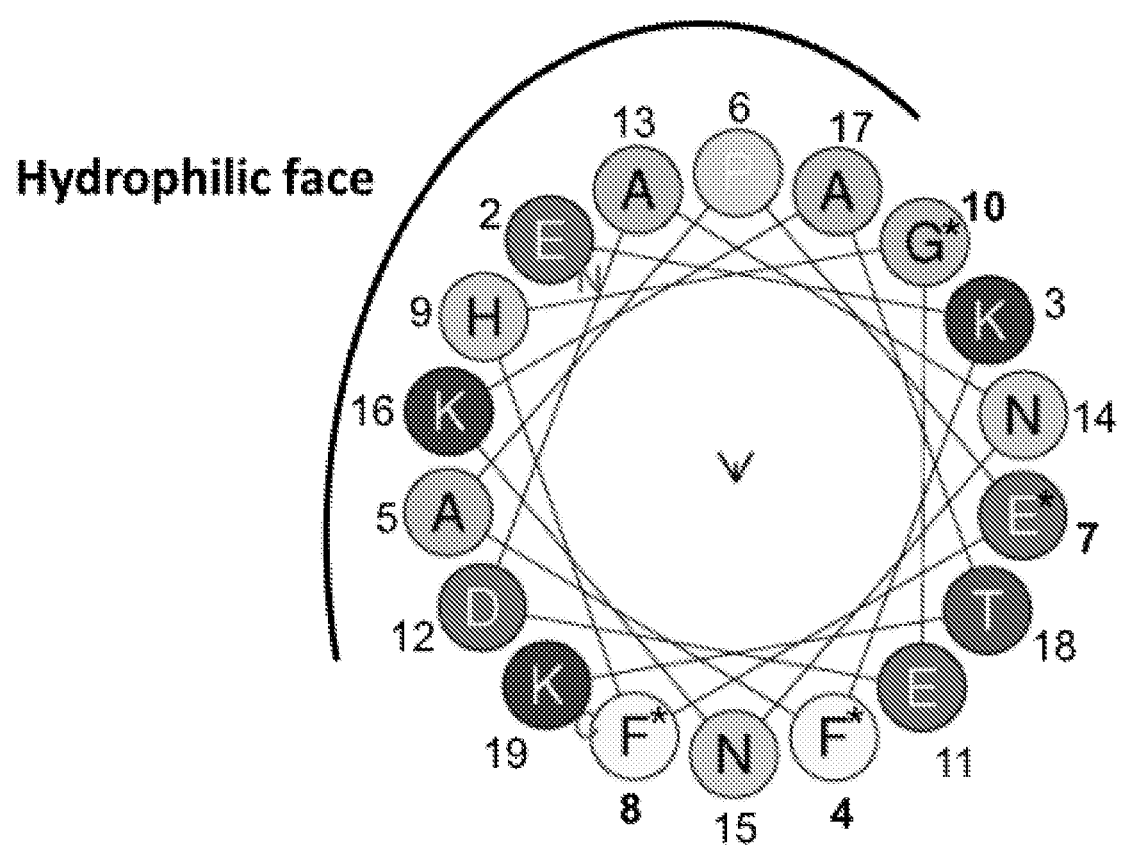

Based on our results and on the prediction that the P(13-30) fragment folds into an α-helix upon binding to its target (Lassoued et al., 2013), we decided to design peptides to interfere with the N$^0$-P interaction. However, the use of this synthetic peptide as dominant negative inhibitor is unlikely to work, because of the length of this peptide, which is too short (20 residues) to allow folding and binding to the target. A well-known strategy to bypass this issue consists in stabilizing the α-helical nature of the peptide in the unbound state by chemical cross-linking of amino-acid side chains that are not interacting with the target, thereby decreasing the entropic cost for binding to the target (Sia et al., 2002). Recently, the stapled peptides chemistry technology has emerged as a promising tool to solve this issue. Non-natural olefinic amino acids are inserted into the peptides at positions that do not interfere with target binding, and the olefinic side chains are cross-linked by ruthenium catalyzed metathesis (Kim et al., 2011; Verdine and Hilinski, 2012). Additionally, the stapled peptide chemistry can increase dramatically the potency, proteolytic stability and cell permeability of the peptide inhibitor (Bird et al., 2010). Based on the α-helical wheel representation of P (13-30), we identified Asn15, Lys16, Thr18, Lys19, Glu22, Ser23, Gly26, Lys27, Ala29 and Ser30 at suitable positions for inserting non-natural amino-acids (FIG. 4A). The length of the peptide was extended to Glu11 to add a negative charge on the N-terminus of the peptide with the aim to stabilize the macrodipole of the helix, and to obtain an overall peptide charge of zero for enhanced cell-permeability (FIG. 6A) (Kim et al., 2011).

Biochemical Characterization of Stabilized α-Helices of P(11-30).

Figure 7A:
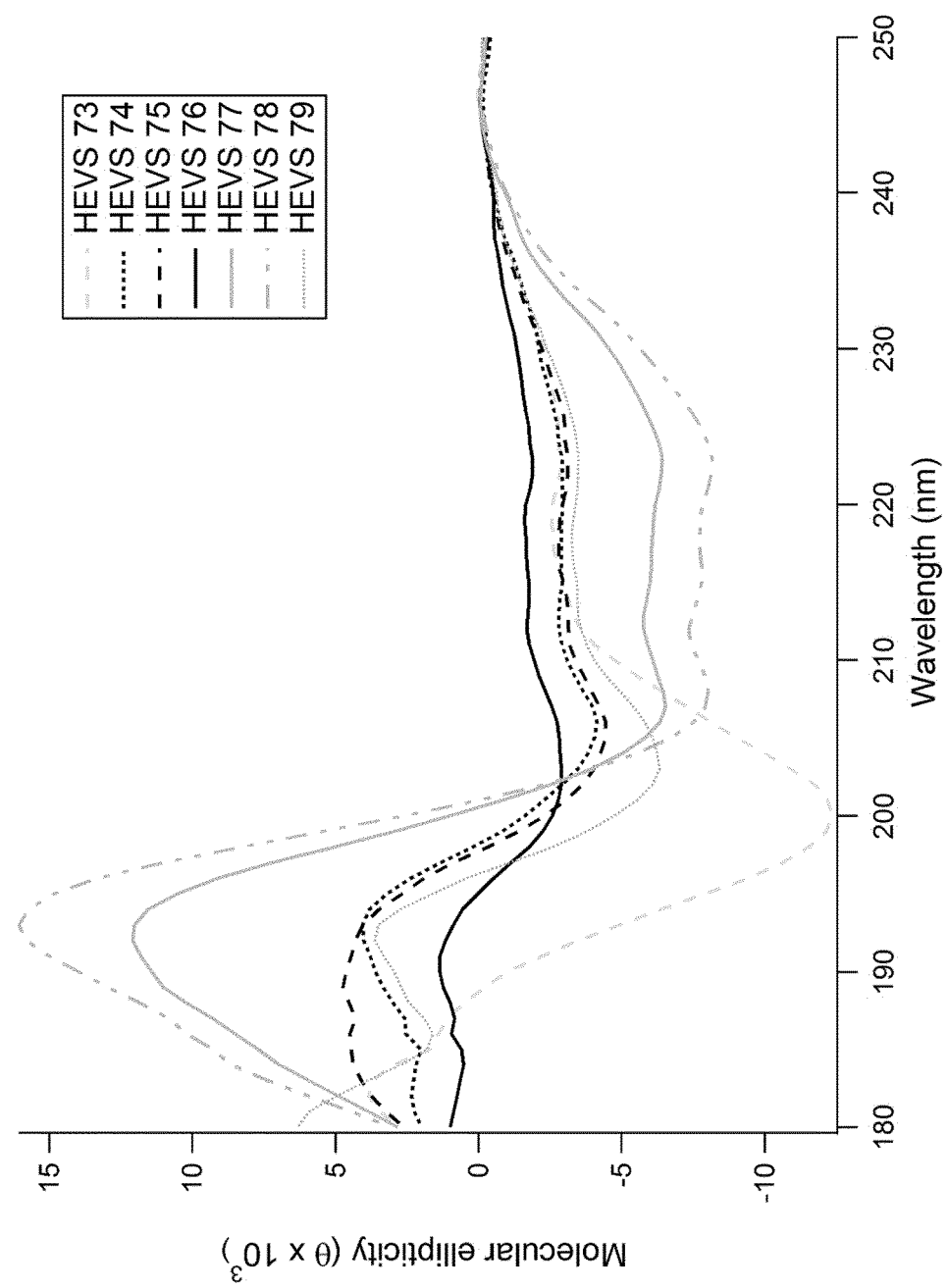
FIGS. 7A-7C: Far-UV CD spectra of stapled peptides in 10 mM phosphate buffer, pH 7.5. A. HEVS 73-79; B. HEVS 108-114; C. HEVS 115-129.
Figure 7B:
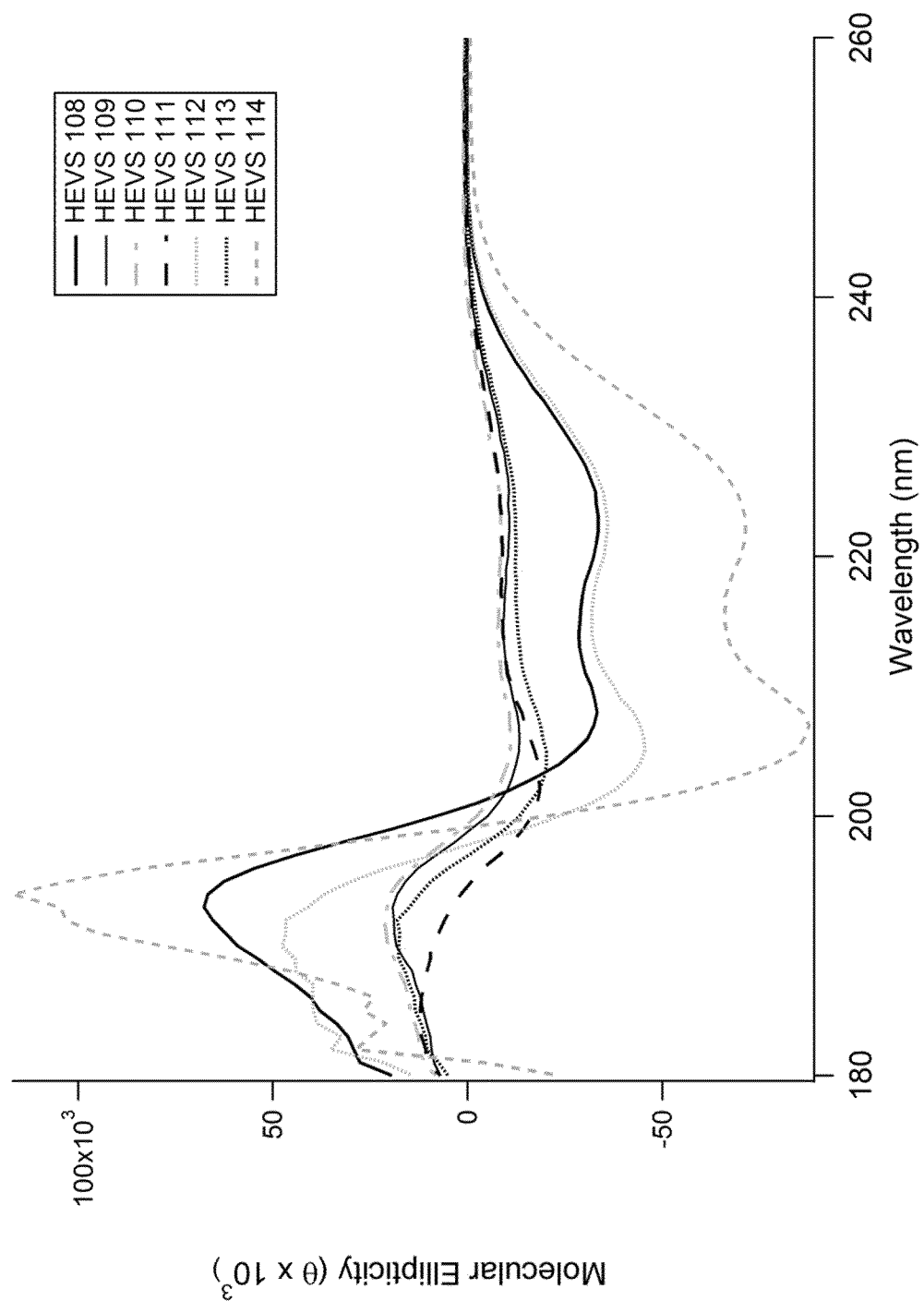
Figure 7C:
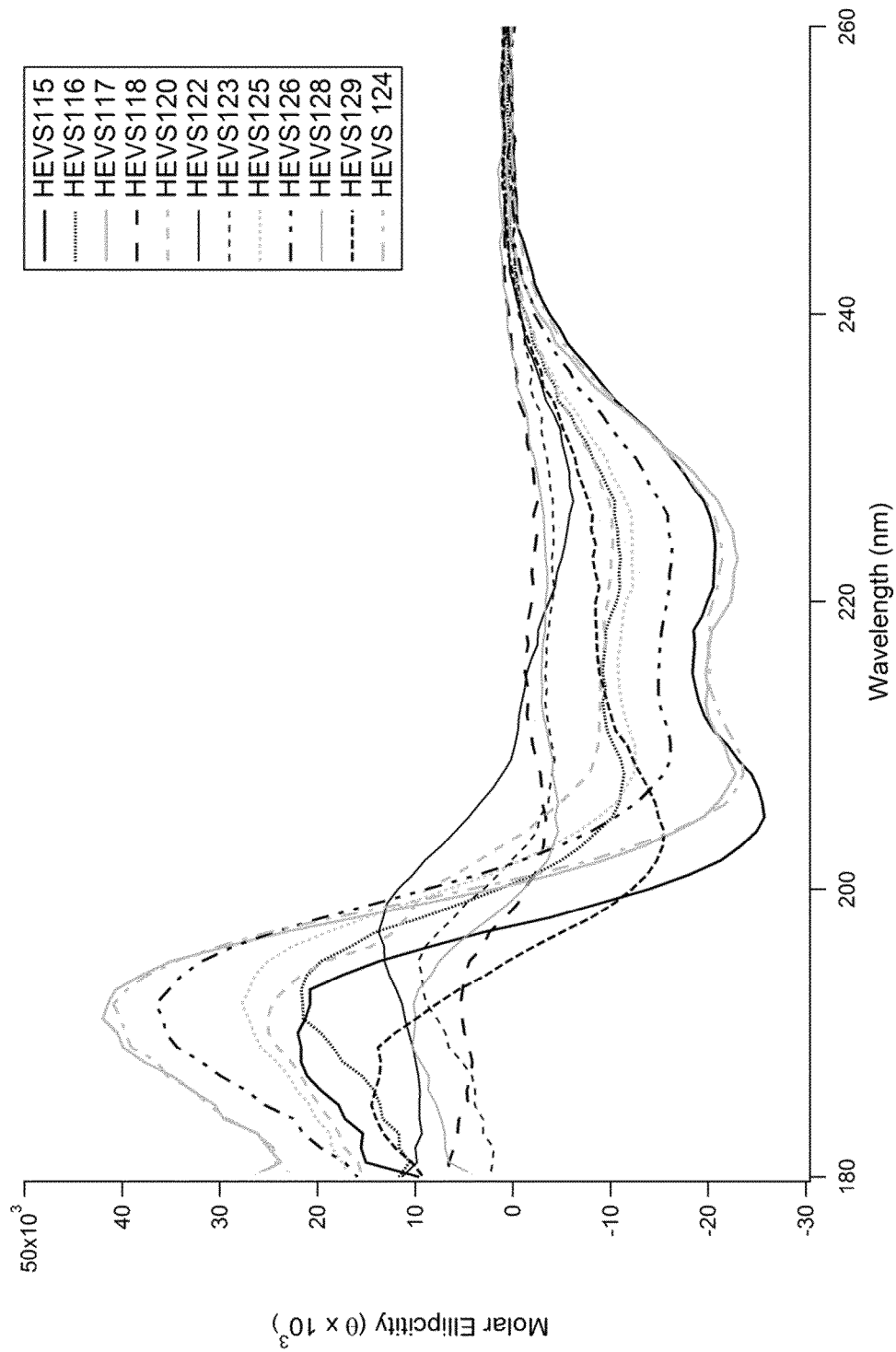
Figure 8A:
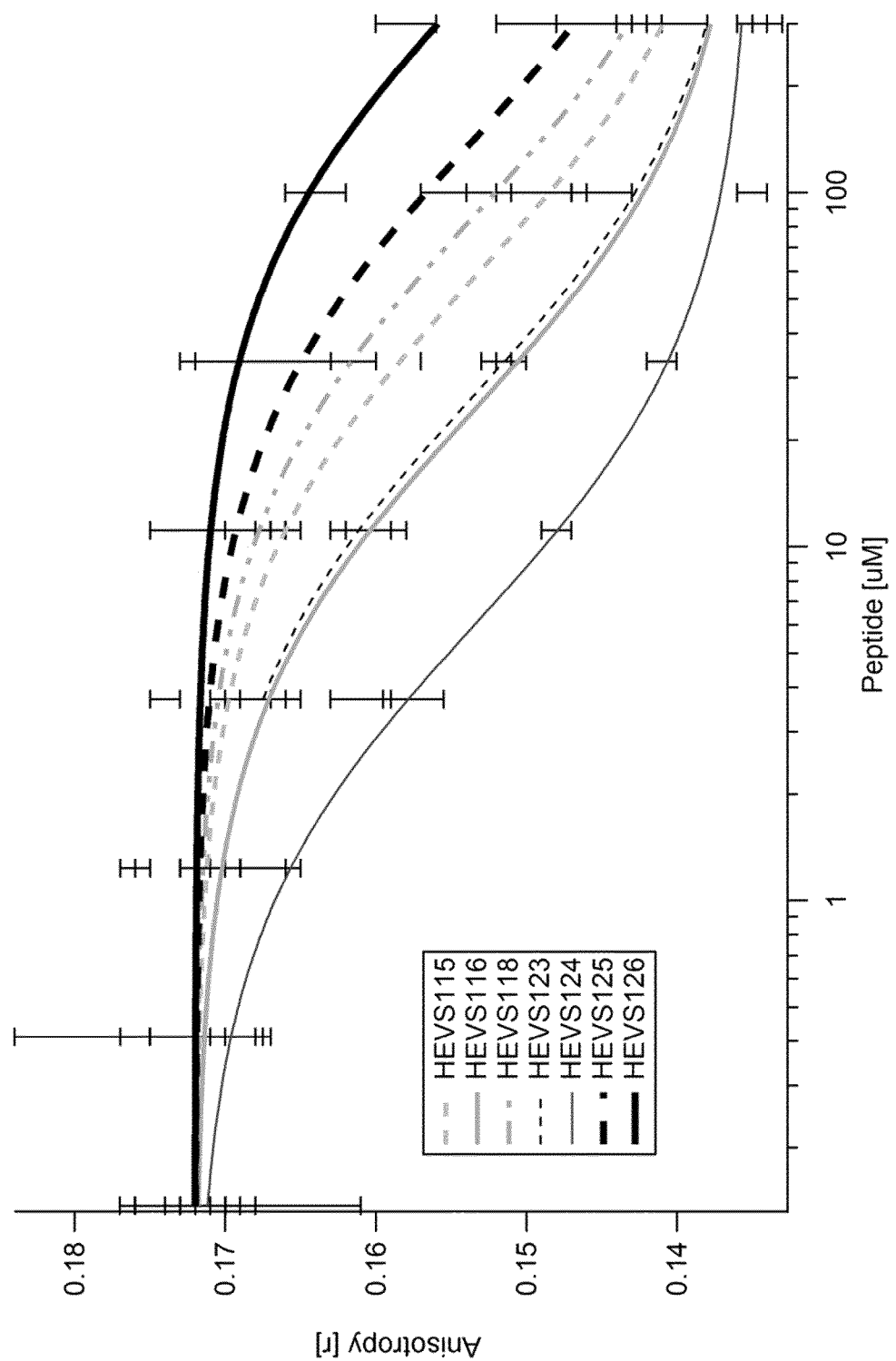
FIGS. 8A-8B: Inhibitory activity of stapled peptides in the $N^0$-P biochemical fluorescence polarization competition assay. A. HEVS 115-126; B. HEVS 108-114.
Figure 8B:
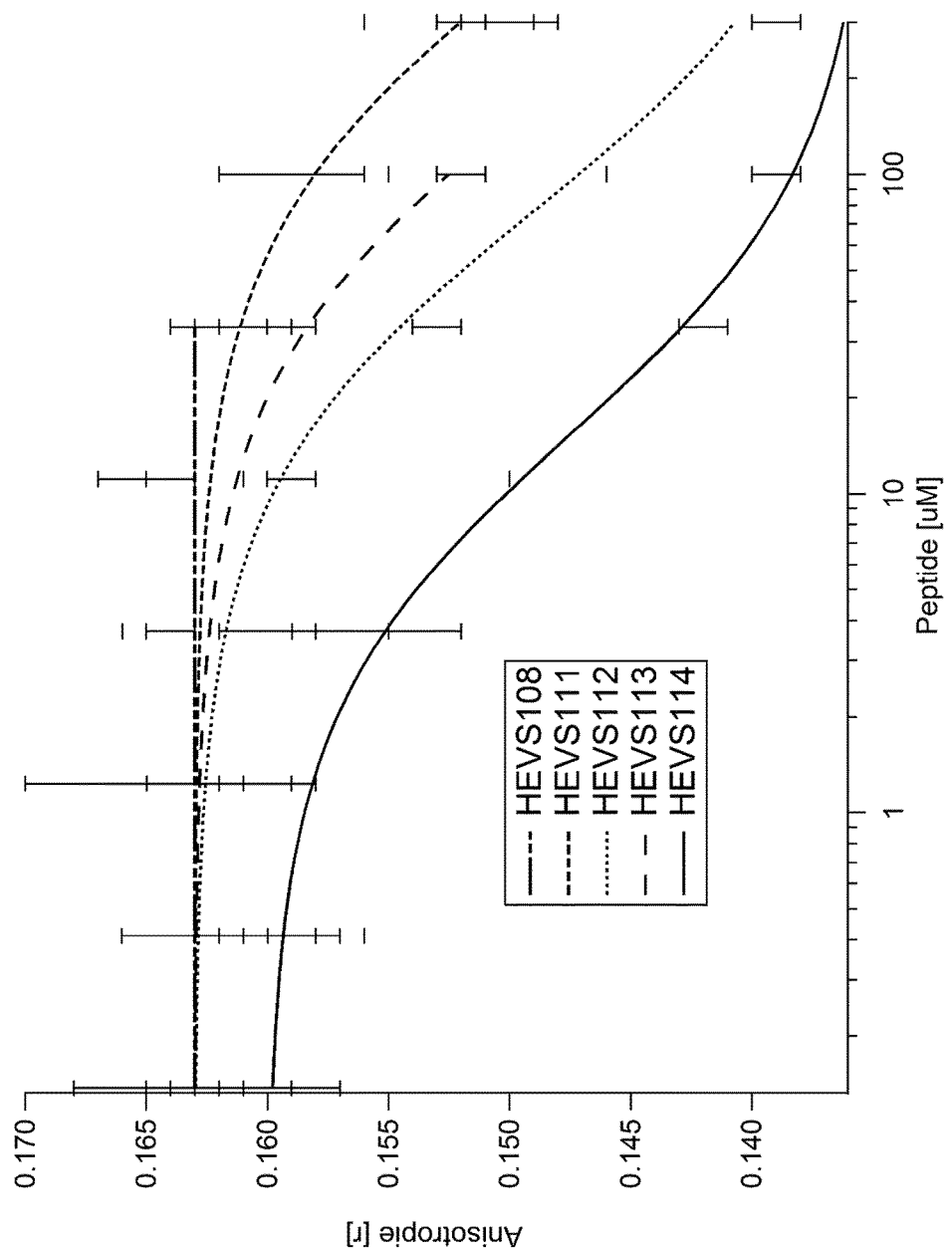
Figure 9A:
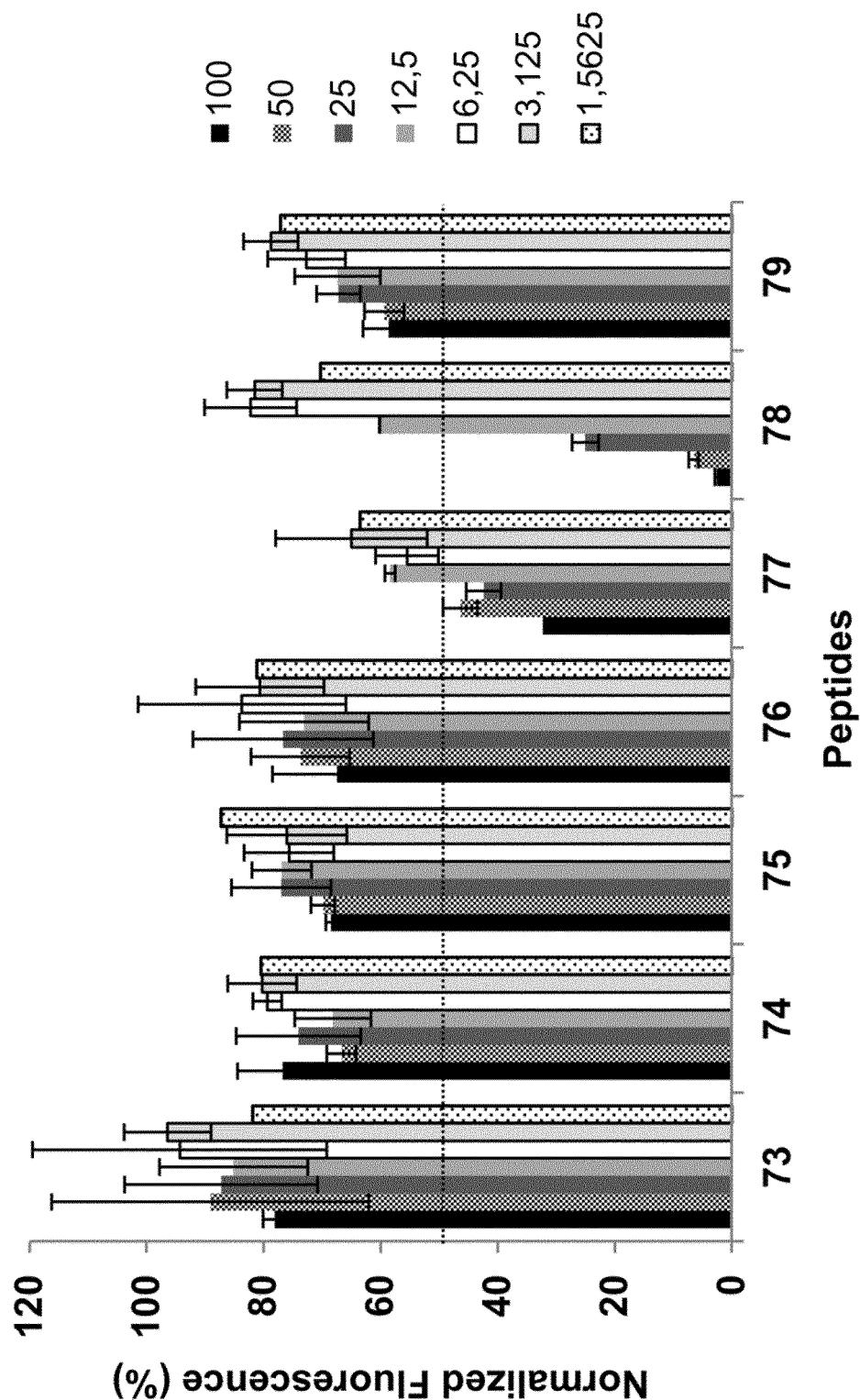
FIGS. 9A-9C: Inhibitory activity of stapled peptides in the rHRSV-mCherry replication assay. HEp-2 cells were seeded in 96 well plates and infected with 500 PFU of rHRSV-Cherry virus. Following viral infection, cells were incubated in the presence of serial dilutions of stapled peptides. The red fluorescence was read at 48 h post infection by automatic counting. A. HEVS 73-79; B. HEVS 108-114; C. HEVS 115-129.
Figure 9B:
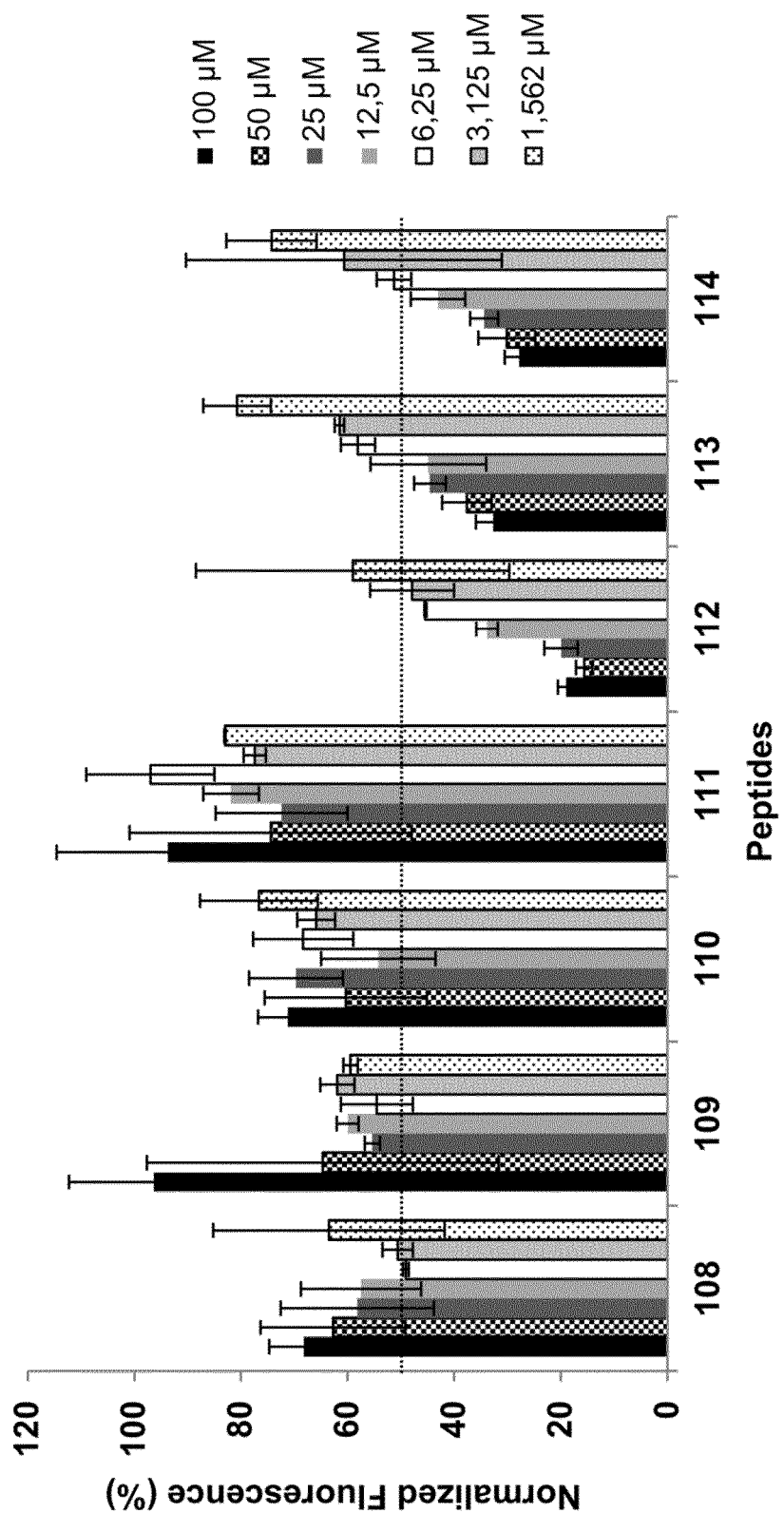
Figure 9C:
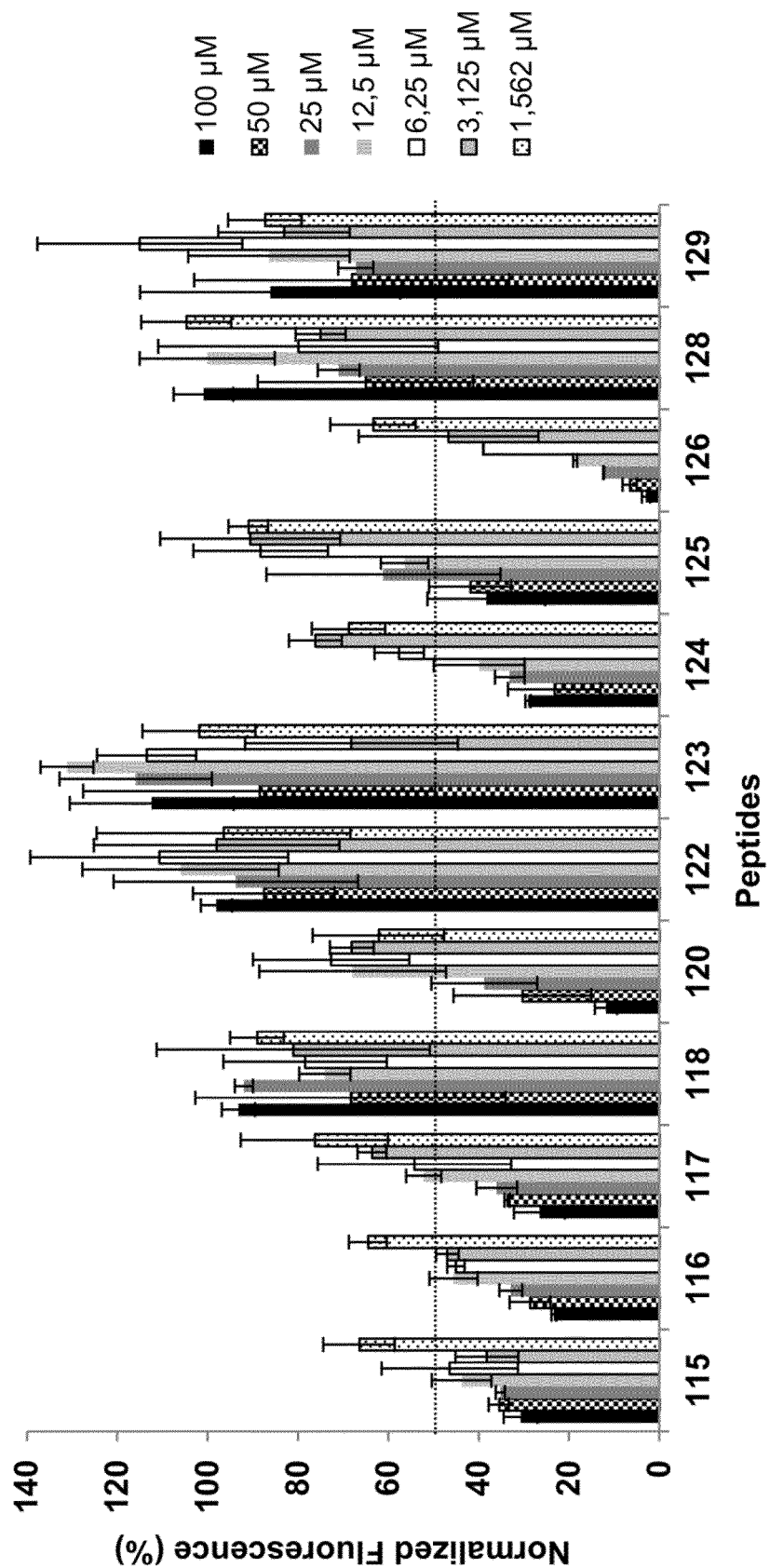

Far UV circular dichroism (CD) spectropolarimetry was used to investigate the effect of the stapling on the α-helical content of the peptides. The native HEVS 73 appeared to be largely unfolded with a characteristic minimum at 200 nm (FIG. 7A). As expected, stapling conferred a significant enhancement of α-helical content to all peptides as observed by the displacement of the random coil minimum toward 208 nm and the appearance of a second minimum at 222 nm. The extent of α-helical increase varied significantly among the peptides and ranged from 17% to 47% (FIG. 7A).

Stabilized α-Helices of P(11-30) Inhibit the Activity of the RSV Polymerase.

Next the potential activity of stapled peptides was tested on infected cells. Hep2 cells were infected with a RSV-mCherry virus engineered by reverse genetics (Rameix-Welti et al, Nat Comm., 2014), and increasing concentrations of stapled peptides were added post-infection to study their effect on viral replication. We found that HEVS 77 and HEVS 78 were able to inhibit viral replication ($EC_{50}$=60 μM and 15 μM respectively). However, the inhibitory activity of HEVS 78 was largely mediated due to cell cytotoxicity ($CC_{50}$ of approximately 40 μM). Unexpectedly, HEVS 79, which was shown to presents a lower α-helical content, also appear to have an antiviral activity ($EC_{50}$ around 80 μM). These data suggest that, from our panel of 6 stapled peptides that were synthesized, HEVS 77 and HEVS 79 are capable to inhibit viral replication in cells.

Based on these results, we combined the staples of HEVS 77, HEVS 78 and HEVS 79 into double and stitched stapled peptides (FIG. 6B) and extended the best candidate HEVS 77 up to Glu 7 into the singly HEVS 124, and the doubly HEVS 125 and 126 stapled peptides (FIG. 6C). Additionally, we screened the remaining P(11-30) single stapled peptide combinations that had not yet been investigated (FIG. 6A).

Consistent with the result of the first series of peptides described above, circular dichroism showed that stapling resulted in a significant increase of their α-helical content (FIG. 7B, C). In certain instances, the extent of the α-helical increase could be increased up to 96%. In the viral replication assay, HEVS 124 and HEVS 126 were found to be the most potent compounds with $EC_{50}$ values of 11 μM and 3.5 μM, respectively (FIG. 9 C). However, HEVS 126 was cytotoxic at a concentration of 100 μM. In parallel, to assess the propensity of the stapled peptides to impair the $N^0$-P interaction, we tested these peptides in a biochemical fluorescence polarization assay, which measures the binding affinity of the stapled peptides to recombinant $N^{mono}$ in comparison of native fluorescently labeled P(1-40). As it can be seen in FIGS. 8A-C, HEVS 124 displayed the best affinity toward $N^0$ (Ki=6 μM), while HEVS 126 bound very poorly to the target.

Figure 10A:
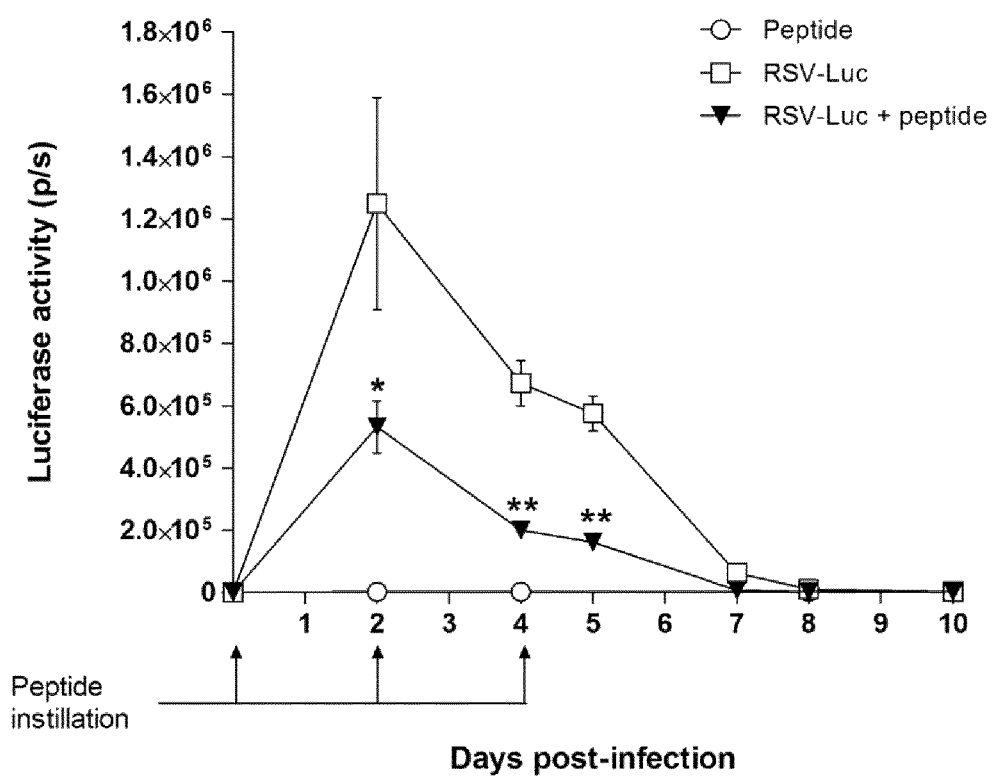

Based on these results, in vivo proof of concept was performed by intranasal administration of HEVS 124 at 0.6 mg/ml, to BALB/c mice inoculated with a Luc-encoding RSV that enables direct visualization of the virus replication in living mice. The virus was inoculated with or without HEVS 124 (50 μL in PBS), and the peptide administration was repeated at days 2 and 4. This experiment demonstrated a significant reduction of luciferase activity in treated mice (FIG. 10A). No sign of toxicity such as body temperature shift, weight loss or morbidity was observed (FIGS. 10B-C).

REFERENCES

Bird, G. H., N. Madani, A. F. Perry, A. M. Princiotto, J. G. Supko, X. He, E. Gavathiotis J. G. Sodroski, and L. D. Walensky, 2010, Hydrocarbon double-stapling remedies the proteolytic instability of a lengthy peptide therapeutic: Proc Natl Acad Sci USA, v. 107, p. 14093-8.

Blackwell, H. E., J. D. Sadowsky, R. J. Howard, J. N. Sampson, J. A. Chao, W. E. Steinmetz, D. J. O'Leary, and R. H. Grubbs, 2001, Ring-closing metathesis of olefinic peptides: design, synthesis, and structural characterization of macrocyclic helical peptides: J Org Chem, v. 66, p. 5291-302.

Castagné, N., A. Barbier, J. Bernard, H. Rezaei, J. C. Huet, C. Henry, B. Da Costa, and J. F. Eléouët, 2004, Biochemical characterization of the respiratory syncytial virus P-P and P-N protein complexes and localization of the P protein oligomerization domain: J Gen Virol, v. 85, p. 1643-53.

Castel, G., M. Chtéoui, G. Caignard, C. Préhaud, S. Méhouas, E. Réal, C. Jallet, Y. Jacob, R. W. Ruigrok, and N. Tordo, 2009, Peptides that mimic the amino-terminal end of the rabies virus phosphoprotein have antiviral activity: J Virol, v. 83, p. 10808-20.

Collins, P. L., and J. A. Melero, 2011, Progress in understanding and controlling respiratory syncytial virus: still crazy after all these years: Virus Res, v. 162, p. 80-99.

Fix, J., M. Galloux, M. L. Blondot, and J. F. Eléouët, 2011, The insertion of fluorescent proteins in a variable region of respiratory syncytial virus L polymerase results in fluorescent and functional enzymes but with reduced activities: Open Virol J, v. 5, p. 103-8.

Futaki S. et al, "Arginine-rich peptides. An abundant source of membrane-permeable peptides having potential as carriers for intracellular protein delivery" J. Biol. Chem., 276, 5836, 2001.

Galloux, M., B. Tarus, I. Blazevic, J. Fix, S. Duquerroy, and J. F. Eléouët, 2012, Characterization of a viral phosphoprotein binding site on the surface of the respiratory syncytial nucleoprotein: J Virol, v. 86, p. 8375-87.

Hardy, R. W., and G. W. Wertz, 1998, The product of the respiratory syncytial virus M2 gene ORF1 enhances readthrough of intergenic junctions during viral transcription: J Virol, v. 72, p. 520-6.

Ioannides C. G. et al, "Inhibition of IL-2 receptor induction and IL-2 production in the human leukemic cell line Jurkat by a novel peptide inhibitor of protein kinase C" Cell Immunol., 131, 242, 1990.

Kawamoto, S. A., A. Coleska, X. Ran, H. Yi, C. Y. Yang, and S. Wang, 2012, Design of triazole-stapled BCL9 α-helical peptides to target the β-catenin/B-cell CLL/lymphoma 9 (BCL9) protein-protein interaction: J Med Chem, v. 55, p. 1137-46.

Kim, Y. W., T. N. Grossmann, and G. L. Verdine, 2011, Synthesis of all-hydrocarbon stapled α-helical peptides by ring-closing olefin metathesis: Nat Protoc, v. 6, p. 761-71.

Kole H. K. et al., "A peptide-based protein-tyrosine phosphatase inhibitor specifically enhances insulin receptor function in intact cells" J. Biol. Chem. 271, 14302, 1996.

Lassoued, S., M. Galloux, J. Fix, C. Van Heinjenoort, F. Bontems, J.-F. Eléouët, and C. Sizun, 2013, NMR reveals alpha-helical propensity in RSV P protein outside the oligomerization domain, XV International Conference on Negative Strand Viruses, Granada, Spain.

Maniatis et al. 1982, Molecular Cloning, A laboratory Manual, Cold Spring Harbor Laboratory Mason, S. W., E. Aberg, C. Lawetz, R. DeLong, P. Whitehead, and M. Liuzzi, 2003, Interaction between human respiratory syncytial virus (RSV) M2-1 and P proteins is required for reconstitution of M2-1-dependent RSV minigenome activity: J Virol, v. 77, p. 10670-6.

Qian Z. M. et al., "Targeted drug delivery via the transferrin receptor-mediated endocytosis pathway" Pharmacological Reviews, 54, 561, 2002

Rameix-Welti M A, Le Goffic R, Hervé P L, Sourimant J, Rémot A, Riffault S, Yu Q, Galloux M, Gault E, Eléouët J F. Visualizing the replication of respiratory syncytial virus in cells and in living mice. Nat Commun. 2014 Oct. 3; 5:5104. doi: 10.1038/ncomms6104.

Schafmeister, C. E., J. Po, and G. L. Verdine, 2000, An All-Hydrocarbon Cross-Linking System for Enhancing the Helicity and Metabolic Stability of Peptides: Journal of American Chemical Society, v. 122, p. 5891-5892.

Sela M, Zisman E. Different roles of D-amino acids in immune phenomena FASEB J. 1997 May; 11(6):449-56. Review. Sia, S. K., P. A. Carr, A. G. Cochran, V. N. Malashkevich, and P. S. Kim, 2002, Short c constrained peptides that inhibit HIV-1 entry: Proc Natl Acad Sci USA, v. 99, p. 14664-9.

Stewart, M. L., E. Fire, A. E. Keating, and L. D. Walensky, 2010, The MCL-1 BH3 helix is an exclusive MCL-1 inhibitor and apoptosis sensitizer: Nat Chem Biol, v. 6, p. 595-601.

Thompson, W. W., D. K. Shay, E. Weintraub, L. Brammer, N. Cox, L. J. Anderson, and K. Fukuda, 2003, Mortality associated with influenza and respiratory syncytial virus in the United States: JAMA, v. 289, p. 179-86.

Walensky, L. D., A. L. Kung, I. Escher, T. J. Malia, S. Barbuto, R. D. Wright, G. Wagner, G. L. Verdine, and S. J. Korsmeyer, 2004, Activation of apoptosis in vivo by a hydrocarbon-stapled BH3 helix: Science, v. 305, p. 1466-70.

Wunderlich, K., M. Juozapaitis, C. Ranadheera, U. Kessler, A. Martin, J. Eisel, U. Beutling, R. Frank, and M.

Schwemmle, 2011, Identification of high-affinity PB1-derived peptides with enhanced affinity to the PA protein of influenza A virus polymerase: Antimicrob Agents Chemother, v. 55, p. 696-702.

Yabukarski F, et al., Structure of Nipah virus unassembled nucleoprotein in complex with its viral chaperone. Nat Struct Mol Biol. 2014 September; 21(9):754-9. doi: 10.1038/nsmb.2868. Epub 2014 Aug. 10.

The invention claimed is:

1. A polypeptide that interacts or interferes with the binding of the RSV nucleoprotein N with the RSV phosphoprotein P by disrupting, impairing and/or displacing the $N^0$-P interaction, wherein said polypeptide is internally cross-linked and is selected from:

an amino acid sequence: $A_{11} A_{12} A_{13} A_{14} A_{15} A_{16} A_{17} A_{18} A_{19} A_{20} A_{21} A_{22} A_{23} A_{24} A_{25} A_{26} A_{27} A_{28} A_{29} A_{30}$ (SEQ ID NO: 2); or an amino acid sequence: $A_7 A_8 A_9 A_{10} A_{11} A_{12} A_{13} A_{14} A_{15} A_{16} A_{17} A_{18} A_{19} A_{20} A_{21} A_{22} A_{23} A_{24} A_{25} A_{26} A_{27} A_{28} A_{29} A_{30}$ (SEQ ID NO: 3);

or a fragment thereof, wherein the fragment contains at least 15 contiguous amino acids of SEQ ID NO: 3;
or a pharmaceutically acceptable salt thereof;
and wherein said polypeptide includes at least two modified amino acids that together form an internal cross-link wherein said internally cross-linked amino acids are located at positions selected from A15, A16, A18, A19, A22, A23, A26, A27, A29, and A30 and are separated by 2 (i, i+3), 3 (i, i+4) or 6 (i, i+7) amino acids, and wherein those modified amino acids are selected from R,S-bis-pentenyl-glycine, S-pentenyl-alanine, R-pentenyl-alanine, S-octenyl-alanine and R-octenyl-alanine and wherein:

$A_7$ is Glu, or any other polar negatively charged amino acid,
$A_8$ is Phe or Trp, or any other large aromatic amino acid,
$A_9$ is His,
$A_{10}$ is Gly or Ala,
$A_{11}$ is Glu or Asn,
$A_{12}$ is Asp or Gln,
$A_{13}$ is Ala, Gly, Val, Leu, Ile, Phe, Met or Trp,
$A_{14}$ is Asn or Gln,
$A_{15}$ is Asn or Gln,
$A_{16}$ is Lys or Arg,
$A_{17}$ is Ala, Gly, Val, Leu, Ile, Phe, Met or Trp or any other nonpolar amino acid,
$A_{18}$ is Thr, Val, Ile or Leu,
$A_{19}$ is Lys or Arg,
$A_{20}$ is Phe or Trp, or any other large aromatic amino acid,
$A_{21}$ is Leu, Gly, Val, Ile, Phe, Met or Trp or any other nonpolar amino acid, $A_{22}$ is Glu or Asp,
$A_{23}$ is Ser, Ala, Thr or Gly,
$A_{24}$ is Ile, Gly, Val, Leu, Phe, Met or Trp or any other nonpolar amino acid,
$A_{25}$ is Lys or Arg,
$A_{26}$ is Gly, Ala, Val, Leu or Ile,
$A_{27}$ is Lys or Arg,
$A_{28}$ is Phe, Tyr or Trp, or any other nonpolar amino acid,
$A_{29}$ is Ala, Gly, Val, Leu, Ile, Phe, Met or Trp,
$A_{30}$ is Ser.

2. The polypeptide of claim 1, wherein said polypeptide comprises at least two modified amino acids at positions A16 and A23.

3. The polypeptide of claim 1, wherein the internally cross-linked polypeptide consists of a biologically active sequence selected from the group consisting of SEQ ID No: 8 (HEVS 77), SEQ ID No: 15 (HEVS 112), SEQ ID No: 16 (HEVS 113), SEQ ID No: 17 (HEVS 114), SEQ ID No: 18 (HEVS 115), SEQ ID No: 19 (HEVS 116), SEQ ID No: 20 (HEVS 117), SEQ ID No: 22 (HEVS 120), SEQ ID No: 23 (HEVS 121), SEQ ID No: 26 (HEVS 124), SEQ ID No: 27 (HEVS 125), and SEQ ID No: 28 (HEVS 126).

4. The polypeptide of claim 1 conjugated to an agent that increases the accumulation of said polypeptide in a cell.

5. The polypeptide of claim 4, wherein the agent that increases the accumulation of said polypeptide in a cell is a cell membrane permeable carrier.

6. The polypeptide of claim 4, wherein the cell membrane permeable carrier is a cell membrane peptide carrier.

7. The polypeptide of claim 5, wherein the cell membrane peptide carrier is a positively charged amino acid peptide.

8. The polypeptide of claim 6, wherein the positively charged amino acid peptide is selected from the group comprising the HIV-TAT 48-57 peptide [GRKKRRQRRR], the FHV-coat 35-49 peptide [RRRRNRTRRNRRRVR], the HTLV-II Rex 4-16 peptide [TRRQRTRRARRNR], the NYAD-1 peptide [ITFXDLLXYYGP, X=(S)-alpha-(2'-pentenyl) alanine], the BMV gag 7-25 peptide [KMTRAQRRAAARRNRWTAR] and the R9 peptide [RRRRRRRRR].

9. The polypeptide of claim 1, said polypeptide comprising one or more amino acid in the L-form or in D-form, and/or in a retro-inverso isomer form.

10. The polypeptide of claim 1, wherein the N-terminal end of the amino acid sequence of said polypeptide is covalently linked to one or more chemical entities selected from the group comprising an acetyl, a fatty acid, a cholesterol, a poly-ethylene glycol (PEG), a XTEN sequence, a nuclear localization signal, nuclear export signal, an antibody, a polysaccharide and a targeting molecule.

11. The polypeptide of claim 1, said polypeptide comprising one or more non-conventional amino acids.

12. A pharmaceutically acceptable salt of a polypeptide of claim 1.

13. A pharmaceutical composition comprising at least one polypeptide of claim 1 and one or more pharmaceutically acceptable excipients, or vehicles, or carriers.

14. A method of treating and/or preventing a RSV infection comprising administering an effective amount of at least one polypeptide of claim 1, a pharmaceutically acceptable salt of said polypeptide or a pharmaceutical composition of said polypeptide.

15. An inhaler comprising an effective amount of at least one polypeptide of claim 1, a pharmaceutically acceptable salt of said polypeptide or a pharmaceutical composition of said polypeptide and a pharmaceutically acceptable propellant.

16. A method of inhibiting the RSV replication by disrupting, impairing and/or displacing the $N^0$-P interaction, the method comprising contacting at least one polypeptide of claim 1, a pharmaceutically acceptable salt of said polypeptide or a pharmaceutical composition of said polypeptide with a cell.

17. The polypeptide of claim 1, wherein the internally cross-linked polypeptide consists of a biologically active sequence selected from the group consisting of SEQ ID NO: 8 (HEVS 77), SEQ ID NO: 22 (HEVS 120), SEQ ID NO: 26 (HEVS 124), SEQ ID NO: 27 (HEVS 125), and SEQ ID NO: 28 (HEVS 126), fragments containing at least 15 contiguous amino acids, or conservative variants thereof, wherein said variants are at least 80% identical to the respective sequences.

* * * * *

UNITED STATES PATENT AND TRADEMARK OFFICE
CERTIFICATE OF CORRECTION

PATENT NO. : 10,774,114 B2  
APPLICATION NO. : 15/125309  
DATED : September 15, 2020  
INVENTOR(S) : Origène Nyanguile, Jean-François Eleouet and Marie Galloux Page 1 of 1

It is certified that error appears in the above-identified patent and that said Letters Patent is hereby corrected as shown below:

In the Specification

<u>Column 24,</u>
Line 29, "[e] at" should read --[Θ] at--.

<u>Column 27,</u>
Line 36, "523A." should read --S23A.--.
Line 64, "LIP complex." should read --L/P complex.--.

In the Claims

<u>Column 63,</u>
Line 3, Claim 1 "or Tip" should read --or Trp--.
Line 8, Claim 1 "or Tip" should read --or Trp--.
Line 9, Claim 1 "or Tip" should read --or Trp--.

Signed and Sealed this
Twentieth Day of July, 2021

Drew Hirshfeld
*Performing the Functions and Duties of the
Under Secretary of Commerce for Intellectual Property and
Director of the United States Patent and Trademark Office*

```
                        SEQUENCE LISTING

<160> NUMBER OF SEQ ID NOS: 36

<210> SEQ ID NO 1
<211> LENGTH: 40
<212> TYPE: PRT
<213> ORGANISM: Unknown
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Met
<220> FEATURE:
<221> NAME/KEY: MISC_FEATURE
<222> LOCATION: (2)..(2)
<223> OTHER INFORMATION: Glu, or any polar negatively charged amino
      acid, and their amides
<220> FEATURE:
<221> NAME/KEY: MISC_FEATURE
<222> LOCATION: (3)..(3)
<223> OTHER INFORMATION: Lys, or any polar positively charged amino acid
<220> FEATURE:
<221> NAME/KEY: MISC_FEATURE
<222> LOCATION: (4)..(4)
<223> OTHER INFORMATION: Phe, or any large aromatic amino acid
<220> FEATURE:
<221> NAME/KEY: MISC_FEATURE
<222> LOCATION: (5)..(5)
<223> OTHER INFORMATION: Ala, or any nonpolar amino acid
<220> FEATURE:
<221> NAME/KEY: MISC_FEATURE
<222> LOCATION: (6)..(6)
<223> OTHER INFORMATION: Pro, or any nonpolar amino acid
<220> FEATURE:
<221> NAME/KEY: MISC_FEATURE
<222> LOCATION: (7)..(7)
<223> OTHER INFORMATION: Glu, or any polar negatively charged amino
      acid, and their amides
<220> FEATURE:
<221> NAME/KEY: MISC_FEATURE
<222> LOCATION: (8)..(8)
<223> OTHER INFORMATION: Phe, or any large aromatic amino acid
<220> FEATURE:
<221> NAME/KEY: MISC_FEATURE
<222> LOCATION: (9)..(9)
<223> OTHER INFORMATION: His, or any polar positively charged amino acid
<220> FEATURE:
<221> NAME/KEY: MISC_FEATURE
<222> LOCATION: (10)..(10)
<223> OTHER INFORMATION: Gly, or any small aliphatic, nonpolar or
      slightly polar amino acid
<220> FEATURE:
<221> NAME/KEY: MISC_FEATURE
<222> LOCATION: (11)..(11)
<223> OTHER INFORMATION: Glu, or any polar negatively charged amino
      acid, and their amides
<220> FEATURE:
<221> NAME/KEY: MISC_FEATURE
<222> LOCATION: (12)..(12)
<223> OTHER INFORMATION: Asp, or any polar, negatively charged
      amino acid and their amides
<220> FEATURE:
<221> NAME/KEY: MISC_FEATURE
<222> LOCATION: (13)..(13)
<223> OTHER INFORMATION: Ala, or a conservative amino acid substitution
      Gly, Val, Leu, Ile or any nonpolar amino acid
<220> FEATURE:
<221> NAME/KEY: MISC_FEATURE
<222> LOCATION: (14)..(14)
<223> OTHER INFORMATION: Asn, or any polar, negatively charged
      amino acid and their amides
```

```
<220> FEATURE:
<221> NAME/KEY: MISC_FEATURE
<222> LOCATION: (15)..(15)
<223> OTHER INFORMATION: Asn, or any polar, negatively charged
      amino acid and their amides
<220> FEATURE:
<221> NAME/KEY: MISC_FEATURE
<222> LOCATION: (16)..(16)
<223> OTHER INFORMATION: Lys, or any polar positively charged amino acid
<220> FEATURE:
<221> NAME/KEY: MISC_FEATURE
<222> LOCATION: (17)..(17)
<223> OTHER INFORMATION: Ala, or a conservative amino acid substitution
      Gly, Val, Leu, Ile or any nonpolar amino acid
<220> FEATURE:
<221> NAME/KEY: MISC_FEATURE
<222> LOCATION: (18)..(18)
<223> OTHER INFORMATION: Thr, or any small aliphatic, nonpolar or
      slightly polar amino acid
<220> FEATURE:
<221> NAME/KEY: MISC_FEATURE
<222> LOCATION: (19)..(19)
<223> OTHER INFORMATION: Lys , or any polar positively charged amino
      acid
<220> FEATURE:
<221> NAME/KEY: MISC_FEATURE
<222> LOCATION: (20)..(20)
<223> OTHER INFORMATION: Phe, or any large aromatic amino acid
<220> FEATURE:
<221> NAME/KEY: MISC_FEATURE
<222> LOCATION: (21)..(21)
<223> OTHER INFORMATION: Leu, or a conservative amino acid substitution
      Gly, Val, Ile or any nonpolar amino acid
<220> FEATURE:
<221> NAME/KEY: MISC_FEATURE
<222> LOCATION: (22)..(22)
<223> OTHER INFORMATION: Glu, or any polar negatively charged amino
      acid, and their amides
<220> FEATURE:
<221> NAME/KEY: MISC_FEATURE
<222> LOCATION: (23)..(23)
<223> OTHER INFORMATION: Ser, or any small aliphatic, nonpolar or
      slightly polar amino acid
<220> FEATURE:
<221> NAME/KEY: MISC_FEATURE
<222> LOCATION: (24)..(24)
<223> OTHER INFORMATION: Ile, or a conservative amino acid substitution
      Gly, Arg, Val, Leu or any nonpolar amino acid
<220> FEATURE:
<221> NAME/KEY: MISC_FEATURE
<222> LOCATION: (25)..(25)
<223> OTHER INFORMATION: Lys, or any polar positively charged amino acid
<220> FEATURE:
<221> NAME/KEY: MISC_FEATURE
<222> LOCATION: (26)..(26)
<223> OTHER INFORMATION: Gly or any small aliphatic, nonpolar
      or slightly polar amino acid
<220> FEATURE:
<221> NAME/KEY: MISC_FEATURE
<222> LOCATION: (27)..(27)
<223> OTHER INFORMATION: Lys, or any polar positively charged amino acid
<220> FEATURE:
<221> NAME/KEY: MISC_FEATURE
<222> LOCATION: (28)..(28)
<223> OTHER INFORMATION: Phe, or a conservative amino-acid substitution
      Tyr, Trp, His or any nonpolar amino acid
<220> FEATURE:
<221> NAME/KEY: MISC_FEATURE
<222> LOCATION: (29)..(29)
<223> OTHER INFORMATION: Ala, or a conservative amino acid substitution
      Gly, Val, Leu, Ile or any nonpolar amino acid
<220> FEATURE:
<221> NAME/KEY: MISC_FEATURE
<222> LOCATION: (30)..(30)
<223> OTHER INFORMATION: Ser, or any small aliphatic, nonpolar or
      slightly polar amino acid
```

```
<220> FEATURE:
<221> NAME/KEY: MISC_FEATURE
<222> LOCATION: (31)..(31)
<223> OTHER INFORMATION: Ser, or Pro, or any small aliphatic, nonpolar
      or slightly polar amino acid
<220> FEATURE:
<221> NAME/KEY: MISC_FEATURE
<222> LOCATION: (32)..(32)
<223> OTHER INFORMATION: Lys, or any polar positively charged amino acid
<220> FEATURE:
<221> NAME/KEY: MISC_FEATURE
<222> LOCATION: (33)..(33)
<223> OTHER INFORMATION: Asp, or any polar, negatively charged
      amino acid and their amides
<220> FEATURE:
<221> NAME/KEY: MISC_FEATURE
<222> LOCATION: (34)..(34)
<223> OTHER INFORMATION: Pro, or Ser, or any small aliphatic, nonpolar
      or slightly polar residues
<220> FEATURE:
<221> NAME/KEY: MISC_FEATURE
<222> LOCATION: (35)..(35)
<223> OTHER INFORMATION: Lys, or any polar positively charged amino acid
<220> FEATURE:
<221> NAME/KEY: MISC_FEATURE
<222> LOCATION: (36)..(36)
<223> OTHER INFORMATION: Lys, or any polar positively charged amino acid
<220> FEATURE:
<221> NAME/KEY: MISC_FEATURE
<222> LOCATION: (37)..(37)
<223> OTHER INFORMATION: Lys, or any polar positively charged amino acid
<220> FEATURE:
<221> NAME/KEY: MISC_FEATURE
<222> LOCATION: (38)..(38)
<223> OTHER INFORMATION: Asp, or any polar, negatively charged
      amino acid and their amides
<220> FEATURE:
<221> NAME/KEY: MISC_FEATURE
<222> LOCATION: (39)..(39)
<223> OTHER INFORMATION: Ser, or any or any small aliphatic, nonpolar or
      slightly polar amino acid
<220> FEATURE:
<221> NAME/KEY: MISC_FEATURE
<222> LOCATION: (40)..(40)
<223> OTHER INFORMATION: is Ile, or a conservative amino acid
      substitution Gly, Arg, Val, Leu or any nonpolar amino acid

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa
        35                  40

<210> SEQ ID NO 2
<211> LENGTH: 20
<212> TYPE: PRT
<213> ORGANISM: Unknown
<220> FEATURE:
<223> OTHER INFORMATION: Artificial sequence
<220> FEATURE:
<221> NAME/KEY: MISC_FEATURE
<222> LOCATION: (1)..(1)
<223> OTHER INFORMATION: Glu, or any polar negatively charged amino
      acid, and their amides
<220> FEATURE:
<221> NAME/KEY: MISC_FEATURE
<222> LOCATION: (2)..(2)
<223> OTHER INFORMATION: Asp, or any polar, negatively charged
      amino acid and their amides
```

```
<220> FEATURE:
<221> NAME/KEY: MISC_FEATURE
<222> LOCATION: (3)..(3)
<223> OTHER INFORMATION: Ala, or a conservative amino acid substitution
      Gly, Val, Leu, Ile or any nonpolar amino acid
<220> FEATURE:
<221> NAME/KEY: MISC_FEATURE
<222> LOCATION: (4)..(4)
<223> OTHER INFORMATION: Asn, or any polar, negatively charged
      amino acid and their amides
<220> FEATURE:
<221> NAME/KEY: MISC_FEATURE
<222> LOCATION: (5)..(5)
<223> OTHER INFORMATION: Asn,  or any polar, negatively charged amino
      acid and their amides
<220> FEATURE:
<221> NAME/KEY: MISC_FEATURE
<222> LOCATION: (6)..(6)
<223> OTHER INFORMATION: Lys, or any polar positively charged amino acid
<220> FEATURE:
<221> NAME/KEY: MISC_FEATURE
<222> LOCATION: (7)..(7)
<223> OTHER INFORMATION: Ala, or a conservative amino acid substitution
      Gly, Val, Leu, Ile or any nonpolar amino acid
<220> FEATURE:
<221> NAME/KEY: MISC_FEATURE
<222> LOCATION: (8)..(8)
<223> OTHER INFORMATION: Thr, or any small aliphatic, nonpolar or
      slightly polar amino acid
<220> FEATURE:
<221> NAME/KEY: MISC_FEATURE
<222> LOCATION: (9)..(9)
<223> OTHER INFORMATION: Lys ,  or any polar positively charged amino
      acid
<220> FEATURE:
<221> NAME/KEY: MISC_FEATURE
<222> LOCATION: (10)..(10)
<223> OTHER INFORMATION: Phe, or any large aromatic amino acid
<220> FEATURE:
<221> NAME/KEY: MISC_FEATURE
<222> LOCATION: (11)..(11)
<223> OTHER INFORMATION: Leu, or a conservative amino acid substitution
      Gly, Arg, Val, Ile or any nonpolar amino acid
<220> FEATURE:
<221> NAME/KEY: MISC_FEATURE
<222> LOCATION: (12)..(12)
<223> OTHER INFORMATION: Glu, or any polar negatively charged amino
      acid, and their amides
<220> FEATURE:
<221> NAME/KEY: MISC_FEATURE
<222> LOCATION: (13)..(13)
<223> OTHER INFORMATION: Ser, or any small aliphatic, nonpolar or
      slightly polar amino acid
<220> FEATURE:
<221> NAME/KEY: MISC_FEATURE
<222> LOCATION: (14)..(14)
<223> OTHER INFORMATION: Ile, or a conservative amino acid substitution
      Gly, Arg, Val, Leu or any nonpolar amino acid
<220> FEATURE:
<221> NAME/KEY: MISC_FEATURE
<222> LOCATION: (15)..(15)
<223> OTHER INFORMATION: Lys, or any polar positively charged amino acid
<220> FEATURE:
<221> NAME/KEY: MISC_FEATURE
<222> LOCATION: (16)..(16)
<223> OTHER INFORMATION: Gly or any small aliphatic, nonpolar
      or slightly polar amino acid
<220> FEATURE:
<221> NAME/KEY: MISC_FEATURE
<222> LOCATION: (17)..(17)
<223> OTHER INFORMATION: Lys, or any polar positively charged amino acid
<220> FEATURE:
<221> NAME/KEY: MISC_FEATURE
<222> LOCATION: (18)..(18)
<223> OTHER INFORMATION: Phe, or a conservative amino-acid substitution
      Tyr, Trp, His or any nonpolar amino acid
```

-continued

<220> FEATURE:
<221> NAME/KEY: MISC_FEATURE
<222> LOCATION: (19)..(19)
<223> OTHER INFORMATION: Ala, or a conservative amino acid substitution
      Gly, Val, Leu, Ile or any nonpolar amino acid
<220> FEATURE:
<221> NAME/KEY: MISC_FEATURE
<222> LOCATION: (20)..(20)
<223> OTHER INFORMATION: Ser, or any small aliphatic, nonpolar or
      slightly polar amino acid

<400> SEQUENCE: 2

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 3
<211> LENGTH: 24
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Glu, or any polar negatively charged amino
      acid, and their amides
<220> FEATURE:
<221> NAME/KEY: MISC_FEATURE
<222> LOCATION: (2)..(2)
<223> OTHER INFORMATION: Phe, or any large aromatic amino acid
<220> FEATURE:
<221> NAME/KEY: MISC_FEATURE
<222> LOCATION: (3)..(3)
<223> OTHER INFORMATION: His, or any polar positively charged amino acid
<220> FEATURE:
<221> NAME/KEY: MISC_FEATURE
<222> LOCATION: (4)..(4)
<223> OTHER INFORMATION: Gly, or any small aliphatic, nonpolar or
      slightly polar amino acid,
<220> FEATURE:
<221> NAME/KEY: MISC_FEATURE
<222> LOCATION: (5)..(5)
<223> OTHER INFORMATION: Glu, or any polar negatively charged amino
      acid, and their amides
<220> FEATURE:
<221> NAME/KEY: MISC_FEATURE
<222> LOCATION: (6)..(6)
<223> OTHER INFORMATION: Asp, or any polar, negatively charged
      amino acid and their amides
<220> FEATURE:
<221> NAME/KEY: MISC_FEATURE
<222> LOCATION: (7)..(7)
<223> OTHER INFORMATION: Ala, or a conservative amino acid substitution
      Gly, Val, Leu, Ile or any nonpolar amino acid
<220> FEATURE:
<221> NAME/KEY: MISC_FEATURE
<222> LOCATION: (8)..(8)
<223> OTHER INFORMATION: Asn, or any polar, negatively charged
      amino acid and their amides
<220> FEATURE:
<221> NAME/KEY: MISC_FEATURE
<222> LOCATION: (9)..(9)
<223> OTHER INFORMATION: Asn,  or any polar, negatively charged amino
      acid and their amides
<220> FEATURE:
<221> NAME/KEY: MISC_FEATURE
<222> LOCATION: (10)..(10)
<223> OTHER INFORMATION: Lys, or any polar positively charged amino acid
<220> FEATURE:
<221> NAME/KEY: MISC_FEATURE
<222> LOCATION: (11)..(11)
<223> OTHER INFORMATION: Ala, or a conservative amino acid substitution
      Gly, Val, Leu, Ile or any nonpolar amino acid

```
<220> FEATURE:
<221> NAME/KEY: MISC_FEATURE
<222> LOCATION: (12)..(12)
<223> OTHER INFORMATION: Thr, or any small aliphatic, nonpolar or
      slightly polar amino acid
<220> FEATURE:
<221> NAME/KEY: MISC_FEATURE
<222> LOCATION: (13)..(13)
<223> OTHER INFORMATION: Lys , or any polar positively charged amino
      acid
<220> FEATURE:
<221> NAME/KEY: MISC_FEATURE
<222> LOCATION: (14)..(14)
<223> OTHER INFORMATION: Phe, or any large aromatic amino acid
<220> FEATURE:
<221> NAME/KEY: MISC_FEATURE
<222> LOCATION: (15)..(15)
<223> OTHER INFORMATION: Leu, or a conservative amino acid substitution
      Gly, Arg, Val, Ile or any nonpolar amino acid
<220> FEATURE:
<221> NAME/KEY: MISC_FEATURE
<222> LOCATION: (16)..(16)
<223> OTHER INFORMATION: Glu, or any polar negatively charged amino
      acid, and their amides
<220> FEATURE:
<221> NAME/KEY: MISC_FEATURE
<222> LOCATION: (17)..(17)
<223> OTHER INFORMATION: Ser, or any small aliphatic, nonpolar or
      slightly polar amino acid
<220> FEATURE:
<221> NAME/KEY: MISC_FEATURE
<222> LOCATION: (18)..(18)
<223> OTHER INFORMATION: Ile, or a conservative amino acid substitution
      Gly, Arg, Val, Leu or any nonpolar amino acid
<220> FEATURE:
<221> NAME/KEY: MISC_FEATURE
<222> LOCATION: (19)..(19)
<223> OTHER INFORMATION: Lys, or any polar positively charged amino acid
<220> FEATURE:
<221> NAME/KEY: MISC_FEATURE
<222> LOCATION: (20)..(20)
<223> OTHER INFORMATION: Gly or any small aliphatic, nonpolar
      or slightly polar amino acid
<220> FEATURE:
<221> NAME/KEY: MISC_FEATURE
<222> LOCATION: (21)..(21)
<223> OTHER INFORMATION: Lys, or any polar positively charged amino acid
<220> FEATURE:
<221> NAME/KEY: MISC_FEATURE
<222> LOCATION: (22)..(22)
<223> OTHER INFORMATION: Phe, or a conservative amino-acid substitution
      Tyr, Trp, His or any nonpolar amino acid
<220> FEATURE:
<221> NAME/KEY: MISC_FEATURE
<222> LOCATION: (23)..(23)
<223> OTHER INFORMATION: Ala, or a conservative amino acid substitution
      Gly, Val, Leu, Ile or any nonpolar amino acid
<220> FEATURE:
<221> NAME/KEY: MISC_FEATURE
<222> LOCATION: (24)..(24)
<223> OTHER INFORMATION: Ser, or any small aliphatic, nonpolar or
      slightly polar amino acid

<400> SEQUENCE: 3

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 4
<211> LENGTH: 20
<212> TYPE: PRT
<213> ORGANISM: Unknown
<220> FEATURE:
<223> OTHER INFORMATION: synthetic peptide
```

-continued

<400> SEQUENCE: 4

Glu Asp Ala Asn Asn Lys Ala Thr Lys Phe Leu Glu Ser Ile Lys Gly
1               5                   10                  15

Lys Phe Ala Ser
            20

<210> SEQ ID NO 5
<211> LENGTH: 20
<212> TYPE: PRT
<213> ORGANISM: Unknown
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: S-pentenyl-alanine
<220> FEATURE:
<221> NAME/KEY: MISC_FEATURE
<222> LOCATION: (13)..(13)
<223> OTHER INFORMATION: S-pentenyl-alanine

<400> SEQUENCE: 5

Glu Asp Ala Asn Asn Lys Ala Thr Xaa Phe Leu Glu Xaa Ile Lys Gly
1               5                   10                  15

Lys Phe Ala Ser
            20

<210> SEQ ID NO 6
<211> LENGTH: 20
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: S-pentenyl-alanine
<220> FEATURE:
<221> NAME/KEY: MISC_FEATURE
<222> LOCATION: (9)..(9)
<223> OTHER INFORMATION: S-pentenyl-alanine

<400> SEQUENCE: 6

Glu Asp Ala Asn Xaa Lys Ala Thr Xaa Phe Leu Glu Ser Ile Lys Gly
1               5                   10                  15

Lys Phe Ala Ser
            20

<210> SEQ ID NO 7
<211> LENGTH: 20
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (6)..(6)
<223> OTHER INFORMATION: S-pentenyl-alanine
<220> FEATURE:
<221> NAME/KEY: MISC_FEATURE
<222> LOCATION: (9)..(9)
<223> OTHER INFORMATION: S-pentenyl-alanine

<400> SEQUENCE: 7

Glu Asp Ala Asn Asn Xaa Ala Thr Xaa Phe Leu Glu Ser Ile Lys Gly
1               5                   10                  15

Lys Phe Ala Ser
            20

```
<210> SEQ ID NO 8
<211> LENGTH: 20
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (6)..(6)
<223> OTHER INFORMATION: R-octenyl-alanine
<220> FEATURE:
<221> NAME/KEY: MISC_FEATURE
<222> LOCATION: (13)..(13)
<223> OTHER INFORMATION: S-pentenyl-alanine

<400> SEQUENCE: 8

Glu Asp Ala Asn Asn Xaa Ala Thr Lys Phe Leu Glu Xaa Ile Lys Gly
1               5                   10                  15

Lys Phe Ala Ser
            20

<210> SEQ ID NO 9
<211> LENGTH: 20
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (13)..(13)
<223> OTHER INFORMATION: S-pentenyl-alanine
<220> FEATURE:
<221> NAME/KEY: MISC_FEATURE
<222> LOCATION: (17)..(17)
<223> OTHER INFORMATION: S-pentenyl-alanine

<400> SEQUENCE: 9

Glu Asp Ala Asn Asn Lys Ala Thr Lys Phe Leu Glu Xaa Ile Lys Gly
1               5                   10                  15

Asn Phe Ala Ser
            20

<210> SEQ ID NO 10
<211> LENGTH: 20
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (13)..(13)
<223> OTHER INFORMATION: R-octenyl-alanine
<220> FEATURE:
<221> NAME/KEY: MISC_FEATURE
<222> LOCATION: (20)..(20)
<223> OTHER INFORMATION: S-pentenyl-alanine

<400> SEQUENCE: 10

Glu Asp Ala Asn Asn Lys Ala Thr Lys Phe Leu Glu Xaa Ile Lys Gly
1               5                   10                  15

Lys Phe Ala Xaa
            20

<210> SEQ ID NO 11
<211> LENGTH: 20
<212> TYPE: PRT
<213> ORGANISM: Unknown
<220> FEATURE:
<223> OTHER INFORMATION: synthetic peptide
```

```
<220> FEATURE:
<221> NAME/KEY: MISC_FEATURE
<222> LOCATION: (9)..(9)
<223> OTHER INFORMATION: R-octenyl-alanine
<220> FEATURE:
<221> NAME/KEY: MISC_FEATURE
<222> LOCATION: (16)..(16)
<223> OTHER INFORMATION: S-pentenyl-alanine

<400> SEQUENCE: 11

Glu Asp Ala Asn Asn Lys Ala Thr Xaa Phe Leu Glu Ser Ile Lys Xaa
1               5                   10                  15

Lys Phe Ala Ser
            20

<210> SEQ ID NO 12
<211> LENGTH: 20
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (13)..(13)
<223> OTHER INFORMATION: R-pentenyl-alanine
<220> FEATURE:
<221> NAME/KEY: MISC_FEATURE
<222> LOCATION: (16)..(16)
<223> OTHER INFORMATION: S-pentenyl-alanine

<400> SEQUENCE: 12

Glu Asp Ala Asn Asn Lys Ala Thr Lys Phe Leu Glu Xaa Ile Lys Xaa
1               5                   10                  15

Lys Phe Ala Ser
            20

<210> SEQ ID NO 13
<211> LENGTH: 20
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (16)..(16)
<223> OTHER INFORMATION: S-pentenyl-alanine
<220> FEATURE:
<221> NAME/KEY: MISC_FEATURE
<222> LOCATION: (20)..(20)
<223> OTHER INFORMATION: S-pentenyl-alanine

<400> SEQUENCE: 13

Glu Asp Ala Asn Asn Lys Ala Thr Lys Phe Leu Glu Ser Ile Lys Xaa
1               5                   10                  15

Lys Phe Ala Xaa
            20

<210> SEQ ID NO 14
<211> LENGTH: 20
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (17)..(17)
<223> OTHER INFORMATION: R-pentenyl-alanine
```

```
<220> FEATURE:
<221> NAME/KEY: MISC_FEATURE
<222> LOCATION: (20)..(20)
<223> OTHER INFORMATION: S-pentenyl-alanine

<400> SEQUENCE: 14

Glu Asp Ala Asn Asn Lys Ala Thr Lys Phe Leu Glu Ser Ile Lys Gly
1               5                   10                  15

Xaa Phe Ala Xaa
            20

<210> SEQ ID NO 15
<211> LENGTH: 20
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (16)..(16)
<223> OTHER INFORMATION: R-pentenyl-alanine
<220> FEATURE:
<221> NAME/KEY: MISC_FEATURE
<222> LOCATION: (19)..(19)
<223> OTHER INFORMATION: S-pentenyl-alanine

<400> SEQUENCE: 15

Glu Asp Ala Asn Asn Lys Ala Thr Lys Phe Leu Glu Ser Ile Lys Xaa
1               5                   10                  15

Lys Phe Xaa Ser
            20

<210> SEQ ID NO 16
<211> LENGTH: 20
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (12)..(12)
<223> OTHER INFORMATION: R-octenyl-alanine
<220> FEATURE:
<221> NAME/KEY: MISC_FEATURE
<222> LOCATION: (19)..(19)
<223> OTHER INFORMATION: S-pentenyl-alanine

<400> SEQUENCE: 16

Glu Asp Ala Asn Asn Lys Ala Thr Lys Phe Leu Xaa Ser Ile Lys Gly
1               5                   10                  15

Lys Phe Xaa Ser
            20

<210> SEQ ID NO 17
<211> LENGTH: 20
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (12)..(12)
<223> OTHER INFORMATION: S-pentenyl-alanine
<220> FEATURE:
<221> NAME/KEY: MISC_FEATURE
<222> LOCATION: (16)..(16)
<223> OTHER INFORMATION: S-pentenyl-alanine
```

-continued

<400> SEQUENCE: 17

Glu Asp Ala Asn Asn Lys Ala Thr Lys Phe Leu Xaa Ser Ile Lys Xaa
1               5                   10                  15

Lys Phe Ala Ser
            20

<210> SEQ ID NO 18
<211> LENGTH: 20
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (9)..(9)
<223> OTHER INFORMATION: R-pentenyl-alanine
<220> FEATURE:
<221> NAME/KEY: MISC_FEATURE
<222> LOCATION: (12)..(12)
<223> OTHER INFORMATION: S-pentenyl-alanine

<400> SEQUENCE: 18

Glu Asp Ala Asn Asn Lys Ala Thr Xaa Phe Leu Xaa Ser Ile Lys Gly
1               5                   10                  15

Lys Phe Ala Ser
            20

<210> SEQ ID NO 19
<211> LENGTH: 20
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (8)..(8)
<223> OTHER INFORMATION: S-pentenyl-alanine
<220> FEATURE:
<221> NAME/KEY: MISC_FEATURE
<222> LOCATION: (12)..(12)
<223> OTHER INFORMATION: S-pentenyl-alanine

<400> SEQUENCE: 19

Glu Asp Ala Asn Asn Lys Ala Xaa Lys Phe Leu Xaa Ser Ile Lys Gly
1               5                   10                  15

Lys Phe Ala Ser
            20

<210> SEQ ID NO 20
<211> LENGTH: 20
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: Asn, or any polar, negatively charged
      amino acid and their amides
<220> FEATURE:
<221> NAME/KEY: MISC_FEATURE
<222> LOCATION: (5)..(5)
<223> OTHER INFORMATION: R-octenyl-alanine
<220> FEATURE:
<221> NAME/KEY: MISC_FEATURE
<222> LOCATION: (12)..(12)
<223> OTHER INFORMATION: S-pentenyl-alanine

```
<400> SEQUENCE: 20

Glu Asp Ala Xaa Xaa Lys Ala Thr Lys Phe Leu Xaa Ser Ile Lys Gly
1               5                   10                  15

Lys Phe Ala Ser
            20

<210> SEQ ID NO 21
<211> LENGTH: 20
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: R-pentenyl-alanine
<220> FEATURE:
<221> NAME/KEY: MISC_FEATURE
<222> LOCATION: (8)..(8)
<223> OTHER INFORMATION: S-pentenyl-alanine

<400> SEQUENCE: 21

Glu Asp Ala Asn Xaa Lys Ala Xaa Lys Phe Leu Glu Ser Ile Lys Gly
1               5                   10                  15

Lys Phe Ala Ser
            20

<210> SEQ ID NO 22
<211> LENGTH: 20
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (6)..(6)
<223> OTHER INFORMATION: R-octenyl-alanine
<220> FEATURE:
<221> NAME/KEY: MISC_FEATURE
<222> LOCATION: (13)..(13)
<223> OTHER INFORMATION: R,S-bis-pentenyl-glycine
<220> FEATURE:
<221> NAME/KEY: MISC_FEATURE
<222> LOCATION: (20)..(20)
<223> OTHER INFORMATION: S-octenyl-alanine

<400> SEQUENCE: 22

Glu Asp Ala Asn Asn Xaa Ala Thr Lys Phe Leu Glu Xaa Ile Lys Gly
1               5                   10                  15

Lys Phe Ala Xaa
            20

<210> SEQ ID NO 23
<211> LENGTH: 19
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: S-octenyl-alanine
<220> FEATURE:
<221> NAME/KEY: MISC_FEATURE
<222> LOCATION: (12)..(12)
<223> OTHER INFORMATION: R,S-bis-pentenyl-glycine
<220> FEATURE:
<221> NAME/KEY: MISC_FEATURE
<222> LOCATION: (16)..(16)
<223> OTHER INFORMATION: S-pentenyl-alanine
```

<400> SEQUENCE: 23

Asp Ala Asn Asn Xaa Ala Thr Lys Phe Leu Glu Xaa Ile Lys Gly Xaa
1               5                   10                  15

Phe Ala Ser

<210> SEQ ID NO 24
<211> LENGTH: 19
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: S-pentenyl-alanine
<220> FEATURE:
<221> NAME/KEY: MISC_FEATURE
<222> LOCATION: (8)..(8)
<223> OTHER INFORMATION: S-pentenyl-alanine
<220> FEATURE:
<221> NAME/KEY: MISC_FEATURE
<222> LOCATION: (12)..(12)
<223> OTHER INFORMATION: S-pentenyl-alanine
<220> FEATURE:
<221> NAME/KEY: MISC_FEATURE
<222> LOCATION: (16)..(16)
<223> OTHER INFORMATION: S-pentenyl-alanine

<400> SEQUENCE: 24

Asp Ala Asn Xaa Lys Ala Thr Xaa Phe Leu Glu Xaa Ile Lys Gly Xaa
1               5                   10                  15

Phe Ala Ser

<210> SEQ ID NO 25
<211> LENGTH: 20
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: S-pentenyl-alanine
<220> FEATURE:
<221> NAME/KEY: MISC_FEATURE
<222> LOCATION: (9)..(9)
<223> OTHER INFORMATION: S-pentenyl-alanine
<220> FEATURE:
<221> NAME/KEY: MISC_FEATURE
<222> LOCATION: (13)..(13)
<223> OTHER INFORMATION: R-octenyl-alanine
<220> FEATURE:
<221> NAME/KEY: MISC_FEATURE
<222> LOCATION: (20)..(20)
<223> OTHER INFORMATION: S-pentenyl-alanine

<400> SEQUENCE: 25

Glu Asp Ala Asn Xaa Lys Ala Thr Xaa Phe Leu Glu Xaa Ile Lys Gly
1               5                   10                  15

Lys Phe Ala Xaa
            20

<210> SEQ ID NO 26
<211> LENGTH: 24
<212> TYPE: PRT
<213> ORGANISM: Unknown

```
<220> FEATURE:
<223> OTHER INFORMATION: synthetic peptide
<220> FEATURE:
<221> NAME/KEY: MISC_FEATURE
<222> LOCATION: (10)..(10)
<223> OTHER INFORMATION: R-octenyl-alanine
<220> FEATURE:
<221> NAME/KEY: MISC_FEATURE
<222> LOCATION: (17)..(17)
<223> OTHER INFORMATION: S-pentenyl-alanine

<400> SEQUENCE: 26

Glu Phe His Gly Glu Asp Ala Asn Asn Xaa Ala Thr Lys Phe Leu Glu
1               5                   10                  15

Xaa Ile Lys Gly Lys Phe Ala Ser
            20

<210> SEQ ID NO 27
<211> LENGTH: 24
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: S-pentenyl-alanine
<220> FEATURE:
<221> NAME/KEY: MISC_FEATURE
<222> LOCATION: (6)..(6)
<223> OTHER INFORMATION: S-pentenyl-alanine
<220> FEATURE:
<221> NAME/KEY: MISC_FEATURE
<222> LOCATION: (10)..(10)
<223> OTHER INFORMATION: R-octenyl-alanine
<220> FEATURE:
<221> NAME/KEY: MISC_FEATURE
<222> LOCATION: (17)..(17)
<223> OTHER INFORMATION: S-pentenyl-alanine

<400> SEQUENCE: 27

Glu Xaa His Gly Glu Xaa Ala Asn Asn Xaa Ala Thr Lys Phe Leu Glu
1               5                   10                  15

Xaa Ile Lys Gly Lys Phe Ala Ser
            20

<210> SEQ ID NO 28
<211> LENGTH: 24
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: R-pentenyl-alanine
<220> FEATURE:
<221> NAME/KEY: MISC_FEATURE
<222> LOCATION: (6)..(6)
<223> OTHER INFORMATION: S-pentenyl-alanine
<220> FEATURE:
<221> NAME/KEY: MISC_FEATURE
<222> LOCATION: (10)..(10)
<223> OTHER INFORMATION: R-octenyl-alanine
<220> FEATURE:
<221> NAME/KEY: MISC_FEATURE
<222> LOCATION: (17)..(17)
<223> OTHER INFORMATION: S-pentenyl-alanine
```

```
<400> SEQUENCE: 28

Glu Phe Xaa Gly Glu Xaa Ala Asn Asn Xaa Ala Thr Lys Phe Leu Glu
1               5                   10                  15

Xaa Ile Lys Gly Lys Phe Ala Ser
            20

<210> SEQ ID NO 29
<211> LENGTH: 10
<212> TYPE: PRT
<213> ORGANISM: Unknown
<220> FEATURE:
<223> OTHER INFORMATION: synthetic peptide

<400> SEQUENCE: 29

Gly Arg Lys Lys Arg Arg Gln Arg Arg Arg
1               5                   10

<210> SEQ ID NO 30
<211> LENGTH: 15
<212> TYPE: PRT
<213> ORGANISM: Unknown
<220> FEATURE:
<223> OTHER INFORMATION: synthetic peptide

<400> SEQUENCE: 30

Arg Arg Arg Arg Asn Arg Thr Arg Arg Asn Arg Arg Arg Val Arg
1               5                   10                  15

<210> SEQ ID NO 31
<211> LENGTH: 13
<212> TYPE: PRT
<213> ORGANISM: Unknown
<220> FEATURE:
<223> OTHER INFORMATION: synthetic peptide

<400> SEQUENCE: 31

Thr Arg Arg Gln Arg Thr Arg Arg Ala Arg Arg Asn Arg
1               5                   10

<210> SEQ ID NO 32
<211> LENGTH: 12
<212> TYPE: PRT
<213> ORGANISM: Unknown
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: (S) - alpha - (2' - pentenyl)alanine)
<220> FEATURE:
<221> NAME/KEY: MISC_FEATURE
<222> LOCATION: (8)..(8)
<223> OTHER INFORMATION: (S) - alpha - (2' - pentenyl)alanine)

<400> SEQUENCE: 32

Ile Thr Phe Xaa Asp Leu Leu Xaa Tyr Tyr Gly Pro
1               5                   10

<210> SEQ ID NO 33
<211> LENGTH: 19
<212> TYPE: PRT
<213> ORGANISM: Unknown
<220> FEATURE:
<223> OTHER INFORMATION: KMTRAQRRAAARRNRWTAR
```

```
<400> SEQUENCE: 33

Lys Met Thr Arg Ala Gln Arg Arg Ala Ala Arg Arg Asn Arg Trp
1               5                   10                  15

Thr Ala Arg

<210> SEQ ID NO 34
<211> LENGTH: 9
<212> TYPE: PRT
<213> ORGANISM: Unknown
<220> FEATURE:
<223> OTHER INFORMATION: RRRRRRRRR

<400> SEQUENCE: 34

Arg Arg Arg Arg Arg Arg Arg Arg Arg
1               5

<210> SEQ ID NO 35
<211> LENGTH: 40
<212> TYPE: PRT
<213> ORGANISM: Homo sapiens

<400> SEQUENCE: 35

Met Glu Lys Phe Ala Pro Glu Phe His Gly Glu Asp Ala Asn Asn Arg
1               5                   10                  15

Ala Thr Lys Phe Leu Glu Ser Ile Lys Gly Lys Phe Thr Ser Pro Lys
                20                  25                  30

Asp Pro Lys Lys Lys Asp Ser Ile
            35                  40

<210> SEQ ID NO 36
<211> LENGTH: 40
<212> TYPE: PRT
<213> ORGANISM: Bos taurus

<400> SEQUENCE: 36

Met Glu Lys Phe Ala Pro Glu Phe His Gly Glu Asp Ala Asn Thr Lys
1               5                   10                  15

Ala Thr Lys Phe Leu Glu Ser Leu Lys Gly Lys Phe Thr Ser Ser Lys
                20                  25                  30

Asp Ser Arg Lys Lys Asp Ser Ile
            35                  40
```